(12) United States Patent
Garg et al.

(10) Patent No.: US 12,291,509 B2
(45) Date of Patent: May 6, 2025

(54) PROCESS FOR THE PREPARATION OF UV ABSORBERS

(71) Applicant: BASF SE, Ludwigshafen am Rhein (DE)

(72) Inventors: Rahul Garg, Navi Mumbai (IN); Mushtaq Patel, Navi Mumbai (IN); Prachin Kolambkar, Mumbai (IN); Mileen Kadam, Mumbai (IN); Deepak Makade, Mumbai (IN); Ramraj Bhatta, Mumbai (IN)

(73) Assignee: BASF SE, Ludwigshafen am Rhein (DE)

( * ) Notice: Subject to any disclaimer, the term of this patent is extended or adjusted under 35 U.S.C. 154(b) by 910 days.

(21) Appl. No.: 17/421,326

(22) PCT Filed: Jan. 2, 2020

(86) PCT No.: PCT/EP2020/050010
§ 371 (c)(1),
(2) Date: Jul. 7, 2021

(87) PCT Pub. No.: WO2020/144094
PCT Pub. Date: Jul. 16, 2020

(65) Prior Publication Data
US 2022/0064129 A1    Mar. 3, 2022

(30) Foreign Application Priority Data
Jan. 8, 2019  (EP) ..................................... 19150636

(51) Int. Cl.
*C07D 251/24*   (2006.01)

(52) U.S. Cl.
CPC ................. *C07D 251/24* (2013.01)

(58) Field of Classification Search
None
See application file for complete search history.

(56) References Cited

FOREIGN PATENT DOCUMENTS

| | | |
|---|---|---|
| CN | 106083751 A | 11/2016 |
| EP | 2762483 A1 | 8/2014 |
| TW | I236472 B | 7/2005 |
| WO | 96/28431 A1 | 9/1996 |
| WO | 2012034932 A1 | 3/2012 |

OTHER PUBLICATIONS

PAN. Journal of Organic Chemistry, 2017, 82, 10043-10050 (Year: 2017).*
Brunetti, et al., "Die Synthese von asymmetrisch substituierten o-Hydroxyphenyl-s-triazinen", Helvetica, vol. 55, Issue 5, Jul. 10, 1972, pp. 1566-1595.
European Search Report for EP Patent Application No. 19150636.9, Issued on May 8, 2019, 3 pages.
International Search Report for PCT Patent Application No. PCT/EP2020/050010, Issued on Feb. 26, 2020, 4 pages.
Langmead, et al., "Identification of Novel Adenosine A2A Receptor Antagonists by Virtual Screening", Journal of Medicinal Chemistry, vol. 55, Issue 5, Mar. 8, 2012, pp. 1904-1909.
Tanimoto, et al., "Synthesis of the Ultraviolet light Absorbers having 2-(2-Hydroxyphenyl)-1,3,5-triazine Structure as the Functional Moiety", Senryo to Yakahin, Dyestuffs & Chemicals, vol. 40, Issue 12, Dec. 1995, pp. 325-339.
Office Action mailed Nov. 21, 2024 in U.S. Appl. No. 17/421,301.

* cited by examiner

*Primary Examiner* — Noble E Jarrell
(74) *Attorney, Agent, or Firm* — ArentFox Schiff LLP

(57) ABSTRACT

The presently claimed invention relates to a novel, highly efficient and general process for the preparation of UV absorbers.

14 Claims, No Drawings

PROCESS FOR THE PREPARATION OF UV ABSORBERS

CROSS-REFERENCE TO RELATED APPLICATIONS

This application is a National Stage Entry of PCT/EP2020/050010, filed Jan. 2, 2020, which claims priority to EP Application Serial No. 19150636.9, filed Jan. 8, 2019, the disclosures of each of which are hereby incorporated by reference in their entireties.

FIELD OF THE INVENTION

The presently claimed invention relates to a novel, highly efficient and general process for the preparation of UV absorbers.

BACKGROUND OF THE INVENTION

Triazine UV absorbers are an important class of organic compounds which have a wide variety of applications. One of the most important areas of application is the protection and stabilization of organic materials such as plastics, polymers, coating materials, and photographic recording materials against damages by light, heat, oxygen, or environmental forces. Other areas of applications include cosmetics, fibres, dyes, etc.

Triazine-based UV absorbers typically include at least one 2-oxyaryl substituent on the 1,3,5-triazine ring. Triazine-based UV absorber compounds having aromatic substituents at the 2-, 4-, and 6-positions of the 1,3,5-triazine ring and having at least one of the aromatic rings substituted at the ortho position with a hydroxyl group or blocked hydroxyl group are generally the preferred compounds.

There are several processes known in the literature for the preparation of triazine-based UV absorbers. (See, H. Brunetti and C. E. Luethi, [0008] Helvetica Chimica Acta, 1972, 55, 1566-1595, S. Tanimoto et al., Senryo to Yakahin, 1995, 40(120), 325-339).

Many of the approaches consist of three stages. The first stage, the synthesis of the key intermediate, 2-chloro-4,6-bisaryl-1,3,5-triazine, from commercially available materials can involve single-step or multi-step processes. Thereafter, in the second stage, 2-chloro-4,6-bisaryl-1,3,5-triazine is subsequently arylated with 1,3-dihydroxybenzene (resorcinol) or a substituted 1,3-dihydroxybenzene in the presence of a Lewis acid to form the parent compound 2-(2,4-dihydroxyaryl)-4,6-bisaryl-1,3,5-triazine. The parent compound 2-(2,4-dihydroxyaryl)-4,6-bisaryl-1,3,5-triazine, as mentioned above, may be further functionalized, e.g., alkylated, to prepare a final product 2-(2-hydroxy-4-alkoxyaryl)-4,6-bisaryl-1,3,5-triazine.

Several approaches have been reported in the literature on the synthesis of the key intermediate 2-chloro-4,6-bisaryl-1,3,5-triazine. However, the problem associated with these approaches is that they lead to the formation of impurities that are difficult to separate. The impurities react in the subsequent steps and will in turn lead to the formation of undesired by-products. Thus, there is a need for a cost effective commercially viable process for the preparation of UV absorbers without the formation of impurities or with minimal formation of colouring impurities.

Hence, it is an object of the presently claimed invention to provide a highly efficient and general process for the preparation of substituted triazine compounds that are useful as UV absorbers.

SUMMARY OF THE INVENTION

Surprisingly, it was found that reacting the 4,6-dichloro-1,3,5-triazin-2-amine with at least one aromatic compound in the presence of at least one acid allowed for the formation of 4,6-diaryl-1,3,5-triazin-2-amine. The 4,6-diaryl-1,3,5-triazin-2-amine can easily be converted into a halogenated intermediate which can subsequently be converted into the desired UV absorber compounds.

Accordingly, one aspect of the presently claimed invention is directed to a process for preparing a compound of formula (A)

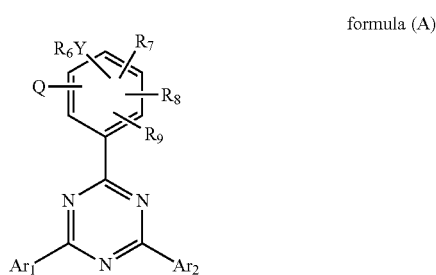

formula (A)

wherein $Ar_1$ and $Ar_2$ are independently a moiety of the formula (B),

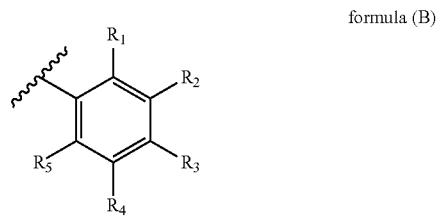

formula (B)

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s);

Q is selected from hydrogen and OH;

$R_6$ is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OC(=O)R, CN, SR, S(=O)$_2$R, S(=O)$_2$OH and S(=O)$_2$OM, wherein M is an alkali metal, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen, O, —NR", or S, wherein R" is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of:

i) reacting at least one compound of formula (C)

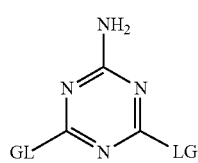

formula (C)

wherein LG is halogen, O—S(=O)$_2$CF$_3$ or O—S(=O)$_2$CH$_3$;

with at least one compound of formula (B1)

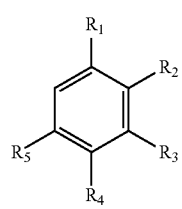

formula (B1)

wherein $R_1$, $R_2$, $R_3$, $R_4$ and $R_5$ are defined as above; in the presence of at least one acid to obtain a compound of formula (D)

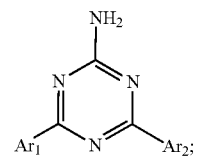

formula (D)

wherein Ar$_1$ and Ar$_2$ are define as above;

ii) reacting the compound of formula (D) obtained according to step i) with at least one metal hydroxide to obtain a compound of formula (E)

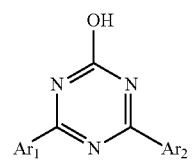

formula (E)

wherein Ar$_1$ and Ar$_2$ are defined as above;

reacting the compound of formula (E) obtained according to step ii) with at least one halogenating reagent to obtain a compound of formula (F)

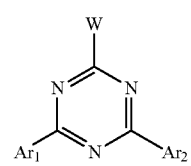

formula (F)

wherein Ar$_1$ and Ar$_2$ are defined as above, and W is selected from the group consisting of F, Cl, and Br; and iii) reacting at least one compound of formula (F) obtained according to step iii) and at least one compound of formula (G),

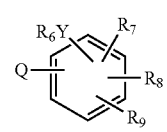

formula (G)

wherein Y, Q, $R^6$, $R^7$, $R^8$ and $R^9$ are defined as above, in the presence of an at least one acid to obtain a compound of formula (A).

DETAILED DESCRIPTION

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or 'a', 'b', 'c', etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(b)', '(c)', '(d)', 'i', 'ii' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

In an embodiment, the presently claimed invention is directed to a process for preparing a compound of formula (A)

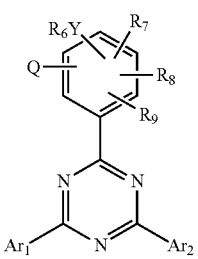

formula (A)

wherein Ar$_1$ and Ar$_2$ are independently a moiety of the formula (B),

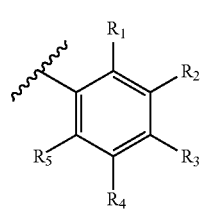

formula (B)

wherein

R$_1$, R$_2$, R$_3$, R$_4$ and R$_5$ are independently selected from the group consisting of hydrogen, halogen, substituted or unsubstituted, linear or branched C$_1$-C$_{24}$ alkyl, substituted or unsubstituted, linear or branched C$_2$-C$_{24}$ alkenyl, substituted or unsubstituted C$_5$-C$_{24}$ cycloalkyl, substituted or unsubstituted C$_5$-C$_{24}$ cycloalkenyl, substituted or unsubstituted C$_6$-C$_{24}$ aryl, substituted or unsubstituted C$_7$-C$_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or R$_1$ and R$_2$ together with the carbon atoms to which they are bonded or R$_2$ and R$_3$ together with the carbon atoms to which they are bonded or R$_3$ and R$_4$ together with the carbon atoms to which they are bonded or R$_4$ and R$_5$ together with the carbon atoms to which they are bonded form an unsaturated or aromatic 5- to 20-membered carbocyclic ring that optionally contains 1, 2 or 3 heteroatom(s) selected from O, N or S as ring member(s);

Q is selected from hydrogen and OH;

R$_6$ is selected from the group consisting of hydrogen, substituted or unsubstituted, linear or branched C$_1$-C$_{24}$ alkyl, substituted or unsubstituted, linear or branched C$_2$-C$_{24}$ alkenyl, substituted or unsubstituted C$_6$-C$_{24}$ aryl, substituted or unsubstituted C$_7$-C$_{24}$ arylalkyl, substituted or unsubstituted C$_5$-C$_{24}$ cycloalkyl and substituted or unsubstituted C$_5$-C$_{24}$ cycloalkenyl, and C(=O)R;

R$_7$, R$_8$ and R$_9$ are independently selected from the group consisting of hydrogen, halogen, substituted or unsubstituted, linear or branched C$_1$-C$_{24}$ alkyl, substituted or unsubstituted, linear or branched C$_2$-C$_{24}$ alkenyl, substituted or unsubstituted C$_6$-C$_{24}$ aryl, substituted or unsubstituted C$_7$-C$_{24}$ arylalkyl, substituted or unsubstituted C$_5$-C$_{24}$ cycloalkyl, substituted or unsubstituted C$_5$-C$_{24}$ cycloalkenyl, C(=O)R, OR, NRR', C(=O)NRR', OC(=O)R, CN, SR, S(=O)$_2$R, S(=O)$_2$OH and S(=O)$_2$OM, wherein M is an alkali metal, or R$_7$ and R$_8$ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen, O, —NR", or S, wherein R" is selected from the group consisting of hydrogen, substituted or unsubstituted, linear or branched C$_1$-C$_{24}$ alkyl, substituted or unsubstituted, linear or branched C$_2$-C$_{24}$ alkenyl, substituted or unsubstituted C$_6$-C$_{24}$ aryl, substituted or unsubstituted C$_7$-C$_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of:

i) reacting at least one compound of formula (C)

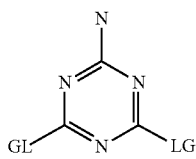

formula (C)

wherein LG is halogen, O—S(=O)$_2$CF$_3$ or O—S(=O)$_2$CH$_3$;

with at least one compound of formula (B1)

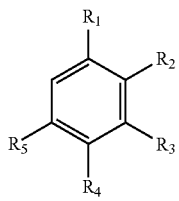

formula (B1)

wherein $R_1$, $R_2$, $R_3$, $R_4$ and $R_5$ are defined as above;
in the presence of at least one acid to obtain a compound of formula (D)

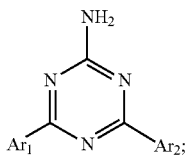

formula (D)

wherein Ar$_1$ and Ar$_2$ are defined as above;

ii) reacting the compound of formula (D) obtained according to step i) with at least one metal hydroxide to obtain a compound of formula (E)

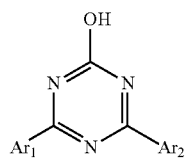

formula (E)

wherein Ar$_1$ and Ar$_2$ are defined as above;

iii) reacting the compound of formula (E) obtained according to step ii) with at least one halogenating reagent to obtain a compound of formula (F)

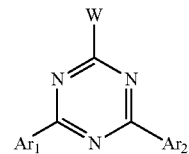

formula (F)

wherein Ar$_1$ and Ar$_2$ are defined as above, and
W is selected from the group consisting of F, Cl, and Br; and iv) reacting at least one compound of formula (F) obtained according to step iii) and at least one compound of formula (G),

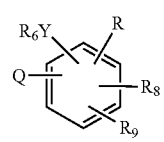

formula (G)

wherein Y, Q, $R^6$, $R^7$, $R^8$ and $R^9$ are defined as above,
in the presence of an at least one acid to obtain a compound of formula (A).

More preferably, the presently claimed invention is directed to a process for preparing a compound of formula (A)

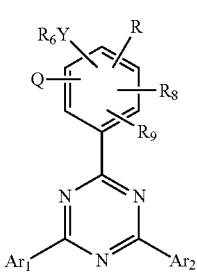

formula (A)

wherein Ar$_1$ and Ar$_2$ are independently a moiety of the formula (B),

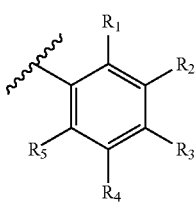

formula (B)

wherein

Q is selected from hydrogen and OH;

$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or R₁ and R₂ together with the carbon atoms to which they are bonded or R₂ and R₃ together with the carbon atoms to which they are bonded or R₃ and R₄ together with the carbon atoms to which they are bonded or R₄ and R₅ together with the carbon atoms to which they are bonded form an unsaturated or aromatic 5- to 20-membered carbocyclic ring that optionally contains 1, 2 or 3 heteroatom(s) selected from O, N or S as ring member(s);

R₆ is selected from the group consisting of hydrogen, substituted or unsubstituted, linear or branched C₁-C₂₄ alkyl, substituted or unsubstituted C₆-C₂₄ aryl, substituted or unsubstituted C₇-C₂₄ arylalkyl, and C(=O)R;

R₇, R₈ and R₉ are independently selected from the group consisting of hydrogen, halogen, substituted or unsubstituted, linear or branched C₁-C₂₄ alkyl, substituted or unsubstituted C₆-C₂₄ aryl, substituted or unsubstituted C₇-C₂₄ arylalkyl, C(=O)R, OR, NRR', C(=O)NRR', OC(=O)R, CN, SR, S(=O)₂R, S(=O)₂OH and S(=O)₂OM, wherein M is an alkali metal, or R₇ and R₈ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen, O, —NR", or S, wherein R" is selected from the group consisting of hydrogen, substituted or unsubstituted, linear or branched C₁-C₂₄ alkyl, substituted or unsubstituted, linear or branched C₂-C₂₄ alkenyl, substituted or unsubstituted C₆-C₂₄ aryl, substituted or unsubstituted C₇-C₂₄ arylalkyl, substituted or unsubstituted C₅-C₂₄ cycloalkyl and substituted or unsubstituted C₅-C₂₄ cycloalkenyl; with the proviso that in case Y is hydrogen or halogen, then R₆ is not present; and R and R' are independently selected from the group consisting of hydrogen, substituted or unsubstituted, linear or branched C₁-C₂₄ alkyl, substituted or unsubstituted, linear or branched C₂-C₂₄ alkenyl, substituted or unsubstituted C₅-C₂₄ cycloalkyl, substituted or unsubstituted C₅-C₂₄ cycloalkenyl, substituted or unsubstituted C₆-C₂₄ aryl and substituted or unsubstituted C₇-C₂₄ arylalkyl; comprising at least the steps of:

i) reacting at least one compound of formula (C)

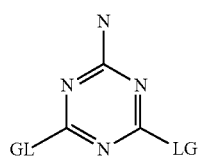

formula (C)

wherein LG is halogen, O—S(=O)₂CF₃ or O—S(=O)₂CH₃;

with at least one compound of formula (B1)

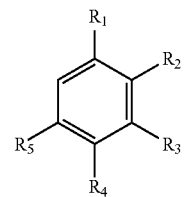

formula (B1)

wherein R₁, R₂, R₃, R₄ and R₅ are defined as above;

in the presence of at least one acid to obtain a compound of formula (D)

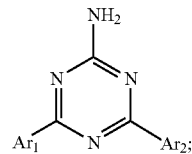

formula (D)

wherein Ar₁ and Ar₂ are defined as above;

ii) reacting the compound of formula (D) obtained according to step i) with at least one metal hydroxide to obtain a compound of formula (E)

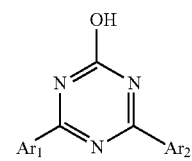

formula (E)

wherein Ar₁ and Ar₂ are defined as above;

iii) reacting the compound of formula (E) obtained according to step ii) with at least one halogenating reagent to obtain a compound of formula (F)

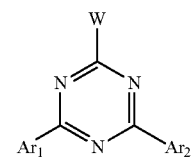

formula (F)

wherein Ar₁ and Ar₂ are defined as above, and

W is selected from the group consisting of F, Cl, and Br; and iv) reacting at least one compound of formula (F) obtained according to step iii) and at least one compound of formula (G),

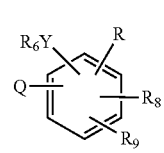

formula (G)

wherein Y, Q, $R_6$, $R_7$, $R_8$ and $R_9$ are defined as above,
in the presence of an at least one acid to obtain a compound of formula (A).

Even more preferably, the presently claimed invention is directed to a process for preparing a compound of formula (A)

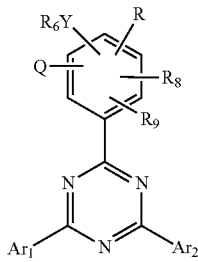

formula (A)

wherein $Ar_1$ and $Ar_2$ are independently a moiety of the formula (B),

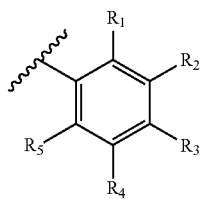

formula (B)

wherein
Q is selected from hydrogen and OH;
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, C(=O)R, OR; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s);
$R_6$ is selected from the group consisting of hydrogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, and C(=O)R;
$R_7$, $R_8$ and $R_9$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, C(=O)R, OR, or
$R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen and O; with the proviso that in case Y is hydrogen or halogen, then $R_6$ is not present;
R is independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;
comprising at least the steps of:
i) reacting at least one compound of formula (C)

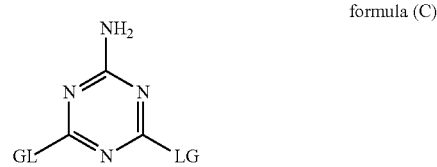

formula (C)

wherein LG is halogen, O—S(=O)$_2$CF$_3$ or O—S(=O)$_2$CH$_3$;
with at least one compound of formula (B1)

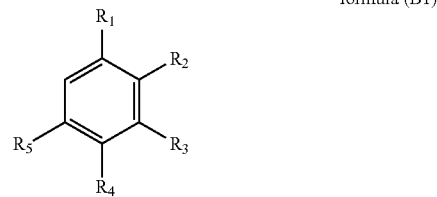

formula (B1)

wherein $R_1$, $R_2$, $R_3$, $R_4$ and $R_5$ are defined as above;
in the presence of at least one acid to obtain a compound of formula (D)

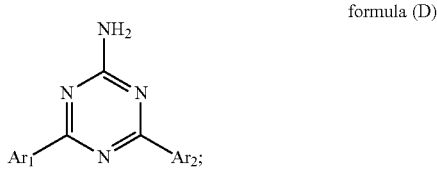

formula (D)

wherein $Ar_1$ and $Ar_2$ are defined as above;
ii) reacting the compound of formula (D) obtained according to step i) with at least one metal hydroxide to obtain a compound of formula (E)

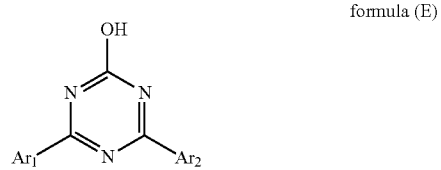

formula (E)

wherein $Ar_1$ and $Ar_2$ are defined as above;
iii) reacting the compound of formula (E) obtained according to step ii) with at least one halogenating reagent to obtain a compound of formula (F)

formula (F)

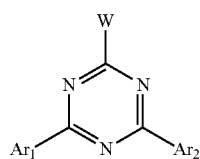

wherein Ar$_1$ and Ar$_2$ are defined as above, and
W is selected from the group consisting of F, Cl, and Br; and iv) reacting at least one compound of formula (F) obtained according to step iii) and at least one compound of formula (G),

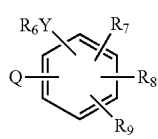

formula (G)

wherein Y, Q, R$_6$, R$_7$, R$_8$ and R$_9$ are defined as above, in the presence of an at least one acid to obtain a compound of formula (A).

Most preferably, the presently claimed invention is directed to a process for preparing a compound of formula (A)

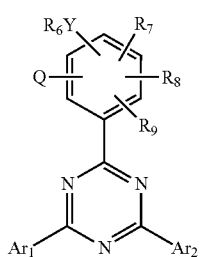

formula (A)

wherein Ar$_1$ and Ar$_2$ are independently a moiety of the formula (B),

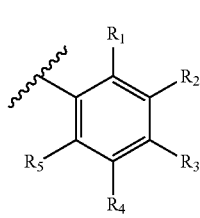

formula (B)

wherein
Q is selected from hydrogen and OH;
R$_1$, R$_2$, R$_3$, R$_4$ and R$_5$ are independently selected from the group consisting of hydrogen, halogen, substituted or unsubstituted, linear or branched C$_1$-C$_{24}$ alkyl, substituted or unsubstituted C$_6$-C$_{24}$ aryl, substituted or unsubstituted C$_7$-C$_{24}$ arylalkyl, C(=O)R, OR;
R$_6$ is selected from the group consisting of hydrogen, substituted or unsubstituted, linear or branched C$_1$-C$_{24}$ alkyl, substituted or unsubstituted C$_6$-C$_{24}$ aryl, substituted or unsubstituted C$_7$-C$_{24}$ arylalkyl, and C(=O)R;

R$_7$, R$_8$ and R$_9$ are independently selected from the group consisting of hydrogen, halogen, substituted or unsubstituted, linear or branched C$_1$-C$_{24}$ alkyl, substituted or unsubstituted C$_6$-C$_{24}$ aryl, substituted or unsubstituted C$_7$-C$_{24}$ arylalkyl, C(=O)R, OR, or Y is selected from the group consisting of hydrogen, halogen and O; with the proviso that in case Y is hydrogen or halogen, then R$_6$ is not present;

R is independently selected from the group consisting of hydrogen, substituted or unsubstituted, linear or branched C$_1$-C$_{24}$ alkyl, substituted or unsubstituted C$_6$-C$_{24}$ aryl and substituted or unsubstituted C$_7$-C$_{24}$ arylalkyl;

comprising at least the steps of:
i) reacting at least one compound of formula (C)

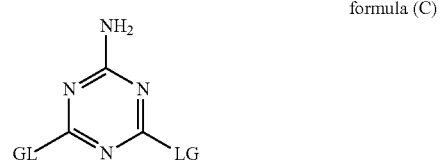

formula (C)

wherein LG is halogen, O—S(=O)$_2$CF$_3$ or O—S(=O)$_2$CH$_3$;
with at least one compound of formula (B1)

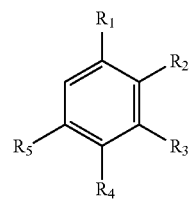

formula (B1)

wherein R$_1$, R$_2$, R$_3$, R$_4$ and R$_5$ are defined as above;
in the presence of at least one acid to obtain a compound of formula (D)

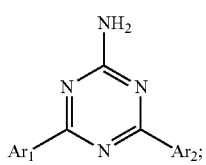

formula (D)

wherein Ar$_1$ and Ar$_2$ are defined as above;
ii) reacting the compound of formula (D) obtained according to step i) with at least one metal hydroxide to obtain a compound of formula (E)

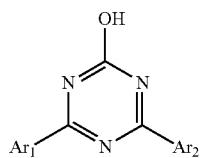

formula (E)

wherein Ar$_1$ and Ar$_2$ are defined as above;

iii) reacting the compound of formula (E) obtained according to step ii) with at least one halogenating reagent to obtain a compound of formula (F)

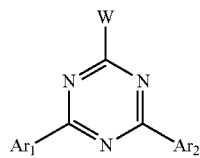

formula (F)

wherein Ar$_1$ and Ar$_2$ are defined as above, and

W is selected from the group consisting of F, Cl, and Br; and iv) reacting at least one compound of formula (F) obtained according to step iii) and at least one compound of formula (G),

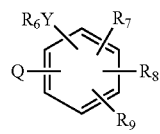

formula (G)

wherein Y, Q, R$_6$, R$_7$, R$_8$ and R$_9$ are defined as above, in the presence of an at least one acid to obtain a compound of formula (A).

In particular preferably, the presently claimed invention is directed to a process for preparing a compound of formula (A)

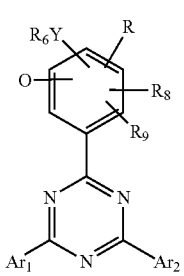

formula (A)

wherein Ar$_1$ and Ar$_2$ are independently a moiety of the formula (B),

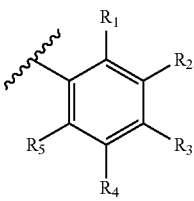

formula (B)

wherein

Q is selected from hydrogen and OH;

R$_1$, R$_2$, R$_3$, R$_4$ and R$_5$ are independently selected from the group consisting of hydrogen, substituted or unsubstituted, linear or branched C$_1$-C$_{24}$ alkyl, substituted or unsubstituted C$_6$-C$_{24}$ aryl, C(=O)R, OR;

R$_6$ is selected from the group consisting of hydrogen, substituted or unsubstituted, linear or branched C$_1$-C$_{24}$ alkyl, and C(=O)R;

R$_7$, R$_8$ and R$_9$ are independently selected from the group consisting of hydrogen, substituted or unsubstituted, linear or branched C1-C24 alkyl, substituted or unsubstituted C6-C24 aryl, C(=O)R, OR, or Y is selected from the group consisting of hydrogen and O; with the proviso that in case Y is hydrogen, then R$_6$ is not present;

R is independently selected from the group consisting of hydrogen, substituted or unsubstituted, linear or branched C$_1$-C$_{24}$ alkyl, substituted or unsubstituted C$_6$-C$_{24}$ aryl and substituted or unsubstituted C$_7$-C$_{24}$ arylalkyl;

comprising at least the steps of:

i) reacting at least one compound of formula (C)

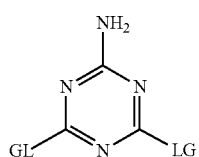

formula (C)

wherein LG is halogen, O—S(=O)$_2$CF$_3$ or O—S(=O)$_2$CH$_3$;

with at least one compound of formula (B1)

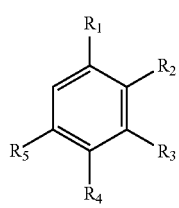

formula (B1)

wherein R$_1$, R$_2$, R$_3$, R$_4$ and R$_5$ are defined as above;

in the presence of at least one acid to obtain a compound of formula (D)

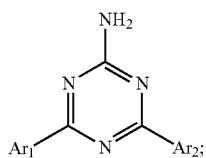
formula (D)

wherein Ar₁ and Ar₂ are defined as above;

ii) reacting the compound of formula (D) obtained according to step i) with at least one metal hydroxide to obtain a compound of formula (E)

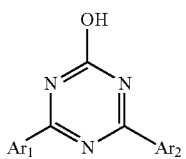
formula (E)

wherein Ar₁ and Ar₂ are defined as above;

iii) reacting the compound of formula (E) obtained according to step ii) with at least one halogenating reagent to obtain a compound of formula (F)

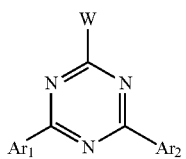
formula (F)

wherein Ar₁ and Ar₂ are defined as above, and

W is selected from the group consisting of F, Cl, and Br; and iv) reacting at least one compound of formula (F) obtained according to step iii) and at least one compound of formula (G),

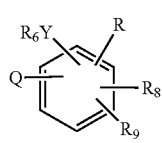
formula (G)

wherein Y, Q, R₆, R₇, R₈ and R₉ are defined as above, in the presence of an at least one acid to obtain a compound of formula (A).

Even more particularly preferably, the presently claimed invention is directed to a process for preparing a compound of formula (A)

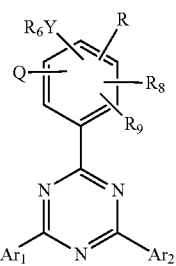
formula (A)

wherein Ar₁ and Ar₂ are independently a moiety of the formula (B), formula (B)

wherein

Q is selected from hydrogen and OH;

$R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, C(=O)R, OR;

$R_6$ is selected from the group consisting of hydrogen, substituted or unsubstituted, linear or branched $C_1$-$C_{24}$ alkyl, and C(=O)R;

$R_7$, $R_8$ and $R_9$ are hydrogen, or

Y is selected from the group consisting of hydrogen and O; with the proviso that in case Y is hydrogen, then $R_6$ is not present;

R is independently selected from the group consisting of hydrogen and substituted or unsubstituted, linear or branched $C_1$-$C_{24}$ alkyl;

comprising at least the steps of:

i) reacting at least one compound of formula (C)

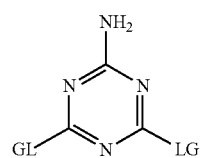
formula (C)

wherein LG is halogen;
with at least one compound of formula (B1)

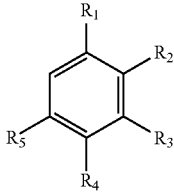

formula (B1)

wherein $R_1$, $R_2$, $R_3$, $R_4$ and $R_5$ are defined as above;
in the presence of at least one Lewis acid to obtain a compound of formula (D)

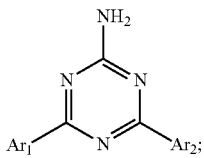

formula (D)

wherein $Ar_1$ and $Ar_2$ are defined as above;

ii) reacting the compound of formula (D) obtained according to step i) with at least one metal hydroxide to obtain a compound of formula (E

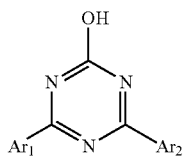

formula (E)

wherein $Ar_1$ and $Ar_2$ are defined as above;

iii) reacting the compound of formula (E) obtained according to step ii) with at least one halogenating reagent to obtain a compound of formula (F)

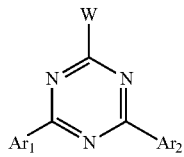

formula (F)

wherein $Ar_1$ and $Ar_2$ are defined as above, and
W is selected from the group consisting of F, Cl, and Br; and iv) reacting at least one compound of formula (F) obtained according to step iii) and at least one compound of formula (G),

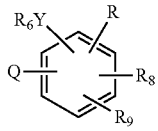

formula (G)

wherein Y, Q, $R_6$, $R_7$, $R_8$ and $R_9$ are defined as above, in the presence of an at least one Lewis acid to obtain a compound of formula (A).

Within the context of the presently claimed invention, the term "alkyl", as used herein, refers to an acylic saturated aliphatic group, including linear or branched alkyl saturated hydrocarbon radicals, denoted by a general formula $C_nH_{2n+1}$, and wherein n is the number of carbon atoms such as 1, 2, 3, 4, etc.

In a preferred embodiment, the unsubstituted linear $C_1$-$C_{24}$ alkyl is preferably selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl and tetracosyl; more preferably selected from the group consisting of hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl and tetracosyl; even more preferably selected from the group consisting of methyl, ethyl, propyl, butyl, pentyl, hexyl, heptyl, octyl, nonyl, decyl, undecyl, dodecyl, tridecyl, tetradecyl and pentadecyl; most preferably selected from the group consisting of methyl, ethyl, propyl, butyl, pentyl, hexyl, heptyl, octyl, nonyl, decyl, undecyl and dodecyl; and in particular preferably selected from the group consisting of methyl, ethyl, propyl, butyl, pentyl, hexyl, heptyl, octyl, nonyl and decyl.

In a preferred embodiment, the unsubstituted branched $C_1$-$C_{24}$ alkyl is preferably selected from the group consisting of isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl, more preferably selected from the group consisting of 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl, iso-eicosyl, 2-methyltricosyl, 2-ethyldocosyl, 3-ethylhenicosyl, 3-ethylicosyl, 4-propylhenicosyl, propylnonadecyl, 6-butyldodecyl and 5-ethylundecyl.

In a preferred embodiment, the substituted, linear or branched, $C_1$-$C_{24}$ alkyl refers to a branched or linear saturated hydrocarbon group having $C_1$-$C_{24}$ carbon atoms substituted with functional groups selected from the group consisting of hydroxy, alkoxy, C(=O)R, CN and SR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

In a preferred embodiment, the substituted, linear or branched, $C_1$-$C_{24}$ alkyl refers to a branched or linear saturated hydrocarbon group having $C_1$-$C_{24}$ carbon atoms substituted with functional groups selected from the group consisting of hydroxy, alkoxy, C(=O)R, CN and SR, preferably selected from the group consisting of 1-hydroxy methyl, 1-methoxy methyl, 1-hydroxy ethyl, 1-hydroxy propyl, 1-hydroxy butyl, 1-hydroxy pentyl, 1-hydroxy hexyl, 1-hydroxy heptyl, 1-hydroxy octyl, 1-hydroxy nonyl, decyl, 1-hydroxy undecyl, 1-hydroxy dodecyl, 1-hydroxy tridecyl, 1-hydroxy tetradecyl, 1-hydroxy pentadecyl, 1-hydroxy hexadecyl, 1-hydroxy heptadecyl, 1-hydroxy octadecyl, 1-hydroxy nonadecyl, 1-hydroxy eicosyl, 1-hydroxy henicosyl, 1-hydroxy docosyl, 1-hydroxy tricosyl, 1-hydroxy tetracosyl, 1-methoxy methyl, 1-methoxy ethyl, 1-methoxy propyl, 1-methoxy butyl, 1-methoxy pentyl, 1-methoxy hexyl, 1-methoxy heptyl, 1-methoxy octyl, 1-methoxy nonyl, decyl, 1-methoxy undecyl, 1-methoxy dodecyl, 1-methoxy tridecyl, 1-methoxy tetradecyl, 1-methoxy pentadecyl, 1-methoxy hexadecyl, 1-methoxy heptadecyl, 1-methoxy octadecyl, 1-methoxy nonadecyl, 1-methoxy eicosyl, 1-methoxy henicosyl, 1-methoxy docosyl, 1-methoxy tricosyl, 1-methoxy tetracosyl, 2-methoxy propyl, 2-methoxy butyl, 2-methoxy pentyl, 2-methoxy hexyl, 2-methoxy heptyl, 2-methoxy octyl, 2-methoxy nonyl, decyl, 2-methoxy undecyl, 2-methoxy dodecyl, 2-methoxy tridecyl, 2-methoxy tetradecyl, 2-methoxy pentadecyl, 2-methoxy hexadecyl, 2-methoxy heptadecyl, 2-methoxy octadecyl, 2-methoxy nonadecyl, 2-methoxy eicosyl, 2-methoxy henicosyl, 2-methoxy docosyl, 2-methoxy tricosyl, 2-methoxy tetracosyl, 1-acetoxy methyl, 1-acetoxy ethyl, 1-acetoxy propyl, 1-acetoxy butyl, 1-acetoxy pentyl, 1-acetoxy hexyl, 1-acetoxy heptyl, 1-acetoxy octyl, 1-acetoxy nonyl, decyl, 1-acetoxy undecyl, 1-acetoxy dodecyl, 1-acetoxy tridecyl, 1-acetoxy tetradecyl, 1-acetoxy pentadecyl, 1-acetoxy hexadecyl, 1-acetoxy heptadecyl, 1-acetoxy octadecyl, 1-acetoxy nonadecyl, 1-acetoxy eicosyl, 1-acetoxy henicosyl, 1-acetoxy docosyl, 1-acetoxy tricosyl, 1-acetoxy tetracosyl, 1-cyano methyl, 1-cyano ethyl, 1-cyano propyl, 1-cyano butyl, 1-cyano pentyl, 1-cyano hexyl, 1-cyano heptyl, 1-cyano octyl, 1-cyano nonyl, decyl, 1-cyano undecyl, 1-cyano dodecyl, 1-cyano tridecyl, 1-cyano tetradecyl, 1-cyano pentadecyl, 1-cyano hexadecyl, 1-cyano heptadecyl, 1-cyano octadecyl, 1-cyano nonadecyl, 1-cyano eicosyl, 1-cyano henicosyl, 1-cyano docosyl, 1-cyano tricosyl, 1-cyano tetracosyl, 2-cyano propyl, 2-cyano butyl, 2-cyano pentyl, 2-cyano hexyl, 2-cyano heptyl, 2-cyano octyl, 2-cyano nonyl, decyl, 2-cyano undecyl, 2-cyano dodecyl, 2-cyano tridecyl, 2-cyano tetradecyl, 2-cyano pentadecyl, 2-cyano hexadecyl, 2-cyano heptadecyl, 2-cyano octadecyl, 2-cyano nonadecyl, 2-cyano eicosyl, 2-cyano henicosyl, 2-cyano docosyl, 2-cyano tricosyl, 2-cyano tetracosyl, 1-thioyl methyl, 1-thioyl ethyl, 1-thioyl propyl, 1-thioyl butyl, 1-thioyl pentyl, 1-thioyl hexyl, 1-thioyl heptyl, 1-thioyl octyl, 1-thioyl nonyl, decyl, 1-thioyl undecyl, 1-thioyl dodecyl, 1-thioyl tridecyl, 1-thioyl tetradecyl, 1-thioyl pentadecyl, 1-thioyl hexadecyl, 1-thioyl heptadecyl, 1-thioyl octadecyl, 1-thioyl nonadecyl, 1-thioyl eicosyl, 1-thioyl henicosyl, 1-thioyl docosyl, 1-thioyl tricosyl and 1-thioyl tetracosyl.

In a preferred embodiment, the term alkenyl denotes unsubstituted, linear $C_2$-$C_{24}$ alkenyl which is preferably selected from the group consisting of 1-propenyl, 1-butenyl, 1-pentenyl, 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, more preferably selected from 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, 20-henicosenyl, 2-docosenyl, 6-tricosenyl and 2-tetracosenyl.

In a preferred embodiment, the unsubstituted branched $C_2$-$C_{24}$ alkenyl is selected from the group consisting of isopropenyl, iso-butenyl, neo-pentenyl, 2-ethyl-hexenyl, 2-propyl-heptenyl, 2-butyl-octenyl, 2-pentyl-nonenyl, 2-hexyl-decenyl, iso-hexenyl, iso-heptenyl, iso-octenyl, iso-nonenyl, iso-decenyl, iso-dodecenyl, iso-tetradecenyl, iso-hexadecenyl, iso-octadecenyl, iso-eicosenyl, 2-methyl tricosenyl, 2-ethyl docosenyl, 3-ethylhenicosenyl, 3-ethyl icosenyl, 4-propylhenicosenyl, 4-propylnonadecenyl, 6-butyldodecenyl, 5-ethylundedcenyl, 1,4-hexadienyl, 1,3-hexadienyl, 2,5-hexadienyl, 3,5-hexadienyl, 2,4-hexadienyl, 1,3,5-hexatrienyl, 1,3,6-heptatrienyl, 1,4,7-octatrienyl or 2-methyl-1,3,5hexatrienyl, 1,3,5,7-octatetraenyl, 1,3,5,8-nonatetraenyl, 1,4,7,10-undecatetraenyl, 2-ethyl-1,3,6,8-nonatetraenyl, 2-ethenyl-1,3,5,8-nonatetraenyl, 1,3,5,7,9-decapentaenyl, 1,4,6,8,10-undecapentaenyl, and 1,4,6,9,11-dodecapentaenyl.

In a preferred embodiment, the substituted, linear or branched, $C_2$-$C_{24}$ alkenyl refers to a branched or an linear unsaturated hydrocarbon group having $C_2$-$C_{24}$ carbon atoms substituted with functional groups selected from, hydroxy, alkoxy, C(=O)R, CN and SR; wherein R is hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl.

In a preferred embodiment the substituted, linear or branched, $C_2$-$C_{24}$ alkenyl refers to a branched or an linear unsaturated hydrocarbon group having $C_2$-$C_{24}$ carbon atoms substituted with functional groups selected from, hydroxy, alkoxy, C(=O)R, CN and SR; preferably selected from the group consisting of 2-hydroxy propenyl, 3-hydroxy butenyl, 3-hydroxy pentenyl, 5-hydroxy hexenyl, 7-hydroxy heptenyl, 3-hydroxy octenyl, 5-hydroxy nonenyl, decyl, 11-hydroxy undecenyl, 9-hydroxy dodecenyl, 6-hydroxy tridecenyl, 4-hydroxy tetradecenyl, 6-hydroxy pentadecenyl, 3-hydroxy hexadecenyl, 2-hydroxy heptadecenyl, 7-hydroxy octadecenyl, 6-hydroxy nonadecenyl, 4-hydroxy eicosenyl, 2-hydroxy henicosenyl, 3-hydroxy docosenyl, 2-hydroxytricosenyl, 23-hydroxytetracosenyl, 1-methoxy ethenyl, 2-methoxy propenyl, 4-methoxy butenyl, 3-methoxy pentenyl, 5-methoxy hexenyl, 2-methoxy heptenyl, 5-methoxy octenyl, 3-methoxy nonenyl, 6-methoxy undecenyl, 1-methoxy dodec-2-enyl, 1-methoxy tridec-5-enyl, 3-methoxy tetradic-5-enyl, 3-methoxy pentade-12-encyl, 10-methoxy hexadec-15-enyl, 12-methoxy heptadic-16-enyl, 1-methoxy octadec-3-enyl, 1-methoxy nonadec-2-enyl, 1-methoxy eicos-20-enyl, 1-methoxy henicos-2-enyl, 1-methoxy docos-4-enyl, 1-methoxy tricos-22-enyl, 1-methoxy tetracos-23-enyl, 2-methoxy prop-1-enyl, 2-methoxy but-1-enyl, 2-methoxy pent-4-enyl, 2-methoxy hex-2-enyl, 2-methoxy hept-3-enyl, 2-methoxy oct-7-enyl, 2-methoxy non-5-enyl, 2-methoxy undec-10-enyl, 2-methoxy dodec-4-enyl, 2-methoxy tridec-12-enyl, 2-methoxy tetradic-10-enyl, 2-methoxy pentadec-14-enyl, 2-methoxy hexadec-1-enyl, 2-methoxy heptadic-1-enyl, 2-methoxy octadic-12-enyl, 2-methoxy nonadec-10-enyl, 2-methoxy eicos-18-enyl, 2-methoxy henicos-2-enyl, 2-methoxy docos-3-enyl, 20-methoxy tricos-2-enyl, 21-methoxy tetracos-4-enyl, 1-acetoxy ethenyl, 1-acetoxy prop-1-enyl, 1-acetoxy but-2-enyl, 1-acetoxy pent-4-enyl, 1-acetoxy hex-2-enyl, 1-acetoxy hept-1-enyl, 1-acetoxy oct-7-enyl, 1-acetoxy non-2-enyl, 5-acetoxy dec-3-enyl, 1-acetoxy undec-10-enyl, 1-acetoxy dodec-2-enyl, 1-acetoxy tridec-12-enyl, 10-acetoxy tetradec-2-enyl, 15-acetoxy pentadec-2-enyl, 10-acetoxy hexadec-2-enyl, 11-acetoxy heptadec-1-enyl, 13-acetoxy octadec-2-enyl, 1-acetoxy nonadec-14-enyl, 20-acetoxy eicos-19-enyl, 1-acetoxy henicos-2-enyl, 1-acetoxy docos-10-enyl, 1-acetoxy tricos-22-enyl, 1-acetoxy tetracos-23-enyl, 1-cyano eth-1-enyl, 1-cyano prop-2-enyl, 1-cyano but-2-enyl, 1-cyano pent-3-enyl, 1-cyano hex-5-enyl, 1-cyano hept-6-enyl, 1-cyano oct-2-enyl, 1-cyano non-3-enyl, 11-cyano undec-2-enyl, 10-cyano dodec-2-enyl, 10-cyano tridec-12-enyl, 1-cyano tetradec-3-enyl, 1-cyano pentadec-14-enyl, 1-cyano hexadec-15-enyl, 1-cyano heptadec-2-enyl, 1-cyano octadec-3-enyl, 1-cyano nonadec-18-enyl, 1-cyano eicos-10-enyl, 1-cyano henicos-20-enyl, 15-cyano docos-3-enyl, 1-cyano tricos-20-enyl, 1-cyano tetracos-2-enyl, 2-cyano prop-2-enyl, 2-cyano but-1-enyl, 2-cyano pent-1-enyl, 2-cyano hex-3-enyl, 2-cyano hept-6-enyl, 2-cyano oct-1-enyl, 2-cyano non-8-enyl, 2-cyano undec-10-enyl, 2-cyano dodec-1-enyl, 2-cyano tridec-12-enyl, 2-cyano tetradec-10-enyl, 2-cyano pentadec-3-enyl, 2-cyano hexadec-2-enyl, 2-cyano heptadec-1-enyl, 2-cyano octadec-12-enyl, 2-cyano nonadec-15-enyl, 2-cyano eicos-1-enyl, 2-cyano henicos-5-enyl, 2-cyano docos-20-enyl, 2-cyano tricos-22-enyl, 2-cyano tetracos-20-enyl, 1-thionyl eth-1-enyl, 1-thionyl prop-2-enyl, 1-thionyl but-2-enyl, 1-thionyl pent-4-enyl, 1-thionyl hex-2-enyl, 1-thionyl hept-5-enyl, 1-thionyl oct-3-enyl, 1-thionyl non-5-enyl, 1-thionyl undec-10-enyl, 1-thionyl dodec-11-enyl, 1-thionyl tridec-2-enyl, 1-thionyl tetradec-4-enyl, 1-thionyl pentadec-5-enyl, 1-thionyl hexadec-3-enyl, 1-thionyl heptadec-2-enyl, 1-thionyl octadec-3-enyl, 1-thionyl nonadec-15-enyl, 1-thionyl eicos-18-enyl, 1-thionyl henicos-20-enyl, 1-thionyl docos-21-enyl, 1-thionyl tricos-20-enyl and 1-thionyl tetracos-22-enyl.

In a preferred embodiment, the substituted or unsubstituted $C_5$-$C_{24}$ cycloalkyl refers to a monocyclic and bicyclic 5 to 24 membered saturated cycloaliphatic radical. Representative examples of unsubstituted or branched $C_5$-$C_{24}$ monocyclic and bicyclic cycloalkyl include, but are not limited to, cyclopentyl, cyclohexyl, cycloheptyl, cyclooctyl, bicyclo[2.2.1]heptyl, and bicyclo[3.1.1]heptyl.

In another preferred embodiment, the $C_5$-$C_{24}$ monocyclic and bicyclic cycloalkyl can be further branched with one or more equal or different alkyl groups such as methyl, ethyl, n-propyl, iso-propyl, n-butyl, iso-butyl, n-pentyl, iso-pentyl, neo-pentyl etc. The representative examples of branched $C_3$-$C_{10}$ monocyclic and bicyclic cycloalkyl include, but are not limited to, methyl cyclohexyl and dimethyl cyclohexyl.

In a preferred embodiment, the unsubstituted or substituted $C_5$-$C_{24}$ cycloalkenyl refers to a monocyclic and bicyclic 5 to 24 membered unsaturated cycloaliphatic radical, which comprises one or more double bonds. Representative examples of $C_5$-$C_{24}$ cycloalkenyl include, but are not limited to, cyclopentenyl, cyclohexenyl, cycloheptenyl, cyclooctenyl, cyclononenyl or cyclodecenyl. These radicals can be branched with one or more equal or different alkyl radical, preferably with methyl, ethyl, n-propyl or iso-propyl. The representative examples of branched $C_5$-$C_{24}$ monocyclic and bicyclic cycloalkenyl include, but are not limited to, methyl cyclohexenyl and dimethyl cyclohexenyl.

In a preferred embodiment, the unsubstituted $C_6$-$C_{24}$ aryl may have more than one aromatic ring. The representative examples for substituted and unsubstituted $C_6$-$C_{24}$ aryl include phenyl, naphthyl, anthracenyl, tetraphenyl, phenalenyl and phenanthrenyl.

In a preferred embodiment, the arylalkyl refers to an aryl ring attached to an alkyl chain. The representative examples for the arylalkyl include, but are not limited to, 1-phenylmethyl, 1-phenylethyl, 1-phenylpropyl, 1-phenylbutyl, 1-methyl-1-phenyl-propyl, 3-phenylpropyl, 4-phenylbutyl, 3-phenylbutyl and 2-methyl-3-phenyl-propyl.

In a preferred embodiment, the substituted $C_6$-$C_{24}$ aryl refers to an aromatic ring having substitution at different positions. The $C_6$-$C_{24}$ aryl may have more than one aromatic ring. The representative examples for substituted and unsubstituted $C_6$-$C_{24}$ aryl include tolyl, xylyl, 2-hydroxyphenyl, 2,3-dihydroxyphenyl, 2-methoxy phenyl, 2-hydroxy-4-methoxyphenyl, 2,4-dimethoxyphenyl, 2-chlorophenyl, 2-chloro-4-hydroxyphenyl, 2-chloro-4-methoxy phenyl, 3-chloro-4-methoxyphenyl, 2-methyl-4-methoxy-6-chlorophenyl and 2-acetyl-4-hydroxyphenyl.

In a preferred embodiment, the $R_1$, $R_2$, $R_3$, $R_4$ and $R_5$ are independently C(=O)R. The representative example include C(=O)CH$_3$, C(=O)C$_2$H$_5$, C(=O)C$_3$H$_7$, C(=O)C$_4$H$_9$, C(=O)C$_4$H$_7$, C(=O)C$_6$H$_{11}$, C(=O)C$_6$H$_9$, C(=O)C$_9$H$_{19}$, C(=O)C$_{10}$H$_{19}$, C(=O)C$_{10}$H$_{21}$, C(=O)C$_{15}$H$_{31}$, C(=O)C$_{13}$H$_{27}$, C(=O)C$_{14}$H$_{29}$, C(=O)C$_{15}$H$_{31}$ and C(=O)C$_{20}$H$_{41}$.

In a preferred embodiment, the $R_1$, $R_2$, $R_3$, $R_4$ and $R_5$ are independently OR. The representative examples include OCH$_3$, OC$_2$H$_5$, OC$_3$H$_7$, OC$_4$H$_9$, OC$_4$H$_7$, OC$_5$H$_{11}$, OC$_6$H$_{11}$, OC$_6$H$_9$, OC$_7$H$_{15}$, OC$_8$H$_{17}$, OC$_9$H$_{19}$, OC$_{10}$H$_{19}$, OC$_{10}$H$_{21}$, OC$_{15}$H$_{31}$, OC$_{13}$H$_{27}$, OC$_{14}$H$_{29}$, OC$_{15}$H$_{31}$ and OC$_{20}$H$_{41}$.

In a preferred embodiment, the $R_1$, $R_2$, $R_3$, $R_4$ and $R_5$ are independently NRR', wherein R and R' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and $R_5$ are independently C(=O)NRR', wherein R and R' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and $R_5$ are independently SR, wherein R is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl.

In a preferred embodiment, the $R_1$, $R_2$, $R_3$, $R_4$ and R are independently S(=O)$_2$R, wherein R is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl.

In another preferred embodiment, the alkali metals are selected from the group consisting of lithium, sodium, potassium and caesium, more preferably selected from the group consisting of lithium, sodium and potassium, most preferably selected from the group consisting of sodium and potassium.

In a preferred embodiment, $R_6$ is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, and C(=O)R; more preferably, $R_6$ is selected from the group consisting of hydrogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, and C(=O)R. Most preferably, $R_6$ is selected from the group consisting of hydrogen, substituted or unsubstituted, linear or branched $C_1$-$C_{24}$ alkyl, substituted and C(=O)R; and in particular preferably, $R_6$ is selected from the group consisting of hydrogen, substituted or unsubstituted, linear or branched $C_1$-$C_{24}$ alkyl and substituted.

In another preferred embodiment, $R_7$, $R_8$ and $R_9$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OC(=O)R, CN, SR, S(=O)$_2$R, S(=O)$_2$OH and S(=O)$_2$OM, wherein M is an alkali metal, R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen;

more preferably $R_7$, $R_8$ and $R_9$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, C(=O)R, OR, NRR', C(=O)NRR', OC(=O)R and CN; R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl and substituted or unsubstituted $C_7$-$C_{24}$ arylalkyl, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s); with the proviso that when $R_7$, $R_8$ or $R_9$ is NRR', R and R' are not both hydrogen;

even more preferably $R_7$, $R_8$ and $R_9$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, C(=O) R, OR, NRR', C(=O)NRR', OC(=O)R, CN, R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl; most preferably $R_7$, $R_8$ and $R_9$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, OR, OC(=O)R, R is selected from the group consisting of hydrogen and substituted or unsubstituted, linear or branched $C_1$-$C_{24}$ alkyl;

and in particular preferably $R_7$, $R_8$ and $R_9$ are independently selected from the group consisting of hydrogen, halogen, substituted or unsubstituted, linear or branched $C_1$-$C_{24}$ alkyl, OR, OC(=O)R, R is selected from the group consisting of hydrogen and substituted or unsubstituted, linear or branched $C_1$-$C_{24}$ alkyl.

In another preferred embodiment, Y is selected from the group consisting of hydrogen, halogen, O, —NR", or S, wherein R" is hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl; when Y is a hydrogen or halogen then $R_6$ is absent; more preferably, Y is selected from the group consisting of hydrogen, halogen, O; when Y is a hydrogen or halogen then $R_6$ is absent; most preferably, Y is selected from the group consisting of hydrogen and O; when Y is a hydrogen then $R_6$ is absent.

Step i)

In another preferred embodiment, the step i) of the presently claimed invention comprises reacting at least one compound of formula (C)

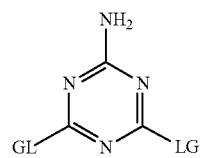

formula (C)

wherein LG is halogen, O—S(=O)$_2$CF$_3$ or O—S(=O)$_2$CH$_3$;

with at least one compound of formula (B1)

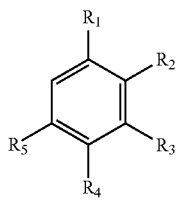

formula (B1)

wherein $R_1$, $R_2$, $R_3$, $R_4$ and $R_5$ are defined as above;
in the presence of at least one acid to obtain a compound of formula (D)

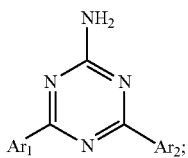

formula (D)

wherein $Ar_1$ and $Ar_2$ are defined as above;

In a preferred embodiment, the compound of formula (C) is selected from the group consisting of 4,6-dichloro-1,3,5-triazin-2-amine, 4,6-dibromo-1,3,5-triazin-2-amine, 4,6-diiodo-1,3,5-triazin-2-amine, 6-amino-1,3,5-triazine-2,4-diyl dimethanesulfonate, and 6-amino-1,3,5-triazine-2,4-diyl bis(trifluoromethanesulfonate); more preferably the compound of formula (C) is selected from the group consisting of 4,6-dichloro-1,3,5-triazin-2-amine and 4,6-dibromo-1,3,5-triazin-2-amine.

In another preferred embodiment, the at least one compound of formula (B1) includes benzene, toluene, xylene, cresol, biphenyl, 2,3-dimethylphenol, 2-methylbenzene-1,3-diol, 3-(methoxy)-2-methylphenol, 3-(ethoxy)-2-methylphenol, 3-(propoxy)-2-methylphenol, 3-(butoxy)-2-methylphenol, 3-(pentoxy)-2-methylphenol, 3-(hexyloxy)-2-methylphenol, 3-((2-ethylhexyl)oxy)-2-methylphenol, 3-((2-ethylhexyl)oxy)phenol, 3-(hexyloxy)phenol, 1,3-bis(methoxy)benzene, 1,3-bis(ethoxy)benzene, 1,3-bis(propoxy)benzene, 1,3-bis(butoxy)benzene, 1,3-bis(pentoxy)benzene and 1,3-bis(hexoxy)benzene.

In another preferred embodiment, the at least one acid used in step (i) is selected from the group consisting of inorganic acids, Lewis acids, and organic acids.

In another preferred embodiment, the at least one inorganic acid is selected from the group consisting of sulfuric acid, hydrochloric acid, phosphoric acid ($H_3PO_4$), phosphorous acid ($H_3PO_3$), phosphinic acid ($H_3PO_2$), perchloric acid, nitric acid, nitrous acid, sulphurous acid, chloric acid, chlorous acid and hypochlorous acid; more preferably the at least one inorganic acid is hydrochloric acid.

In another preferred embodiment, the at least one Lewis acid is selected from the group consisting of $AsX_3$, $GaX_3$, $BX_3$, $BX_3·(C_2H_5)_2O$, $BX_3·S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, $Li(acetate)$, $Zr(acetylacetonate)_4$, $Si(acetate)_4$, $K(acetate)$, $Na(acetate)$, $Cs(acetate)$, $Rb(acetate)$, $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, $Ag(acetate)$, $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri-fluoromethanesulfonate)_2$ and $Cu(tosylate)_2$; more preferably the Lewis acid is selected from the group consisting of $AsX_3$, $GaX_3$, $BX_3$, $BX_3·(C_2H_5)_2O$, $BX_3·S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; most preferably selected from the group consisting of $BX_3$, $BX_3·(C_2H_5)_2O$, $BX_3·S(CH_3)_2$, $AlX_3$, $(C_2H_5)_2AlX$, $TiX_2$, $TiX_4$ whereby X in each case denotes F, Cl, Br, $S(=O)_3$, $CF_3$—$S(=O)_2O$, $CH_3$—$S(=O)_2O$, or I; particularly preferably, selected from the group consisting of $BX_3$, $AlX_3$, $(C_2H_5)_2AlX$, whereby X in each case denotes F, Cl, Br, $CF_3$—$S(=O)_2O$, $CH_3$—$S(=O)_2O$, or I.

In another preferred embodiment, the at least one Lewis acid is selected from the group consisting of $BX_3$, $BX_3·(C_2H_5)_2O$, $BX_3·S(CH_3)_2$, $AlX_3$, $ZnX_2$, $FeX_3$ and $TiX_4$, whereby X in each case denotes F, Cl, or Br.

In another preferred embodiment, the at least one organic acid is selected from the group consisting of organic carboxylic acid and organic sulfonic acid.

In another preferred embodiment, the at least one organic carboxylic acid is selected from the group consisting of acetic acid, formic acid, propionic acid, butanoic acid, benzoic acid, phthalic acid, oxalic acid, malonic acid, succinic acid, glutaric acid, adipic acid, lactic acid, citric acid, uric acid and malic acid; more preferably the at least one organic carboxylic acid is selected from the group consisting of acetic acid, formic acid, propionic acid, butanoic acid and benzoic acid; most preferably the at least one organic carboxylic acid is selected from the group consisting of acetic acid and formic acid.

In a preferred embodiment, the organic sulfonic acid is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid, more preferably the organic sulfonic acid is selected from the group consisting of methanesulfonic acid, trifluoromethanesulfonic acid, benzenesulfonic acid and p-toluenesulfonic acid, even more preferably the organic sulfonic acid is selected from the group consisting of methanesulfonic acid, trifluoromethanesulfonic acid and p-toluenesulfonic acid.

In another preferred embodiment, the molar ratio of the at least one acid to the at least one compound of formula (C) in step (i) is in the range of 1:10 to 10:1, more preferably in the range of 1:5 to 5:1, most preferably in the range of 1:3 to 3:1.

In another preferred embodiment, the molar ratio of the at least one compound of formula (B1) to the at least one compound of formula (C) in step (i) is in the range of 1:1.0 to 5:1.0, more preferably in the range of 1:1 to 3:1, and most preferably in the range of 1:1 to 2:1.

In another preferred embodiment, the at least one compound of formula (C) and the at least one compound of formula (B1) in step (i) are reacted in the presence of at least one solvent.

In another preferred embodiment, the at least one solvent used in step (i) is selected from the group consisting of aliphatic hydrocarbons, aromatic hydrocarbons, aliphatic acyclic ether, aliphatic cyclic ether and carbon disulfide.

In another preferred embodiment, the aliphatic hydrocarbons are selected from the group consisting of nitroalkanes, heptane, cyclohexane, dichloromethane, chloroform, carbon tetrachloride, dibromomethane, bromoform, iodomethane, diiodomethane, dichloroethane, 1,1,2,2-tetrachloroethane, acetone, acetic acid, hexane; more preferably the aliphatic hydrocarbons are selected from the group consisting of dichloroethane, 1,1,2,2-tetrachloroethane, dimethylsulfoxide and tetramethylene sulfone.

In another preferred embodiment, the aromatic hydrocarbons are selected from the group consisting of benzene, toluene, xylene, nitrobenzene, dinitrobenzene, chlorobenzene, dichlorobenzene, trichlorobenzene, fluorobenzene, difluoro benzene, trifluoro benzene, bromobenzene, dibromo benzene, tribromo benzene; more preferably the aromatic hydrocarbons are selected from the group consisting of benzene, nitrobenzene, dinitrobenzene, and toluene.

In another preferred embodiment, the aliphatic acyclic ether and the aliphatic cyclic ether are selected from the group consisting of di tert-butyl ether, dioxane and tetrahydrofuran.

In another preferred embodiment, in step (i) the molar concentration of the at least one compound of formula (C) in the at least one solvent is in the range of 0.5 M to 8.0 M, more preferably is in the range of 1.0 M to 6.0 M, even more preferably is in the range of 1.0 M to 5.0 M, most preferably is in the range of 1.0 M to 3.0 M, and in particular preferably is in the range of 1.0 M to 2.0 M.

In another preferred embodiment, in step (i) the molar concentration of the at least one compound of formula (B1) in the at least one solvent is in the range of 0.5 M to 8.0 M, more preferably is in the range of 1.0 M to 6.0 M, even more preferably is in the range of 1.0 M to 5.0 M, most preferably is in the range of 1.0 M to 3.0 M, and in particular preferably is in the range of 1.0 M to 2.0 M.

In another preferred embodiment, in step (i) the at least one compound of formula (C) and the at least one compound of formula (B1) are reacted at a temperature in the range of 0° C. to 250° C., more preferably in the temperature in the range of 30° C. to 200° C., most preferably temperature in the range of 50° C. to 150° C., and in particular preferably temperature in the range of 80° C. to 120° C.

In a preferred embodiment, in step (i) the at least one compound of formula (C) and the at least one compound of formula (B1) are reacted for a period in the range of 30 minutes to 24 hours, more preferably reacted for a period in the range of 30 minutes to 15 hours, most preferably reacted for a period in the range of 1 hour to 10 hours, and in particular preferably reacted for a period in the range of 1 hour to 5 hours.

The compound of formula (D) formed in the step (i) can be isolated by any method known in the art selected from the group consisting of chemical separation, acid-base neutralization, distillation, evaporation, column chromatography, filtration, concentration, crystallization and re-crystallization or a combination thereof. A person skilled in the art is familiar with such techniques.

Step ii)

In a preferred embodiment, the step ii) of the presently claimed invention comprises reacting the compound of formula (D) obtained according to step i) with at least one metal hydroxide to obtain a compound of formula (E)

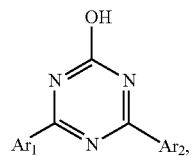

formula (E)

wherein $Ar_1$ and $Ar_2$ are defined as above.

In another preferred embodiment, the compound of formula (D) is selected from the group consisting of 2-(4-amino-6-(2,4-dipropoxyphenyl)-1,3,5-triazin-2-yl)-5-propoxyphenol, 2-(4-amino-6-(2,4-dipropoxyphenyl)-1,3,5-triazin-2-yl)-5-propoxyphenol, 2-(4-amino-6-(2,4-dibutoxyphenyl)-1,3,5-triazin-2-yl)-5-butoxyphenol, 2-(4-amino-6-(2,4-dibutoxyphenyl)-1,3,5-triazin-2-yl)-5-butoxyphenol, 2-(4-amino-6-(2,4-dipentoxyphenyl)-1,3,5-triazin-2-yl)-5-pentoxyphenol, 2-(4-amino-6-(2,4-dipentoxyphenyl)-1,3,5-triazin-2-yl)-5-pentoxyphenol, 2-(4-amino-6-(2,4-dihexoxyphenyl)-1,3,5-triazin-2-yl)-5-hexoxyphenol, 2-(4-amino-6-(2,4-dihexoxyphenyl)-1,3,5-triazin-2-yl)-5-hexoxyphenol, 2-(4-amino-6-(2,4-diheptoxyphenyl)-1,3,5-triazin-2-yl)-5-heptoxyphenol, 2-(4-amino-6-(2,4-diheptoxyphenyl)-1,3,5-triazin-2-yl)-5-heptoxyphenol, 4,6-di([1,1'-biphenyl]-4-yl)-1,3,5-triazin-2-amine, 2,2'-(((6-amino-1,3,5-triazine-2,4-diyl)bis(3-hydroxy-4,1-phenylene))bis(oxy))dipropionic acid, dimethyl 2,2'-(((6-amino-1,3,5-triazine-2,4-diyl)bis(3-hydroxy-4,1-phenylene))bis(oxy))dipropionate, dinonyl 2,2'-(((6-amino-1,3,5-triazine-2,4-diyl)bis(3-hydroxy-4,1-phenylene))bis(oxy))dipropionate, dioctyl 2,2'-(((6-amino-1,3,5-triazine-2,4-diyl)bis(3-hydroxy-4,1-phenylene))bis(oxy))dipropionate, didecyl 2,2'-(((6-amino-1,3,5-triazine-2,4-diyl)bis(3-hydroxy-4,1-phenylene))bis(oxy))dipropionate, didodecyl 2,2'-(((6-amino-1,3,5-triazine-2,4-diyl)bis(3-hydroxy-4,1-phenylene))bis(oxy))dipropionate, diisooctyl 2,2'-(((6-amino-1,3,5-triazine-2,4-diyl)bis(3-hydroxy-4,1-phenylene))bis(oxy))dipropionate, diheptyl 2,2'-(((6-amino-1,3,5-triazine-2,4-diyl)bis(3-hydroxy-4,1-phenylene))bis(oxy))dipropionate, dihexyl 2,2'-(((6-amino-1,3,5-triazine-2,4-diyl)bis(3-hydroxy-4,1-phenylene))bis(oxy))dipropionate, dipentyl 2,2'-(((6-amino-1,3,5-triazine-2,4-diyl)bis(3-hydroxy-4,1-phenylene))bis(oxy))dipropionate, 4,4'-(6-amino-1,3,5-triazine-2,4-diyl)bis(benzene-1,3-diol), 4,6-bis(2,4-dimethylphenyl)-1,3,5-triazin-2-amine, and 4,6-diphenyl-1,3,5-triazin-2-amine.

In another preferred embodiment, the at least one metal hydroxide is selected from the group consisting of NaOH, KOH, LiOH, Cs(OH), Be(OH)$_2$, Mg(OH)$_2$, Ca(OH)$_2$, Sr(OH)$_2$, Ba(OH)$_2$, and Al(OH)$_3$; more preferably the metal hydroxides is selected from the group consisting of NaOH, KOH and LiOH; and most preferably the metal hydroxide is NaOH or KOH.

In another preferred embodiment, the reaction in step ii) is carried out in the presence of at least one solvent.

In another preferred embodiment, the reaction in step ii) is carried out in the presence of at least one organic solvent selected from the group consisting of polar protic solvents and polar aprotic solvents.

In another preferred embodiment, the polar protic solvent is selected from the group consisting of water, alcohol, nitromethane, formic acid and acetic acid.

In another preferred embodiment, the alcohol is selected from the group consisting of methanol, ethanol, propanol, butanol, t-butanol, (2-butoxy)ethanol, ethylene glycol and polyethylene glycol; more preferably the alcohol is (2-butoxy)ethanol.

In another preferred embodiment, the polar aprotic solvent is selected from the group consisting of dimethyl sulfoxide, dimethyl formamide, dimethyl acetamide, anisole, N-methyl pyrrolidone, tetrahydrofuran, ethyl acetate, acetone, acetonitrile, propylene carbonate and sulfolane.

In another preferred embodiment, the reaction in step ii) is carried out at a temperature in the range of 0 to 150° C.; more preferably in the range of 30 to 150° C.; even more preferably in the range of 50 to 120° C.; and most preferably in the range of 50 to 100° C.

In another preferred embodiment, in step (ii) the molar ratio of the at least one metal hydroxide to the at least one compound of formula (D) is in in the range of 1:1 to 10:1; more preferably is in in the range of 1:1 to 6:1; most preferably is in in the range of 1:1 to 4:1; and in particular preferably is in in the range of 1:1 to 2:1.

The compound of formula (E) formed in the step (ii) can be isolated by any method known in the art selected from the group consisting of chemical separation, acid-base neutralization, distillation, evaporation, column chromatography, filtration, concentration, crystallization and re-crystallization or a combination thereof. A person skilled in the art is familiar with such techniques.

Step iii)

In a preferred embodiment, the step iii) of the presently claimed invention comprises reacting the compound of formula (E) obtained according to step ii) with at least one halogenating reagent to obtain a compound of formula (F)

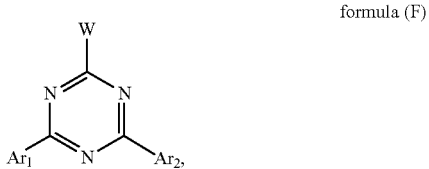

formula (F)

wherein $Ar_1$ and $Ar_2$ are defined as above, and

W is selected from the group consisting of F, Cl, and Br.

In a preferred embodiment, the compound of formula (E) is selected from the group consisting of 2-(4-hydroxy-6-(2,4-dipropoxyphenyl)-1,3,5-triazin-2-yl)-5-propoxyphenol, 2-(4-hydroxy-6-(2,4-dipropoxyphenyl)-1,3,5-triazin-2-yl)-5-propoxyphenol, 2-(4-hydroxy-6-(2,4-dibutoxyphenyl)-1,3,5-triazin-2-yl)-5-butoxyphenol, 2-(4-hydroxy-6-(2,4-dibutoxyphenyl)-1,3,5-triazin-2-yl)-5-butoxyphenol, 2-(4-hydroxy-6-(2,4-dipentoxyphenyl)-1,3,5-triazin-2-yl)-5-pentoxyphenol, 2-(4-hydroxy-6-(2,4-dipentoxyphenyl)-1,3,5-triazin-2-yl)-5-pentoxyphenol, 2-(4-hydroxy-6-(2,4-dihexoxyphenyl)-1,3,5-triazin-2-yl)-5-hexoxyphenol, 2-(4-hydroxy-6-(2,4-dihexoxyphenyl)-1,3,5-triazin-2-yl)-5-hexoxyphenol, 2-(4-hydroxy-6-(2,4-diheptoxyphenyl)-1,3,5-triazin-2-yl)-5-heptoxyphenol, 2-(4-hydroxy-6-(2,4-diheptoxyphenyl)-1,3,5-triazin-2-yl)-5-heptoxyphenol, 4,6-di([1,1'-biphenyl]-4-yl)-1,3,5-triazin-2-ol, 2,2'-(((6-hydroxy-1,3,5-triazine-2,4-diyl)bis(3-hydroxy-4,1-phenylene))bis(oxy))dipropionic acid, dimethyl 2,2'-(((6-hydroxy-1,3,5-triazine-2,4-diyl)bis(3-hydroxy-4,1-phenylene))bis(oxy))dipropionate, dinonyl 2,2'-(((6-hydroxy-1,3,5-triazine-2,4-diyl)bis(3-hydroxy-4,1-phenylene))bis(oxy))dipropionate, dioctyl 2,2'-(((6-hydroxy-1,3,5-triazine-2,4-diyl)bis(3-hydroxy-4,1-phenylene))bis(oxy))dipropionate, didecyl 2,2'-(((6-hydroxy-1,3,5-triazine-2,4-diyl)bis(3-hydroxy-4,1-phenylene))bis(oxy))dipropionate, didodecyl 2,2'-(((6-hydroxy-1,3,5-triazine-2,4-diyl)bis(3-hydroxy-4,1-phenylene))bis(oxy))dipropionate, diisooctyl 2,2'-(((6-hydroxy-1,3,5-triazine-2,4-diyl)bis(3-hydroxy-4,1-phenylene))bis(oxy))dipropionate, diheptyl 2,2'-(((6-hydroxy-1,3,5-triazine-2,4-diyl)bis(3-hydroxy-4,1-phenylene))bis(oxy))dipropionate, dihexyl 2,2'-(((6-hydroxy-1,3,5-triazine-2,4-diyl)bis(3-hydroxy-4,1-phenylene))bis(oxy))dipropionate, dipentyl 2,2'-(((6-hydroxy-1,3,5-triazine-2,4-diyl)bis(3-hydroxy-4,1-phenylene))bis(oxy))dipropionate, 4,4'-(6-hydroxy-1,3,5-triazine-2,4-diyl)bis(benzene-1,3-diol), 4,6-bis(2,4-dimethylphenyl)-1,3,5-triazin-2-ol, 4,6-bis[4-(2-ethylhexyloxy)-2-hydroxy-phenyl]-1,3,5-triazin-2-ol, 4,6-bis(4-butoxy-2-hydroxy-phenyl)-1,3,5-triazin-2-ol, octyl 2-[3-hydroxy-4-[4-hydroxy-6-[2-hydroxy-4-(1-methyl-2-octoxy-2-oxo-ethoxy)phenyl]-1,3,5-triazin-2-yl]phenoxy] propanoate and 4,6-diphenyl-1,3,5-triazin-2-ol.

In a preferred embodiment, in step iii) the at least one halogenating reagent is selected from the group consisting of thionyl chloride, thionyl bromide, phosphorus pentachloride, phosphorous trichloride and phosphorus oxychloride, more preferably the at least one halogenating agent is selected from the group consisting of thionyl chloride, phosphorus pentachloride, and phosphorous trichloride; and most preferably the at least one halogenating agent is thionyl chloride.

In another preferred embodiment, the reaction in step iii) is carried out in the presence of at least one solvent selected from the group consisting of N,N-dimethyl formamide, N-methylpyrrolidone, toluene, xylene, hexane, heptane, 1,2-dichloroethene and 1,1,2,2-tetrachloroethene.

In another preferred embodiment, in step iii) the molar ratio of the at least one halogenating agent to the at least one compound of formula (E) is in in the range of 1:1 to 10:1; more preferably is in in the range of 1:1 to 6:1; most preferably is in in the range of 1:1 to 4:1; and in particular preferably is in in the range of 1:1 to 2:1.

In another preferred embodiment, the reaction in step iii) is carried out at a temperature in the range of 0 to 150° C.; more preferably in the range of 30 to 150° C.; even more preferably in the range of 30 to 120° C.; and most preferably in the range of 30 to 100° C.

The compound of formula (F) formed in the step (iii) can be isolated by any method known in the art selected from the group consisting of chemical separation, acid-base neutralization, distillation, evaporation, column chromatography, filtration, concentration, crystallization and re-crystallization or a combination thereof. A person skilled in the art is familiar with such techniques.

Step iv)

In a preferred embodiment, step iv) of the presently claimed invention comprises reacting at least one compound of formula (F) obtained according to step iii) and at least one compound of formula (G),

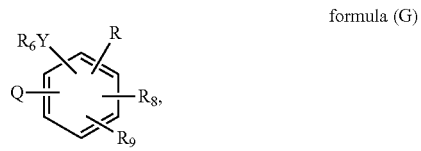

formula (G)

wherein Y, Q, R$_6$, R$_7$, R$_8$ and R$_9$ are defined as above, in the presence of an at least one acid to obtain a compound of formula (A).

In another preferred embodiment, the compound of formula (F) is selected from the group consisting of 2-(4-chloro-6-(2,4-dipropoxyphenyl)-1,3,5-triazin-2-yl)-5-propoxyphenol, 2-(4-bromo-6-(2,4-dipropoxyphenyl)-1,3,5-triazin-2-yl)-5-propoxyphenol, 2-(4-fluoro-6-(2,4-dipropoxyphenyl)-1,3,5-triazin-2-yl)-5-propoxyphenol, 2-(4-chloro-6-(2,4-dibutoxyphenyl)-1,3,5-triazin-2-yl)-5-butoxyphenol, 2-(4-bromo-6-(2,4-dibutoxyphenyl)-1,3,5-triazin-2-yl)-5-butoxyphenol, 2-(4-fluoro-6-(2,4-dibutoxyphenyl)-1,3,5-triazin-2-yl)-5-butoxyphenol, 2-(4-chloro-6-(2,4-dipentoxyphenyl)-1,3,5-triazin-2-yl)-5-pentoxyphenol, 2-(4-bromo-6-(2,4-dipentoxyphenyl)-1,3,5-triazin-2-yl)-5-pentoxyphenol, 2-(4-fluoro-6-(2,4-dipentoxyphenyl)-1,3,5-triazin-2-yl)-5-pentoxyphenol, 2-(4-chloro-6-(2,4-dihexoxyphenyl)-1,3,5-triazin-2-yl)-5-hexoxyphenol, 2-(4-bromo-6-(2,4-dihexoxyphenyl)-1,3,5-triazin-2-yl)-5-hexoxyphenol, 2-(4-chloro-6-(2,4-diheptoxyphenyl)-1,3,5-triazin-2-yl)-5-heptoxyphenol, 2-(4-bromo-6-(2,4-diheptoxyphenyl)-1,3,5-triazin-2-yl)-5-heptoxyphenol, 2,4-di([1,1'-biphenyl]-4-yl)-6-chloro-1,3,5-triazine, 2,4-di([1,1'-biphenyl]-4-yl)-6-bromo-1,3,5-triazine, 2,4-di([1,1'-biphenyl]-4-yl)-6-fluoro-1,3,5-triazine, 2,2'-(((6-chloro-1,3,5-triazine-2,4-diyl)bis(3-hydroxy-4,1-phenylene))bis(oxy))dipropionic acid, 2,2'-(((6-bromo-1,3,5-triazine-2,4-diyl)bis(3-hydroxy-4,1-phenylene))bis(oxy))dipropionic acid, dimethyl-2,2'-(((6-bromo-1,3,5-triazine-2,4-diyl)bis(3-hydroxy-4,1-phenylene))bis(oxy))dipropionate, dimethyl-2,2'-(((6-chloro-1,3,5-triazine-2,4-diyl)bis(3-hydroxy-4,1-phenylene))bis(oxy))dipropionate, dinonyl 2,2'-(((6-bromo-1,3,5-triazine-2,4-diyl)bis(3-hydroxy-4,1-phenylene))bis(oxy))dipropionate, dinonyl 2,2'-(((6-chloro-1,3,5-triazine-2,4-diyl)bis(3-hydroxy-4,1-phenylene))bis(oxy))dipropionate, dioctyl 2,2'-(((6-bromo-1,3,5-triazine-2,4-diyl)bis(3-hydroxy-4,1-phenylene))bis(oxy))dipropionate, didecyl 2,2'-(((6-chloro-1,3,5-triazine-2,4-diyl)bis(3-hydroxy-4,1-phenylene))bis(oxy))dipropionate, didodecyl 2,2'-(((6-bromo-1,3,5-triazine-2,4-diyl)bis(3-hydroxy-4,1-phenylene))bis(oxy))dipropionate, diisooctyl 2,2'-(((6-chloro-1,3,5-triazine-2,4-diyl)bis(3-hydroxy-4,1-phenylene))bis(oxy))dipropionate, diheptyl 2,2'-(((6-bromo-1,3,5-triazine-2,4-diyl)bis(3-hydroxy-4,1-phenylene))bis(oxy))dipropionate, dihexyl 2,2'-(((6-chloro-1,3,5-triazine-2,4-diyl)bis(3-hydroxy-4,1-phenylene))bis(oxy))dipropionate, dipentyl 2,2'-(((6-bromo-1,3,5-triazine-2,4-diyl)bis(3-hydroxy-4,1-phenylene))bis(oxy))dipropionate, 4,4'-(6-chloro-1,3,5-triazine-2,4-diyl)bis(benzene-1,3-diol), 2-chloro-4,6-bis(2,4-dimethylphenyl)-1,3,5-triazine, 2-[4,6-bis(2,4-dimethylphenyl)-1,3,5-triazin-2-yl]-5-chloro-phenol, 2-[4,6-bis(2,4-dimethylphenyl)-1,3,5-triazin-2-yl]-5-bromo-phenol, 2-[4,6-bis(2,4-dimethylphenyl)-1,3,5-triazin-2-yl]-5-fluoro-phenol, 5-chloro-2-(4,6-diphenyl-1,3,5-triazin-2-yl)phenol, 5-bromo-2-(4,6-diphenyl-1,3,5-triazin-2-yl)phenol, 5-fluoro-2-(4,6-diphenyl-1,3,5-triazin-2-yl)phenol, 2-[4-(4-bromophenyl)-6-[4-(2-ethylhexoxy)-2-hydroxy-phenyl]-1,3,5-triazin-2-yl]-5-(2-ethylhexoxy)phenol, 2-[4-(4-fluorophenyl)-6-[4-(2-ethylhexoxy)-2-hydroxy-phenyl]-1,3,5-triazin-2-yl]-5-(2-ethylhexoxy)phenol, 2-[4-(4-chlorophenyl)-6-[4-(2-ethylhexoxy)-2-hydroxy-phenyl]-1,3,5-triazin-2-yl]-5-(2-ethylhexoxy)phenol, 5-butoxy-2-[4-(4-butoxy-2-hydroxy-phenyl)-6-chloro-1,3,5-triazin-2-yl]phenol, 5-butoxy-2-[4-(4-butoxy-2-hydroxy-phenyl)-6-bromo-1,3,5-triazin-2-yl]phenol, 5-butoxy-2-[4-(4-butoxy-2-hydroxy-phenyl)-6-fluoro-1,3,5-triazin-2-yl]phenol, and 2-bromo-4,6-diphenyl-1,3,5-triazine.

In a preferred embodiment, the compound of formula (G) is selected from the group consisting of phenol, o-cresol, m-cresol, hydroquinone, 2,5-dimethylphenol, 2,4-dimethylphenol, 2,3-dimethylphenol, 2,3,5-trimethylphenol, 2,3,4-trimethylphenol, 3,4,5-trimethylphenol, 1-methoxy-2,3,5-trimethylbenzene, 1-methoxy-2-methylbenzene, 1-methoxy-3-methylbenzene, 1-methoxy-4-methylbenzene, 1-methoxy-2,3-dimethylbenzene, 1-methoxy-2,4-dimethylbenzene, 1-methoxy-2,5-dimethylbenzene, 1-methoxy-2,6-dimethylbenzene, 1-methoxy-3,4-dimethylbenzene, 1-methoxy-3,5-dimethylbenzene, 1-methoxy-3,6-dimethylbenzene, 1-(ethoxy)-2-methylbenzene, 1-(propoxy)-2-methylbenzene, 1-(butoxy)-2-methylbenzene, 1-(pentoxy)-2-methylbenzene, 1-(hexyloxy)-2-methylbenzene, 1-(heptyloxy)-2-methylbenzene, 1-(octyloxy)-2-methylbenzene, 1-(nonyloxy)-2-methylbenzene, 1-(decyloxy)-2-methylbenzene, 1-(undecyloxy)-2-methylbenzene, 1-(dodecyloxy)-2-methylbenzene, 1-(tridecyloxy)-2-methylbenzene, 1-(tetradecyloxy)-2-methylbenzene, 1-(pentadecyloxy)-2-methylbenzene, 1-(hexadecyloxy)-2-methylbenzene, 1-(heptadecyloxy)-2-methylbenzene, 1-(octadecyloxy)-2-methylbenzene, 1-(nonadecyloxy)-2-methylbenzene, 1-(icosyloxy)-2-methylbenzene, 1-(henicosyloxy)-2-methylbenzene, 1-(docosyloxy)-2-methylbenzene, 1-(methoxy)-3-methylbenzene, 1-(ethoxy)-3-methylbenzene, 1-(propoxy)-3-methylbenzene, 1-(butoxy)-3-methylbenzene, 1-(pentoxy)-3-methylbenzene, 1-(hexyloxy)-3-methylbenzene, 1-(heptyloxy)-3-methylbenzene, 1-(octyloxy)-3-methylbenzene, 1-(nonyloxy)-3-methylbenzene, 1-(decyloxy)-3-methylbenzene, 1-(undecyloxy)-3-methylbenzene, 1-(dodecyloxy)-3-methylbenzene, 1-(tridecyloxy)-3-methylbenzene, 1-(tetradecyloxy)-3-methylbenzene, 1-(pentadecyloxy)-3-methylbenzene, 1-(hexadecyloxy)-3-methylbenzene, 1-(heptadecyloxy)-3-methylbenzene, 1-(octadecyloxy)-3-methylbenzene, 1-(nonadecyloxy)-3-methylbenzene, 1-(icosyloxy)-3-methylbenzene, 1-(henicosyloxy)-3-methylbenzene, 1-(docosyloxy)-3-methylbenzene, 1-(methoxy)-4-methylbenzene, 1-(ethoxy)-4-methylbenzene, 1-(propoxy)-4-methylbenzene, 1-(butoxy)-4-methylbenzene, 1-(pentoxy)-4-methylbenzene, 1-(hexyloxy)-4-methylbenzene, 1-(heptyloxy)-4-methylbenzene, 1-(octyloxy)-4-methylbenzene, 1-(nonyloxy)-4-methylbenzene, 1-(decyloxy)-4-methylbenzene, 1-(undecyloxy)-4-methylbenzene, 1-(dodecyloxy)-4-methylbenzene, 1-(tridecyloxy)-4-methylbenzene, 1-(tetradecyloxy)-4-methylbenzene, 1-(pentadecyloxy)-4-methylbenzene, 1-(hexadecyloxy)-4-methylbenzene, 1-(heptadecyloxy)-4-methylbenzene, 1-(octadecyloxy)-4-methylbenzene, 1-(nonadecyloxy)-4-methylbenzene, 1-(icosyloxy)-4-methylbenzene, 1-(henicosyloxy)-4-methylbenzene, 1-(docosyloxy)-4-methylbenzene, 1-methyl-2-(vinyloxy)benzene, 1-methyl-2-(prop-1-en-1-yloxy)benzene, 1-(but-1-en-1-yloxy)-2-methylbenzene, 1-methyl-2-(pent-1-en-1-yloxy)benzene, 1-(hex-1-en-1-yloxy)-2-methylbenzene, 1-(hept-1-en-1-yloxy)-2-methylbenzene, 1-(oct-1-en-1-yloxy)-2-methylbenzene, 1-(non-1-en-1-yloxy)-2-methylbenzene, 1-(dec-1-en-1-yloxy)-2-methylbenzene, 1-(undec-1-en-1-yloxy)-2-methylbenzene, 1-(dodec-1-en-1-yloxy)-2-methylbenzene, 1-(tridec-1-en-1-yloxy)-2-methylbenzene, 1-(tetradec-1-en-1-yloxy)-2-methylbenzene, 1-(pentadec-1-en-1-yloxy)-2-methylbenzene, 1-(hexadec-1-en-1-yloxy)-2-methylbenzene, 1-(heptadec-1-en-1-yloxy)-2-methylbenzene, 1-(octadec-1-en-1-yloxy)-2-methylbenzene, 1-(nonadec-1-en-1-yloxy)-2-methylbenzene, 1-(icos-1-en-1-yloxy)-2-methylbenzene, 1-(henicos-1-en-1-yloxy)-2-methylbenzene, 1-(docos-1-en-1-yloxy)-2-methylbenzene, 3-methoxy-2-methylphenol, 3-ethoxy-2-methylphenol, 3-propoxy-2-methylphenol, 3-butoxy-2-methylphenol, 3-pentyloxy-2-methylphenol, 3-hexyloxy-2-methylphenol, 3-heptyloxy-2-methylphenol, 3-octylxy-2-methylphenol, 3-nonylxy-2-methylphenol, 3-(decyloxy)-2-methylphenol, 3-(undecyloxy)-2-methylphenol, 3-(dodecyloxy)-2-methylphenol, 3-(tridecyloxy)-2-methylphenol, 3-(tetradecyloxy)-2-methylphenol, 3-(pentadecyloxy)-2-methylphenol, 3-(hexadecyloxy)-2-methylphenol, 3-(heptadecyloxy)-2-methylphenol, 3-(octadecyloxy)-2-methylphenol, 3-(nonadecyloxy)-2-methylphenol, 3-(icosyloxy)-2-methylphenol, 3-(henicosyloxy)-2-methylphenol, 3-(docosyloxy)-2-methylphenol, 3-(3-hydroxyphenoxy)propane-1,2-diol, 3-(2-hydroxy-3-methoxypropoxy)phenol, 3-(3-ethoxy-2-hydroxypropoxy)phenol, 3-(2-hydroxy-3-propoxypropoxy)phenol, 3-(3-butoxy-2-hydroxypropoxy)phenol, 3-(2-hydroxy-3-(pentyloxy)propoxy)phenol, 3-(3-(hexan-2-yloxy)-2-hydroxypropoxy)phenol, 3-(2-hydroxy-3-(pentan-2-yloxy)propoxy)phenol, 3-(3-(sec-butoxy)-2-hydroxypropoxy)phenol, 3-(2-hydroxy-3-isopropoxypropoxy)phenol, 3-(2-hydroxy-3-(undecyloxy)propoxy)phenol, 3-(2-hydroxy-3-(dodecyloxy)propoxy)phenol, 3-(2-hydroxy-3-(tridecyloxy)propoxy)phenol, 3-(2-hydroxy-3-(tetradecyloxy)propoxy)phenol, 3-(2-hydroxy-3-(pentadecyloxy)propoxy)phenol, 3-(2-hydroxy-3-(hexadecyloxy)propoxy)phenol, 3-(2-hydroxy-3-(heptadecyloxy)propoxy)phenol, 3-(2-hydroxy-3-(octadecyloxy)propoxy)phenol, 3-(2-hydroxy-3-(nonadecyloxy)propoxy)phenol, 3-(2-hydroxy-3-(nonan-5-yloxy)propoxy)phenol, 3-methoxyphenol, 3-ethoxyphenol, 3-butoxyphenol, 3-(pentyloxy)phenol, 3-(hexyloxy)phenol, 3-(heptyloxy)phenol, 3-(octyloxy)phenol, 3-(nonyloxy)phenol, 3-(decyloxy)phenol, 3-(undecyloxy)phenol, 3-(dodecyloxy)phenol, 3-(tridecyloxy)phenol, 3-(tetradecyloxy)phenol, 3-(pentadecyloxy)phenol, 3-(hexadecyloxy)phenol, 3-(heptadecyloxy)phenol, 3-(octadecyloxy)phenol, 3-(nonadecyloxy)phenol, 3-(icosyloxy)phenol, 3-(henicosyloxy)phenol, 3-(docosyloxy)phenol, 2-methoxyphenol, 2-ethoxyphenol, 2-butoxyphenol, 2-(pentyloxy)phenol, 2-(hexyloxy)phenol, 2-(heptyloxy)phenol, 2-(octyloxy)phenol, 2-(nonyloxy)phenol, 2-(decyloxy)phenol, 2-(undecyloxy)phenol, 2-(dodecyloxy)phenol, 2-(tridecyloxy)phenol, 2-(tetradecyloxy)phenol, 2-(pentadecyloxy)phenol, 2-(hexadecyloxy)phenol, 2-(heptadecyloxy)phenol, 2-(octadecyloxy)phenol, 2-(nonadecyloxy)phenol, 2-(icosyloxy)phenol, 2-(henicosyloxy)phenol, 2-(docosyloxy)phenol, 4-methoxyphenol, 4-ethoxyphenol, 4-butoxyphenol, 4-(pentyloxy)phenol, 4-(hexyloxy)phenol, 4-(heptyloxy)phenol, 4-(octyloxy)phenol, 4-(nonyloxy)phenol, 4-(decyloxy)phenol, 4-(undecyloxy)phenol, 4-(dodecyloxy)phenol, 4-(tridecyloxy)phenol, 4-(tetradecyloxy)phenol, 4-(pentadecyloxy)phenol, 4-(hexadecyloxy)phenol, 4-(heptadecyloxy)phenol, 4-(octadecyloxy)phenol, 4-(nonadecyloxy)phenol, 4-(icosyloxy)phenol, 4-(henicosyloxy)phenol, 4-(docosyloxy)phenol, 3-(2-hydroxy-3-(2-methylbutoxy)propoxy)phenol, 3-(3-(2-ethylbutoxy)-2-hydroxypropoxy)phenol, 3-(3-((2-ethylpentyl)oxy)-2-hydroxypropoxy)phenol, 3-(3-((2-ethylhexyl)oxy)-2-hydroxypropoxy)phenol, 3-(3-((2-ethylheptyl)oxy)-2-hydroxypropoxy)phenol, 3-(3-((2-ethyloctyl)oxy)-2-hydroxypropoxy)phenol, 3-(3-((2-ethylnonyl)oxy)-2-hydroxypropoxy)phenol, 3-(3-((2-ethyldecyl)oxy)-2-hydroxypropoxy)phenol, 3-(3-((2-ethylundecyl)oxy)-2-hydroxypropoxy)phenol, 3-(3-((2-ethyldodecyl)oxy)-2-hydroxypropoxy)phenol, 3-(3-((2-ethyltridecyl)oxy)-2-hydroxypropoxy)phenol, 3-(3-((2-ethyltetradecyl)oxy)-2-hydroxypropoxy)phenol, 3-(3-((2-ethylpentadecyl)oxy)-2-hydroxypropoxy)phenol, 3-(3-((2-ethylhexadecyl)oxy)-2-hydroxypropoxy)phenol, 3-(3-((2-ethylheptadecyl)oxy)-2-hydroxypropoxy)phenol, 3-(3-((2-ethyloctadecyl)oxy)-2-hydroxypropoxy)phenol, 3-(3-((2-ethylnonadecyl)oxy)-2-hydroxypropoxy)phenol, 3-(3-((2-ethylicosyl)oxy)-2-hydroxypropoxy)phenol, 2-(3-hydroxyphenoxy)propanoic acid, methyl 2-(3-hydroxyphenoxy)propanoate, ethyl 2-(3-hydroxyphenoxy)propanoate, propyl 2-(3-hydroxyphenoxy)propanoate, butyl 2-(3-hydroxyphenoxy)propanoate, pentyl 2-(3-hydroxyphenoxy)propanoate, hexyl 2-(3-hydroxyphenoxy)propanoate, heptyl 2-(3-hydroxyphenoxy)propanoate, octyl 2-(3-hydroxyphenoxy)propanoate, nonyl 2-(3-hydroxyphenoxy)propanoate, decyl 2-(3-hydroxyphenoxy)propanoate, undecyl 2-(3-hydroxyphenoxy)propanoate, dodecyl 2-(3-hydroxyphenoxy)propanoate, tridecyl 2-(3-hydroxyphenoxy)propanoate, tetradecyl 2-(3-hydroxyphenoxy)propanoate, pentadecyl 2-(3-hydroxyphenoxy)propanoate, hexadecyl 2-(3-hydroxyphenoxy)propanoate, heptadecyl 2-(3-hydroxyphenoxy)propanoate, octadecyl 2-(3-hydroxyphenoxy)propanoate, nonadecyl 2-(3-hydroxyphenoxy)propanoate, icosyl 2-(3-hydroxyphenoxy)propanoate, 1,1'-biphenyl, [1,1'-biphenyl]-4-ol, [1,1'-biphenyl]-3-ol, [1,1'-biphenyl]-2-ol, 2-methyl-[1,1'-biphenyl]-3-ol, 6-methyl-[1,1'-biphenyl]-3-ol and 5-methyl-[1,1'-biphenyl]-3-ol, and 3-methyl-1,1'-biphenyl.

In another preferred embodiment, the at least one acid used in the process for preparing a compound of formula (A) is selected from the group consisting of inorganic acid, Lewis acid, and organic acid.

In another preferred embodiment, the at least one inorganic acid used in the process for preparing a compound of formula (A) is selected from the group consisting of sulfuric acid, hydrochloric acid, phosphoric acid ($H_3PO_4$), phosphorous acid ($H_3PO_3$), phosphinic acid ($H_3PO_2$), perchloric acid, nitric acid, nitrous acid, sulphurous acid, chloric acid, chlorous acid and hypochlorous acid; more preferably the at least one inorganic acid used in the process for preparing a compound of formula (F) is hydrochloric acid.

In another preferred embodiment, the at least one Lewis acid used in the process for preparing a compound of formula (A) is selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I;

$BH_3$, $B(CH_3)_3$, $GaH_3$, $AlH_3$, Al (acetate)(OH)$_2$, Al[OCH(CH$_3$)$_2$]$_3$, Al(OCH$_3$)$_3$, Al(OC$_2$H$_5$)$_3$, Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$; Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$; more preferably the Lewis acid is selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—$S(=O)_2O$, $CH_3$—$S(=O)_2O$, or I; most preferably selected from the group consisting of $BX_3$, $BX_3 \cdot (C_2H_5)_2O$, $BX_3 \cdot S(CH_3)_2$, $AlX_3$, $(C_2H_5)_2AlX$, $TiX_2$, $TiX_4$ whereby X in each case denotes F, Cl, Br, $S(=O)_3$, $CF_3—S(=O)_2O$, $CH_3—S(=O)_2O$, or I; In particular preferably selected from the group consisting of $BX_3$, $AlX_3$, $(C_2H_5)_2AlX$, whereby X in each case denotes F, Cl, Br, $CF_3—S(=O)_2O$, $CH_3—S(=O)_2O$, or I.

In another preferred embodiment, the at least one Lewis acid used in the process for preparing a compound of formula (A) is selected from the group consisting of $BX_3$, $BX_3 \cdot (C_2H_5)_2O$, $BX_3 \cdot S(CH_3)_2$, $AlX_3$, $ZnX_2$, $FeX_3$ and $TiX_4$, whereby X in each case denotes F, Cl, or Br.

In another preferred embodiment, the at least one organic acid used in the process for preparing a compound of formula (A) is selected from the group consisting organic carboxylic acid and organic sulfonic acid.

In another preferred embodiment, the at least one organic carboxylic acid used in the process for preparing a compound of formula (A) is selected from the group consisting of acetic acid, formic acid, propionic acid, butanoic acid, benzoic acid, phthalic acid, oxalic acid, malonic acid, succinic acid, glutaric acid, adipic acid, lactic acid, citric acid, uric acid and malic acid; more preferably the at least one organic carboxylic acid used in the process for preparing a compound of formula (A) is selected from the group consisting of acetic acid, formic acid, propionic acid, butanoic acid and benzoic acid; most preferably the at least one organic carboxylic acid used in the process for preparing a compound of formula (A) is selected from the group consisting of acetic acid and formic acid.

In a preferred embodiment, the organic sulfonic acid used in the process for preparing a compound of formula (A) is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid, more preferably the organic sulfonic acid used in the process for preparing a compound of formula (A) is selected from the group consisting of methanesulfonic acid, trifluoromethanesulfonic acid, benzenesulfonic acid and p-toluenesulfonic acid, even more preferably the organic sulfonic acid used in the process for preparing a compound of formula (A) is selected from the group consisting of trifluoromethanesulfonic acid, methanesulfonic acid and p-toluenesulfonic acid.

In another preferred embodiment, the molar ratio of the at least one Lewis acid to the at least one compound of formula (F) is in in the range of 1:10 to 10:1; more preferably in in the range of 1:8 to 8:1; even more in in the range of 1:5 to 5:1; most preferably in in the range of 1:3 to 3:1; and in particular preferably in in the range of 1:2 to 2:1.

In another preferred embodiment, the molar ratio of the at least one acid, preferably the at least Lewis acid, to the at least one compound of formula (G) is in in the range of 1:10 to 10:1; more preferably in in the range of 1:8 to 8:1; even more in in the range of 1:5 to 5:1; most preferably in in the range of 1:3 to 3:1; and in particular preferably in in the range of 1:2 to 2:1.

In another preferred embodiment, the molar ratio of the at least one compound of formula (G) to the at least one compound of formula (F) is in the range of 2:5 to 5:2; more preferably in the range of 1:2 to 2:1; and most preferably in the range of 1:1 to 2:1.

In another preferred embodiment, the at least one compound of formula (F) and the at least one compound of formula (G) are reacted in the presence of at least one solvent selected from the group consisting of aliphatic and aromatic hydrocarbons, halogenated aliphatic, halogenated aromatic hydrocarbons, ethers and carbon disulphide, more preferably aliphatic and aromatic hydrocarbons, halogenated aliphatic, halogenated aromatic hydrocarbons, most preferably aromatic hydrocarbons, halogenated aliphatic and halogenated aromatic hydrocarbons, and even more preferably in aromatic hydrocarbons and halogenated aromatic hydrocarbons.

In another preferred embodiment, the at least one compound of formula (F) and the at least one compound of formula (G) are reacted at a temperature in the range of 0 to 250° C., more preferably at a temperature in the range of 50 to 200° C., even more preferably, at a temperature in the range of 80 to 180° C., most preferably at a temperature in the range of 100 to 180° C. and in particular preferably at a temperature in the range of 120 to 180° C.

In another preferred embodiment, the at least one compound of formula (F) and the at least one compound of formula (G) are reacted for a period of 30 minutes to 24 hours, more preferably 30 minutes to 15 hours, even more preferably 1 hour to 10 hours, most preferably 1 hour to 6 hours, and in particular preferably 1 hour to 5 hours.

The compound of formula (A) formed in the step (iv) is isolated by any method known in the art selected from the group consisting of chemical separation, acid-base neutralization, distillation, evaporation, column chromatography, filtration, concentration, crystallization and re-crystallization or a combination thereof. A person skilled in the art is familiar with such techniques.

Step (v)

In another preferred embodiment, the process comprises a step of:
v) reacting the compound of formula (A) obtained according to step iv) with at least one alkyl halide or at least one acyl halide to obtain a UV absorber compounds.

In another preferred embodiment, the alkylation of the compound of formula obtained in step iv) is carried out, when the $R_6Y$ is OH. For example, having a general formula as follow:

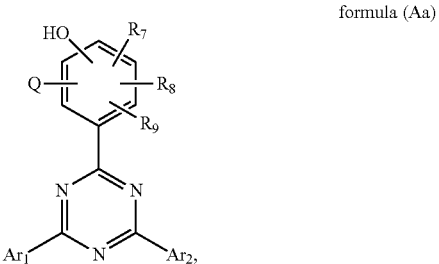

formula (Aa)

wherein $Ar_1$, $Ar_2$ Q, $R_7$, $R_8$ and $R_9$ are defined as above.

In another preferred embodiment, the at least one alkyl halide is a $C_1$-$C_{24}$ alkyl halide.

In another preferred embodiment the at least one alkyl halide refers to a linear or branched, unsubstituted $C_1$-$C_{24}$ alkyl halide selected from the group consisting of methyl halide, ethyl halide, propyl halide, butyl halide, pentyl halide, hexyl halide, heptyl halide, octyl halide, nonyl halide, decyl halide, undecyl halide, dodecyl halide, tridecyl halide, tetradecyl halide, pentadecyl halide, hexadecyl halide, heptadecyl halide, octadecyl halide, nonadecyl halide, icosyl halide, henicosyl halide, docosyl halide, tricosyl halide, tetracosyl halide, 1-methyl ethyl halide, 1-methyl propyl halide, 2-methyl propyl halide, 1-methyl butyl halide, 2-methyl butyl halide, 3-methyl butyl halide, 1-methyl pentyl halide, 2-methyl pentyl halide, 3-methyl pentyl halide, 4-methyl pentyl halide, 1-methyl hexyl halide, 2-methyl hexyl halide, 3-methyl hexyl halide, 4-methyl hexyl halide, 5-methyl hexyl halide, 1-methyl heptyl halide, 2-methyl heptyl halide, 3-methyl heptyl halide, 4-methyl heptyl halide, 5-methyl heptyl halide, 6-methyl heptyl halide, 1-methyl octyl halide, 2-methyl octyl halide, 3-methyl octyl halide, 4-methyl octyl halide, 5-methyl octyl halide, 6-methyl octyl halide, 7-methyl octyl halide, 1-methyl nonyl halide, 2-methyl nonyl halide, 3-methyl nonyl halide, 4-methyl nonyl halide, 5-methyl nonyl halide, 6-methyl nonyl halide, 7-methyl nonyl halide, 8-methyl nonyl halide, 1-methyl decyl halide, 2-methyl decyl halide, 3-methyl decyl halide, 4-methyl decyl halide, 5-methyl decyl halide, 6-methyl decyl halide, 7-methyl decyl halide, 8-methyl decyl halide, 9-methyl decyl halide, 1-methyl undecyl halide, 2-methyl undecyl halide, 3-methyl undecyl halide, 4-methyl undecyl halide, 5-methyl undecyl halide, 6-methyl undecyl halide, 7-methyl undecyl halide, 8-methyl undecyl halide, 9-methyl undecyl halide, 10-methyl undecyl halide, 1-methyl dodecyl halide, 2-methyl dodecyl halide, 3-methyl dodecyl halide, 4-methyl dodecyl halide, 5-methyl dodecyl halide, 6-methyl dodecyl halide, 7-methyl dodecyl halide, 8-methyl dodecyl halide, 9-methyl dodecyl halide, 10-methyl dodecyl halide, 11-methyl dodecyl halide, 1-methyl tridecyl halide, 2-methyl tridecyl halide, 3-methyl tridecyl halide, 4-methyl tridecyl halide, 5-methyl tridecyl halide, 6-methyl tridecyl halide, 7-methyl tridecyl halide, 8-methyl tridecyl halide, 9-methyl tridecyl halide, 10-methyl tridecyl halide, 11-methyl tridecyl halide, 12-methyl tridecyl halide, 1-methyl tetradecyl halide, 2-methyl tetradecyl halide, 3-methyl tetradecyl halide, 4-methyl tetradecyl halide, 5-methyl tetradecyl halide, 6-methyl tetradecyl halide, 7-methyl tetradecyl halide, 8-methyl tetradecyl halide, 9-methyl tetradecyl halide, 10-methyl tetradecyl halide, 11-methyl tetradecyl halide, 12-methyl tetradecyl halide, 13-methyl tetradecyl halide, 1-methyl pentadecyl halide, 2-methyl pentadecyl halide, 3-methyl pentadecyl halide, 4-methyl pentadecyl halide, 5-methyl pentadecyl halide, 6-methyl pentadecyl halide, 7-methyl pentadecyl halide, 8-methyl pentadecyl halide, 9-methyl pentadecyl halide, 10-methyl pentadecyl halide, 11-methyl pentadecyl halide, 12-methyl pentadecyl halide, 13-methyl pentadecyl halide, 14-methyl pentadecyl halide, 1-methyl hexadecyl halide, 2-methyl hexadecyl halide, 3-methyl hexadecyl halide, 4-methyl hexadecyl halide, 5-methyl hexadecyl halide, 6-methyl hexadecyl halide, 7-methyl hexadecyl halide, 8-methyl hexadecyl halide, 9-methyl hexadecyl halide, 10-methyl hexadecyl halide, 11-methyl hexadecyl halide, 12-methyl hexadecyl halide, 13-methyl hexadecyl halide, 14-methyl hexadecyl halide, 15-methyl hexadecyl halide, 1-methyl heptadecyl halide, 2-methyl heptadecyl halide, 3-methyl heptadecyl halide, 4-methyl heptadecyl halide, 5-methyl heptadecyl halide, 6-methyl heptadecyl halide, 7-methyl heptadecyl halide, 8-methyl heptadecyl halide, 9-methyl heptadecyl halide, 10-methyl heptadecyl halide, 11-methyl heptadecyl halide, 12-methyl heptadecyl halide, 13-methyl heptadecyl halide, 14-methyl heptadecyl halide, 15-methyl heptadecyl halide, 16-methyl heptadecyl halide, 1-methyl octadecyl halide, 2-methyl octadecyl halide, 3-methyl octadecyl halide, 4-methyl octadecyl halide, 5-methyl octadecyl halide, 6-methyl octadecyl halide, 7-methyl octadecyl halide, 8-methyl octadecyl halide, 9-methyl octadecyl halide, 10-methyl octadecyl halide, 11-methyl octadecyl halide, 12-methyl octadecyl halide, 13-methyl octadecyl halide, 14-methyl octadecyl halide, 15-methyl octadecyl halide, 16-methyl octadecyl halide, 17-methyl octadecyl halide, 1-methyl nonadecyl halide, 2-methyl nonadecyl halide, 3-methyl nonadecyl halide, 4-methyl nonadecyl halide, 5-methyl nonadecyl halide, 6-methyl nonadecyl halide, 7-methyl nonadecyl halide, 8-methyl nonadecyl halide, 9-methyl nonadecyl halide, 10-methyl nonadecyl halide, 11-methyl nonadecyl halide, 12-methyl nonadecyl halide, 13-methyl nonadecyl halide, 14-methyl nonadecyl halide, 15-methyl nonadecyl halide, 16-methyl nonadecyl halide, 17-methyl nonadecyl halide, 18-methyl nonadecyl halide, 1-methyl icosyl halide, 2-methyl icosyl halide, 3-methyl icosyl halide, 4-methyl icosyl halide, 5-methyl icosyl halide, 6-methyl icosyl halide, 7-methyl icosyl halide, 8-methyl icosyl halide, 9-methyl icosyl halide, 10-methyl icosyl halide, 11-methyl icosyl halide, 12-methyl icosyl halide, 13-methyl icosyl halide, 14-methyl icosyl halide, 15-methyl icosyl halide, 16-methyl icosyl halide, 17-methyl icosyl halide, 18-methyl icosyl halide, 19-methyl icosyl halide, 1-methyl henicosyl halide, 2-methyl henicosyl halide, 3-methyl henicosyl halide, 4-methyl henicosyl halide, 5-methyl henicosyl halide, 6-methyl henicosyl halide, 7-methyl henicosyl halide, 8-methyl henicosyl halide, 9-methyl henicosyl halide, 10-methyl henicosyl halide, 11-methyl henicosyl halide, 12-methyl henicosyl halide, 13-methyl henicosyl halide, 14-methyl henicosyl halide, 15-methyl henicosyl halide, 16-methyl henicosyl halide, 17-methyl henicosyl halide, 18-methyl henicosyl halide, 19-methyl henicosyl halide, 20-methyl henicosyl halide, 1-methyl docosyl halide, 2-methyl docosyl halide, 3-methyl docosyl halide, 4-methyl docosyl halide, 5-methyl docosyl halide, 6-methyl docosyl halide, 7-methyl docosyl halide, 8-methyl docosyl halide, 9-methyl docosyl halide, 10-methyl docosyl halide, 11-methyl docosyl halide, 12-methyl docosyl halide, 13-methyl docosyl halide, 14-methyl docosyl halide, 15-methyl docosyl halide, 16-methyl docosyl halide, 17-methyl docosyl halide, 18-methyl docosyl halide, 19-methyl docosyl halide, 20-methyl docosyl halide, 21-methyl docosyl halide, 1-methyl tricosyl halide, 2-methyl tricosyl halide, 3-methyl tricosyl halide, 4-methyl tricosyl halide, 5-methyl tricosyl halide, 6-methyl tricosyl halide, 7-methyl tricosyl halide, 8-methyl tricosyl halide, 9-methyl tricosyl halide, 10-methyl tricosyl halide, 11-methyl tricosyl halide, 12-methyl tricosyl halide, 13-methyl tricosyl halide, 14-methyl tricosyl halide, 15-methyl tricosyl halide, 16-methyl tricosyl halide, 17-methyl tricosyl halide, 18-methyl tricosyl halide, 19-methyl tricosyl halide, 20-methyl tricosyl halide, 21-methyl tricosyl halide, 22-methyl tricosyl halide, 1-ethyl propyl halide, 1-ethyl butyl halide, 2-ethyl butyl halide, 1-ethyl pentyl halide, 2-ethyl pentyl halide, 3-ethyl pentyl halide, 1-ethyl hexyl halide, 2-ethyl hexyl halide, 3-ethyl hexyl halide, 4-ethyl hexyl halide, 1-ethyl heptyl halide, 2-ethyl heptyl halide, 3-ethyl heptyl halide, 4-ethyl heptyl halide, 5-ethyl heptyl halide, 1-ethyl octyl halide, 2-ethyl octyl halide, 3-ethyl octyl halide, 4-ethyl octyl halide, 5-ethyl octyl halide, 6-ethyl octyl halide, 1-ethyl nonyl halide, 2-ethyl nonyl halide, 3-ethyl nonyl halide, 4-ethyl nonyl halide, 5-ethyl nonyl halide, 6-ethyl nonyl halide, 7-ethyl nonyl halide, 1-ethyl decyl halide, 2-ethyl decyl halide, 3-ethyl decyl halide, 4-ethyl decyl halide, 5-ethyl decyl halide, 6-ethyl decyl halide, 7-ethyl decyl halide, 8-ethyl decyl halide, 1-ethyl undecyl halide, 2-ethyl undecyl halide, 3-ethyl undecyl halide, 4-ethyl undecyl halide, 5-ethyl undecyl halide, 6-ethyl undecyl halide, 7-ethyl undecyl halide, 8-ethyl undecyl halide, 9-ethyl undecyl halide, 1-ethyl dodecyl halide, 2-ethyl dodecyl halide, 3-ethyl dodecyl halide, 4-ethyl dodecyl halide, 5-ethyl dodecyl halide, 6-ethyl dodecyl halide, 7-ethyl dodecyl halide, 8-ethyl dodecyl halide, 9-ethyl dodecyl halide, 10-ethyl dodecyl halide, 1-ethyl tridecyl halide, 2-ethyl tridecyl halide, 3-ethyl tridecyl halide, 4-ethyl tridecyl halide, 5-ethyl tridecyl halide, 6-ethyl tridecyl halide, 7-ethyl tridecyl halide, 8-ethyl tridecyl halide, 9-ethyl tridecyl halide, 10-ethyl tridecyl halide, 11-ethyl tridecyl halide, 1-ethyl tetradecyl halide, 2-ethyl tetradecyl halide, 3-ethyl tetradecyl halide, 4-ethyl tetradecyl halide, 5-ethyl tetradecyl halide, 6-ethyl tetradecyl halide, 7-ethyl tetradecyl halide, 8-ethyl tetradecyl halide, 9-ethyl tetradecyl halide, 10-ethyl tetradecyl halide, 11-ethyl tetradecyl halide, 12-ethyl tetradecyl halide, 1-ethyl pentadecyl halide, 2-ethyl pentadecyl halide, 3-ethyl pentadecyl halide, 4-ethyl pentadecyl halide, 5-ethyl pentadecyl halide, 6-ethyl pentadecyl halide, 7-ethyl pentadecyl halide, 8-ethyl pentadecyl halide, 9-ethyl pentadecyl halide, 10-ethyl pentadecyl halide, 11-ethyl pentadecyl halide, 12-ethyl pentadecyl halide, 13-ethyl pentadecyl halide, 1-ethyl hexadecyl halide, 2-ethyl hexadecyl halide, 3-ethyl hexadecyl halide, 4-ethyl hexadecyl halide, 5-ethyl hexadecyl halide, 6-ethyl hexadecyl halide, 7-ethyl hexadecyl halide, 8-ethyl hexadecyl halide, 9-ethyl hexadecyl halide, 10-ethyl hexadecyl halide, 11-ethyl hexadecyl halide, 12-ethyl hexadecyl halide, 13-ethyl hexadecyl halide, 14-ethyl hexadecyl halide, 1-ethyl heptadecyl halide, 2-ethyl heptadecyl halide, 3-ethyl heptadecyl halide, 4-ethyl heptadecyl halide, 5-ethyl heptadecyl halide, 6-ethyl heptadecyl halide, 7-ethyl heptadecyl halide, 8-ethyl heptadecyl halide, 9-ethyl heptadecyl halide, 10-ethyl heptadecyl halide, 11-ethyl heptadecyl halide, 12-ethyl heptadecyl halide, 13-ethyl heptadecyl halide, 14-ethyl heptadecyl halide, 15-ethyl heptadecyl halide, 1-ethyl octadecyl halide, 2-ethyl octadecyl halide, 3-ethyl octadecyl halide, 4-ethyl octadecyl halide, 5-ethyl octadecyl halide, 6-ethyl octadecyl halide, 7-ethyl octadecyl halide, 8-ethyl octadecyl halide, 9-ethyl octadecyl halide, 10-ethyl octadecyl halide, 11-ethyl octadecyl halide, 12-ethyl octadecyl halide, 13-ethyl octadecyl halide, 14-ethyl octadecyl halide, 15-ethyl octadecyl halide, 16-ethyl octadecyl halide, 1-ethyl nonadecyl halide, 2-ethyl nonadecyl halide, 3-ethyl nonadecyl halide, 4-ethyl nonadecyl halide, 5-ethyl nonadecyl halide, 6-ethyl nonadecyl halide, 7-ethyl nonadecyl halide, 8-ethyl nonadecyl halide, 9-ethyl nonadecyl halide, 10-ethyl nonadecyl halide, 11-ethyl nonadecyl halide, 12-ethyl nonadecyl halide, 13-ethyl nonadecyl halide, 14-ethyl nonadecyl halide, 15-ethyl nonadecyl halide, 16-ethyl nonadecyl halide, 17-ethyl nonadecyl halide, 1-ethyl icosyl halide, 2-ethyl icosyl halide, 3-ethyl icosyl halide, 4-ethyl icosyl halide, 5-ethyl icosyl halide, 6-ethyl icosyl halide, 7-ethyl icosyl halide, 8-ethyl icosyl halide, 9-ethyl icosyl halide, 10-ethyl icosyl halide, 11-ethyl icosyl halide, 12-ethyl icosyl halide, 13-ethyl icosyl halide, 14-ethyl icosyl halide, 15-ethyl icosyl halide, 16-ethyl icosyl halide, 17-ethyl icosyl halide, 18-ethyl icosyl halide, 1-ethyl henicosyl halide, 2-ethyl henicosyl halide, 3-ethyl henicosyl halide, 4-ethyl henicosyl halide, 5-ethyl henicosyl halide, 6-ethyl henicosyl halide, 7-ethyl henicosyl halide, 8-ethyl henicosyl halide, 9-ethyl henicosyl halide, 10-ethyl henicosyl halide, 11-ethyl henicosyl halide, 12-ethyl henicosyl halide, 13-ethyl henicosyl halide, 14-ethyl henicosyl halide, 15-ethyl henicosyl halide, 16-ethyl henicosyl halide, 17-ethyl henicosyl halide, 18-ethyl henicosyl halide, 19-ethyl henicosyl halide, 1-ethyl docosyl halide, 2-ethyl docosyl halide, 3-ethyl docosyl halide, 4-ethyl docosyl halide, 5-ethyl docosyl halide, 6-ethyl docosyl halide, 7-ethyl docosyl halide, 8-ethyl docosyl halide, 9-ethyl docosyl halide, 10-ethyl docosyl halide, 11-ethyl docosyl halide, 12-ethyl docosyl halide, 13-ethyl docosyl halide, 14-ethyl docosyl halide, 15-ethyl docosyl halide, 16-ethyl docosyl halide, 17-ethyl docosyl halide, 18-ethyl docosyl halide, 19-ethyl docosyl halide, 20-ethyl docosyl halide, 1-propyl butyl halide, 1-propyl pentyl halide, 2-propyl pentyl halide, 1-propyl hexyl halide, 2-propyl hexyl halide, 3-propyl hexyl halide, 1-propyl heptyl halide, 2-propyl heptyl halide, 3-propyl heptyl halide, 4-propyl heptyl halide, 1-propyl octyl halide, 2-propyl octyl halide, 3-propyl octyl halide, 4-propyl octyl halide, 5-propyl octyl halide, 1-propyl nonyl halide, 2-propyl nonyl halide, 3-propyl nonyl halide, 4-propyl nonyl halide, 5-propyl nonyl halide, 6-propyl nonyl halide, 1-propyl decyl halide, 2-propyl decyl halide, 3-propyl decyl halide, 4-propyl decyl halide, 5-propyl decyl halide, 6-propyl decyl halide, 7-propyl decyl halide, 1-propyl undecyl halide, 2-propyl undecyl halide, 3-propyl undecyl halide, 4-propyl undecyl halide, 5-propyl undecyl halide, 6-propyl undecyl halide, 7-propyl undecyl halide, 8-propyl undecyl halide, 1-propyl dodecyl halide, 2-propyl dodecyl halide, 3-propyl dodecyl halide, 4-propyl dodecyl halide, 5-propyl dodecyl halide, 6-propyl dodecyl halide, 7-propyl dodecyl halide, 8-propyl dodecyl halide, 9-propyl dodecyl halide, 1-propyl tridecyl halide, 2-propyl tridecyl halide, 3-propyl tridecyl halide, 4-propyl tridecyl halide, 5-propyl tridecyl halide, 6-propyl tridecyl halide, 7-propyl tridecyl halide, 8-propyl tridecyl halide, 9-propyl tridecyl halide, 10-propyl tridecyl halide, 1-propyl tetradecyl halide, 2-propyl tetradecyl halide, 3-propyl tetradecyl halide, 4-propyl tetradecyl halide, 5-propyl tetradecyl halide, 6-propyl tetradecyl halide, 7-propyl tetradecyl halide, 8-propyl tetradecyl halide, 9-propyl tetradecyl halide, 10-propyl tetradecyl halide, 11-propyl tetradecyl halide, 1-propyl pentadecyl halide, 2-propyl pentadecyl halide, 3-propyl pentadecyl halide, 4-propyl pentadecyl halide, 5-propyl pentadecyl halide, 6-propyl pentadecyl halide, 7-propyl pentadecyl halide, 8-propyl pentadecyl halide, 9-propyl pentadecyl halide, 10-propyl pentadecyl halide, 11-propyl pentadecyl halide, 12-propyl pentadecyl halide, 1-propyl hexadecyl halide, 2-propyl hexadecyl halide, 3-propyl hexadecyl halide, 4-propyl hexadecyl halide, 5-propyl hexadecyl halide, 6-propyl hexadecyl halide, 7-propyl hexadecyl halide, 8-propyl hexadecyl halide, 9-propyl hexadecyl halide, 10-propyl hexadecyl halide, 11-propyl hexadecyl halide, 12-propyl hexadecyl halide, 13-propyl hexadecyl halide, 1-propyl heptadecyl halide, 2-propyl heptadecyl halide, 3-propyl heptadecyl halide, 4-propyl heptadecyl halide, 5-propyl heptadecyl halide, 6-propyl heptadecyl halide, 7-propyl heptadecyl halide, 8-propyl heptadecyl halide, 9-propyl heptadecyl halide, 10-propyl heptadecyl halide, 11-propyl heptadecyl halide, 12-propyl heptadecyl halide, 13-propyl heptadecyl halide, 14-propyl heptadecyl halide, 1-propyl octadecyl halide, 2-propyl octadecyl halide, 3-propyl octadecyl halide, 4-propyl octadecyl halide, 5-propyl octadecyl halide, 6-propyl octadecyl halide, 7-propyl octadecyl halide, 8-propyl octadecyl halide, 9-propyl octadecyl halide, 10-propyl octadecyl halide, 11-propyl octadecyl halide, 12-propyl octadecyl halide, 13-propyl octadecyl halide, 14-propyl octadecyl halide, 15-propyl octadecyl halide, 1-propyl nonadecyl halide, 2-propyl nonadecyl halide, 3-propyl nonadecyl halide, 4-propyl nonadecyl halide, 5-propyl nonadecyl halide, 6-propyl nonadecyl halide, 7-propyl nonadecyl halide, 8-propyl nonadecyl halide, 9-propyl nonadecyl halide, 10-propyl nonadecyl halide, 11-propyl nonadecyl halide, 12-propyl nonadecyl halide, 13-propyl nonadecyl halide, 14-propyl nonadecyl halide, 15-propyl nonadecyl halide, 16-propyl nonadecyl halide, 1-propyl icosyl halide, 2-propyl icosyl halide, 3-propyl icosyl halide, 4-propyl icosyl halide, 5-propyl icosyl halide, 6-propyl icosyl halide, 7-propyl icosyl halide, 8-propyl icosyl halide, 9-propyl icosyl halide, 10-propyl icosyl halide, 11-propyl icosyl halide, 12-propyl icosyl halide, 13-propyl icosyl halide, 14-propyl icosyl halide, 15-propyl icosyl halide, 16-propyl icosyl halide, 17-propyl icosyl halide, 1-propyl henicosyl halide, 2-propyl henicosyl halide, 3-propyl henicosyl halide, 4-propyl henicosyl halide, 5-propyl henicosyl halide, 6-propyl henicosyl halide, 7-propyl henicosyl halide, 8-propyl henicosyl halide, 9-propyl henicosyl halide, 10-propyl henicosyl halide, 11-propyl henicosyl halide, 12-propyl henicosyl halide, 13-propyl henicosyl halide, 14-propyl henicosyl halide, 15-propyl henicosyl halide, 16-propyl henicosyl halide, 17-propyl henicosyl halide, 18-propyl henicosyl halide, 1-butyl pentyl halide, 1-butyl hexyl halide, 2-butyl hexyl halide, 1-butyl heptyl halide, 2-butyl heptyl halide, 3-butyl heptyl halide, 1-butyl octyl halide, 2-butyl octyl halide, 3-butyl octyl halide, 4-butyl octyl halide, 1-butyl nonyl halide, 2-butyl nonyl halide, 3-butyl nonyl halide, 4-butyl nonyl halide, 5-butyl nonyl halide, 1-butyl decyl halide, 2-butyl decyl halide, 3-butyl decyl halide, 4-butyl decyl halide, 5-butyl decyl halide, 6-butyl decyl halide, 1-butyl undecyl halide, 2-butyl undecyl halide, 3-butyl undecyl halide, 4-butyl undecyl halide, 5-butyl undecyl halide, 6-butyl undecyl halide, 7-butyl undecyl halide, 1-butyl dodecyl halide, 2-butyl dodecyl halide, 3-butyl dodecyl halide, 4-butyl dodecyl halide, 5-butyl dodecyl halide, 6-butyl dodecyl halide, 7-butyl dodecyl halide, 8-butyl dodecyl halide, 1-butyl tridecyl halide, 2-butyl tridecyl halide, 3-butyl tridecyl halide, 4-butyl tridecyl halide, 5-butyl tridecyl halide, 6-butyl tridecyl halide, 7-butyl tridecyl halide, 8-butyl tridecyl halide, 9-butyl tridecyl halide, 1-butyl tetradecyl halide, 2-butyl tetradecyl halide, 3-butyl tetradecyl halide, 4-butyl tetradecyl halide, 5-butyl tetradecyl halide, 6-butyl tetradecyl halide, 7-butyl tetradecyl halide, 8-butyl tetradecyl halide, 9-butyl tetradecyl halide, 10-butyl tetradecyl halide, 1-butyl pentadecyl halide, 2-butyl pentadecyl halide, 3-butyl pentadecyl halide, 4-butyl pentadecyl halide, 5-butyl pentadecyl halide, 6-butyl pentadecyl halide, 7-butyl pentadecyl halide, 8-butyl pentadecyl halide, 9-butyl pentadecyl halide, 10-butyl pentadecyl halide, 11-butyl pentadecyl halide, 1-butyl hexadecyl halide, 2-butyl hexadecyl halide, 3-butyl hexadecyl halide, 4-butyl hexadecyl halide, 5-butyl hexadecyl halide, 6-butyl hexadecyl halide, 7-butyl hexadecyl halide, 8-butyl hexadecyl halide, 9-butyl hexadecyl halide, 10-butyl hexadecyl halide, 11-butyl hexadecyl halide, 12-butyl hexadecyl halide, 1-butyl heptadecyl halide, 2-butyl heptadecyl halide, 3-butyl heptadecyl halide, 4-butyl heptadecyl halide, 5-butyl heptadecyl halide, 6-butyl heptadecyl halide, 7-butyl heptadecyl halide, 8-butyl heptadecyl halide, 9-butyl heptadecyl halide, 10-butyl heptadecyl halide, 11-butyl heptadecyl halide, 12-butyl heptadecyl halide, 13-butyl heptadecyl halide, 1-butyl octadecyl halide, 2-butyl octadecyl halide, 3-butyl octadecyl halide, 4-butyl octadecyl halide, 5-butyl octadecyl halide, 6-butyl octadecyl halide, 7-butyl octadecyl halide, 8-butyl octadecyl halide, 9-butyl octadecyl halide, 10-butyl octadecyl halide, 11-butyl octadecyl halide, 12-butyl octadecyl halide, 13-butyl octadecyl halide, 14-butyl octadecyl halide, 1-butyl nonadecyl halide, 2-butyl nonadecyl halide, 3-butyl nonadecyl halide, 4-butyl nonadecyl halide, 5-butyl nonadecyl halide, 6-butyl nonadecyl halide, 7-butyl nonadecyl halide, 8-butyl nonadecyl halide, 9-butyl nonadecyl halide, 10-butyl nonadecyl halide, 11-butyl nonadecyl halide, 12-butyl nonadecyl halide, 13-butyl nonadecyl halide, 14-butyl nonadecyl halide, 15-butyl nonadecyl halide, 1-butyl icosyl halide, 2-butyl icosyl halide, 3-butyl icosyl halide, 4-butyl icosyl halide, 5-butyl icosyl halide, 6-butyl icosyl halide, 7-butyl icosyl halide, 8-butyl icosyl halide, 9-butyl icosyl halide, 10-butyl icosyl halide, 11-butyl icosyl halide, 12-butyl icosyl halide, 13-butyl icosyl halide, 14-butyl icosyl halide, 15-butyl icosyl halide, 16-butyl icosyl halide, 1-pentyl hexyl halide, 1-pentyl heptyl halide, 2-pentyl heptyl halide, 1-pentyl octyl halide, 2-pentyl octyl halide, 3-pentyl octyl halide, 1-pentyl nonyl halide, 2-pentyl nonyl halide, 3-pentyl nonyl halide, 4-pentyl nonyl halide, 1-pentyl decyl halide, 2-pentyl decyl halide, 3-pentyl decyl halide, 4-pentyl decyl halide, 5-pentyl decyl halide, 1-pentyl undecyl halide, 2-pentyl undecyl halide, 3-pentyl undecyl halide, 4-pentyl undecyl halide, 5-pentyl undecyl halide, 6-pentyl undecyl halide, 1-pentyl dodecyl halide, 2-pentyl dodecyl halide, 3-pentyl dodecyl halide, 4-pentyl dodecyl halide, 5-pentyl dodecyl halide, 6-pentyl dodecyl halide, 7-pentyl dodecyl halide, 1-pentyl tridecyl halide, 2-pentyl tridecyl halide, 3-pentyl tridecyl halide, 4-pentyl tridecyl halide, 5-pentyl tridecyl halide, 6-pentyl tridecyl halide, 7-pentyl tridecyl halide, 8-pentyl tridecyl halide, 1-pentyl tetradecyl halide, 2-pentyl tetradecyl halide, 3-pentyl tetradecyl halide, 4-pentyl tetradecyl halide, 5-pentyl tetradecyl halide, 6-pentyl tetradecyl halide, 7-pentyl tetradecyl halide, 8-pentyl tetradecyl halide, 9-pentyl tetradecyl halide, 1-pentyl pentadecyl halide, 2-pentyl pentadecyl halide, 3-pentyl pentadecyl halide, 4-pentyl pentadecyl halide, 5-pentyl pentadecyl halide, 6-pentyl pentadecyl halide, 7-pentyl pentadecyl halide, 8-pentyl pentadecyl halide, 9-pentyl pentadecyl halide, 10-pentyl pentadecyl halide, 1-pentyl hexadecyl halide, 2-pentyl hexadecyl halide, 3-pentyl hexadecyl halide, 4-pentyl hexadecyl halide, 5-pentyl hexadecyl halide, 6-pentyl hexadecyl halide, 7-pentyl hexadecyl halide, 8-pentyl hexadecyl halide, 9-pentyl hexadecyl halide, 10-pentyl hexadecyl halide, 11-pentyl hexadecyl halide, 1-pentyl heptadecyl halide, 2-pentyl heptadecyl halide, 3-pentyl heptadecyl halide, 4-pentyl heptadecyl halide, 5-pentyl heptadecyl halide, 6-pentyl heptadecyl halide, 7-pentyl heptadecyl halide, 8-pentyl heptadecyl halide, 9-pentyl heptadecyl halide, 10-pentyl heptadecyl halide, 11-pentyl heptadecyl halide, 12-pentyl heptadecyl halide, 1-pentyl octadecyl halide, 2-pentyl octadecyl halide, 3-pentyl octadecyl halide, 4-pentyl octadecyl halide, 5-pentyl octadecyl halide, 6-pentyl octadecyl halide, 7-pentyl octadecyl halide, 8-pentyl octadecyl halide, 9-pentyl octadecyl halide, 10-pentyl octadecyl halide, 11-pentyl octadecyl halide, 12-pentyl octadecyl halide, 13-pentyl octadecyl halide, 1-pentyl nonadecyl halide, 2-pentyl nonadecyl halide, 3-pentyl nonadecyl halide, 4-pentyl nonadecyl halide, 5-pentyl nonadecyl halide, 6-pentyl nonadecyl halide, 7-pentyl nonadecyl halide, 8-pentyl nonadecyl halide, 9-pentyl nonadecyl halide, 10-pentyl nonadecyl halide, 11-pentyl nonadecyl halide, 12-pentyl nonadecyl halide, 13-pentyl nonadecyl halide, 14-pentyl nonadecyl halide, 1-hexyl heptyl halide, 1-hexyl octyl halide, 2-hexyl octyl halide, 1-hexyl nonyl halide, 2-hexyl nonyl halide, 3-hexyl nonyl halide, 1-hexyl decyl halide, 2-hexyl decyl halide, 3-hexyl decyl halide, 4-hexyl decyl halide, 1-hexyl undecyl halide, 2-hexyl undecyl halide, 3-hexyl undecyl halide, 4-hexyl undecyl halide, 5-hexyl undecyl halide, 1-hexyl dodecyl halide, 2-hexyl dodecyl halide, 3-hexyl dodecyl halide, 4-hexyl dodecyl halide, 5-hexyl dodecyl halide, 6-hexyl dodecyl halide, 1-hexyl tridecyl halide, 2-hexyl tridecyl halide, 3-hexyl tridecyl halide, 4-hexyl tridecyl halide, 5-hexyl tridecyl halide, 6-hexyl tridecyl halide, 7-hexyl tridecyl halide, 1-hexyl tetradecyl halide, 2-hexyl tetradecyl halide, 3-hexyl tetradecyl halide, 4-hexyl tetradecyl halide, 5-hexyl tetradecyl halide, 6-hexyl tetradecyl halide, 7-hexyl tetradecyl halide, 8-hexyl tetradecyl halide, 1-hexyl pentadecyl halide, 2-hexyl pentadecyl halide, 3-hexyl pentadecyl halide, 4-hexyl pentadecyl halide, 5-hexyl pentadecyl halide, 6-hexyl pentadecyl halide, 7-hexyl pentadecyl halide, 8-hexyl pentadecyl halide, 9-hexyl pentadecyl halide, 1-hexyl hexadecyl halide, 2-hexyl hexadecyl halide, 3-hexyl hexadecyl halide, 4-hexyl hexadecyl halide, 5-hexyl hexadecyl halide, 6-hexyl hexadecyl halide, 7-hexyl hexadecyl halide, 8-hexyl hexadecyl halide, 9-hexyl hexadecyl halide, 10-hexyl hexadecyl halide, 1-hexyl heptadecyl halide, 2-hexyl heptadecyl halide, 3-hexyl heptadecyl halide, 4-hexyl heptadecyl halide, 5-hexyl heptadecyl halide, 6-hexyl heptadecyl halide, 7-hexyl heptadecyl halide, 8-hexyl heptadecyl halide, 9-hexyl heptadecyl halide, 10-hexyl heptadecyl halide, 11-hexyl heptadecyl halide, 1-hexyl octadecyl halide, 2-hexyl octadecyl halide, 3-hexyl octadecyl halide, 4-hexyl octadecyl halide, 5-hexyl octadecyl halide, 6-hexyl octadecyl halide, 7-hexyl octadecyl halide, 8-hexyl octadecyl halide, 9-hexyl octadecyl halide, 10-hexyl octadecyl halide, 11-hexyl octadecyl halide, and 12-hexyl octadecyl halide.

In another preferred embodiment, the at least one acyl halide refers to a $C_1$ to $C_{24}$ acyl halide selected from the group consisting of acetyl halide, propionyl halide, butyryl halide, pentanoyl halide, hexanoyl halide, heptanoyl halide, octanoyl halide, nonanoyl halide, decanoyl halide, undecanoyl halide, dodecanoyl halide, tridecanoyl halide, tetradecanoyl halide, pentadecanoyl halide, hexadecanoyl halide, heptadecanoyl halide, octadecanoyl halide, nonadecanoyl halide, icosanoyl halide, henicosanoyl halide, docosanoyl halide, tricosanoyl halide and tetracosanoyl halide.

In another preferred embodiment, the alkylation or the acylation is carried in the presence of at least one base selected from the group consisting of NaOH, KOH, LiOH, $Na_2CO_3$, $K_2CO_3$, $Cs_2CO_3$, $CH_3COONa$, $CH_3COOK$, triethyl amine, and disopropyl ethylamine.

In another preferred embodiment, the alkylation or the acylation is carried in the presence of at least one a solvent selected from the group consisting of dimethyl sulfoxide, dimethyl formamide, dimethyl acetamide, anisole, N-methyl pyrrolidone, tetrahydrofuran, ethyl acetate, acetone, acetonitrile, propylene carbonate and sulfolane.

The compound of formula (A) formed in the step (v) is isolated by any method known in the art selected from the group consisting of chemical separation, acid-base neutralization, distillation, evaporation, column chromatography, filtration, concentration, crystallization and re-crystallization or a combination thereof. A person skilled in the art is familiar with such techniques.

In another preferred embodiment, the presently claimed invention is directed to a process for preparing a compound of formula (A1) comprising the steps of

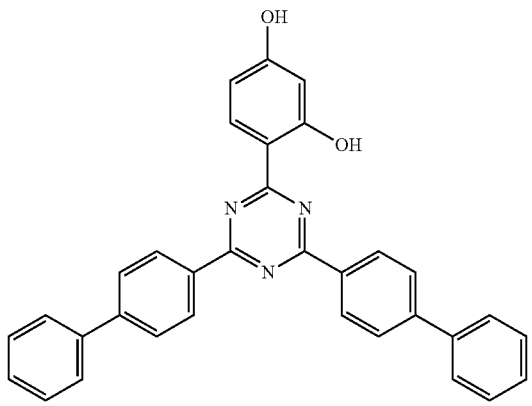

formula (A1)

i) reacting a compound of formula (C1)

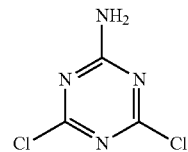

formula (C1)

with a compound of formula (B1a)

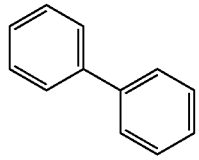

formula (B1a)

in the presence of $AlCl_3$ to obtain a compound of formula (D1)

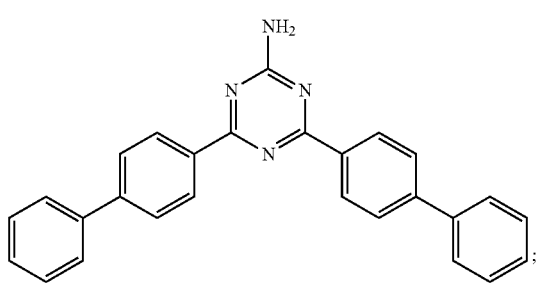

formula (D1)

ii) reacting the compound of formula (D1) obtained according to step i) with sodium hydroxide to obtain a compound of formula (E1)

i) reacting a compound of formula (C1)

formula (E1)

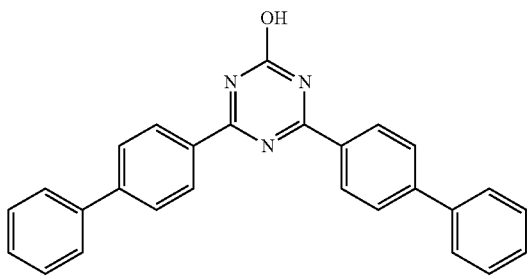

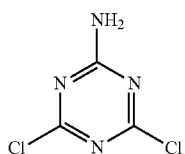
formula (C1)

with a compound of formula (B1b)

iii) reacting the compound of formula (E1) obtained according to step ii) with thionyl chloride to obtain a compound of formula (F1)

formula (B1b)

formula (F1)

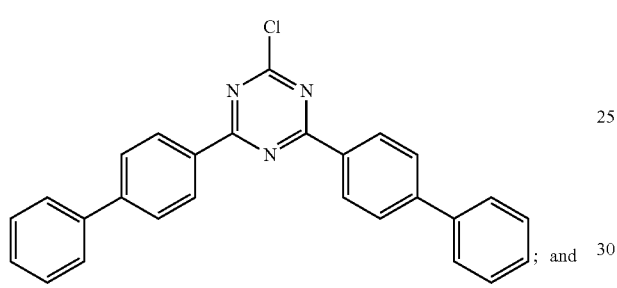

in the presence of $AlCl_3$ to obtain a compound of formula (D2)

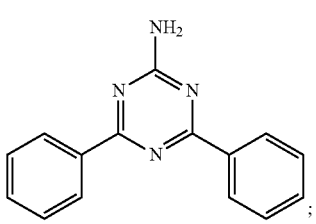
formula (D2)

iv) reacting the compound of formula (F1) obtained according to step iii) and a compound of formula (G1), ii) reacting the compound of formula (D2) obtained according to step i) with sodium hydroxide to obtain a compound of formula (E2)

formula (G1)

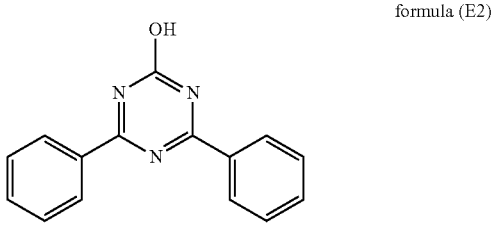
formula (E2)

in the presence $AlCl_3$ to obtain the compound of formula (A1).

In another preferred embodiment, the presently claimed invention is directed to a process for preparing a compound of formula (A2) comprising the steps of iii) reacting the compound of formula (E2) obtained according to step ii) with thionyl chloride to obtain a compound of formula (F2)

formula (A2)

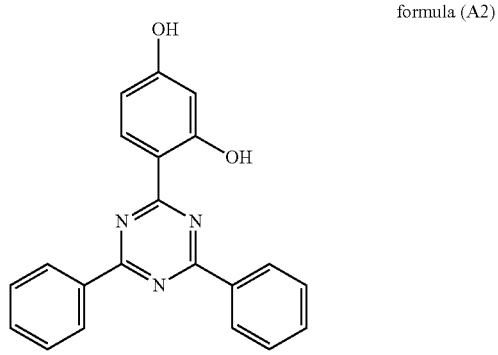 [SMILES: Oc1ccc(-c2nc(-c3ccccc3)nc(-c3ccccc3)n2)c(O)c1]

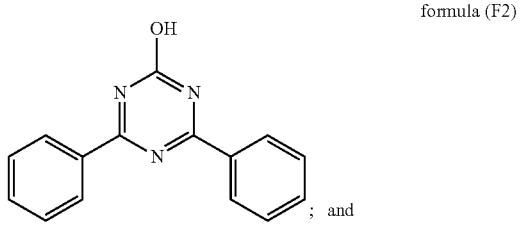 [SMILES: Oc1nc(-c2ccccc2)nc(-c2ccccc2)n1]
formula (F2)

iv) reacting the compound of formula (F2) obtained according to step iii) with at least one compound of formula (G1),

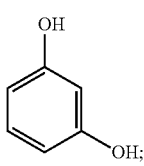
formula (G1)

in the presence of AlCl$_3$ to obtain the compound of formula (A2).

In another preferred embodiment, the presently claimed invention is directed to a process for preparing a compound of formula (A3) comprising the steps of

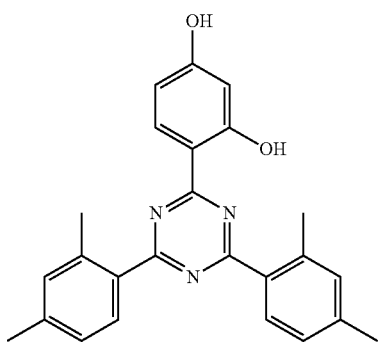
formula (A3)

i) reacting a compound of formula (C1)

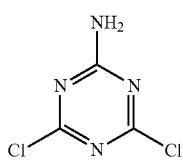
formula (C1)

with a compound of formula (B1c)

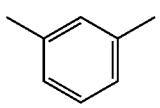
formula (B1c)

in the presence of AlCl$_3$ to obtain a compound of formula (D3)

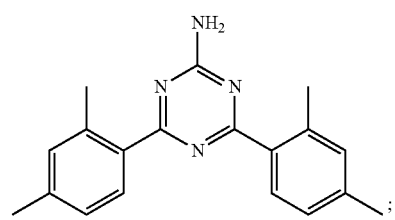
formula (D3)

ii) reacting the compound of formula (D3) obtained according to step i) with sodium hydroxide to obtain a compound of formula (E3)

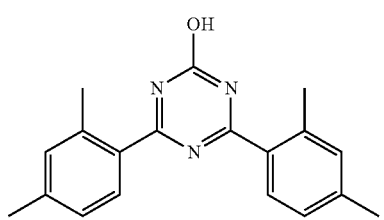
formula (E3)

iii) reacting the compound of formula (E3) obtained according to step ii) with thionyl chloride to obtain a compound of formula (F3)

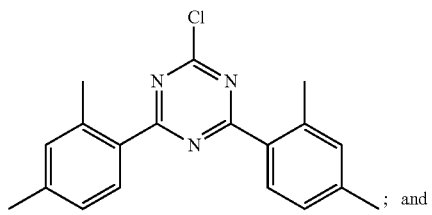
formula (F3)

iv) reacting the compound of formula (F3) and a compound of formula (G1),

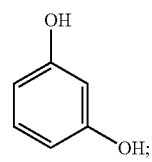
formula (G1)

in the presence of AlCl$_3$ to obtain the compound of formula (A3).

In another preferred embodiment, the presently claimed invention is directed to a process for preparing a compound of formula (A4)

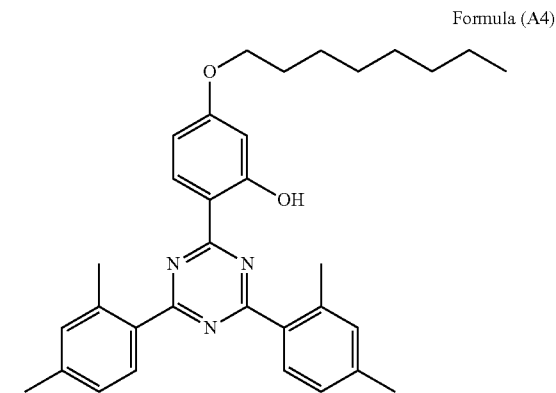 [SMILES: CCCCCCCCOc1ccc(-c2nc(-c3ccc(C)cc3C)nc(-c3ccc(C)cc3C)n2)c(O)c1]
Formula (A4)

comprising reacting a compound of formula (A3) in the presence of NaOH with 1-bromooctane to obtain the compound of formula (A4).

In another preferred embodiment, the presently claimed invention is directed to a process for preparing a compound of formula (A9)

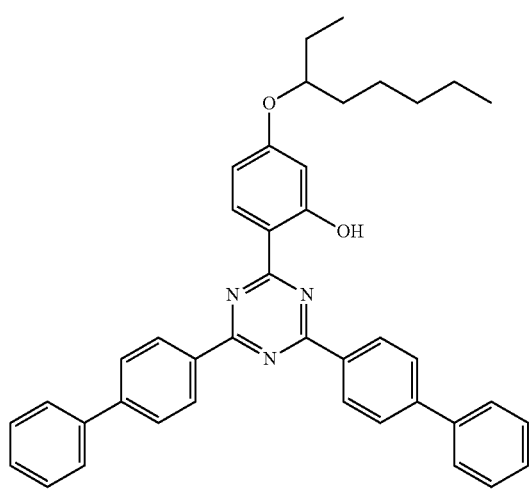

formula (A9)

comprising reacting a compound of formula (A1) in the presence of NaOH with 3-bromooctane to obtain the compound of formula (A9).

In another preferred embodiment, the presently claimed invention is directed to a process for preparing a compound of formula (A12 and A12a)

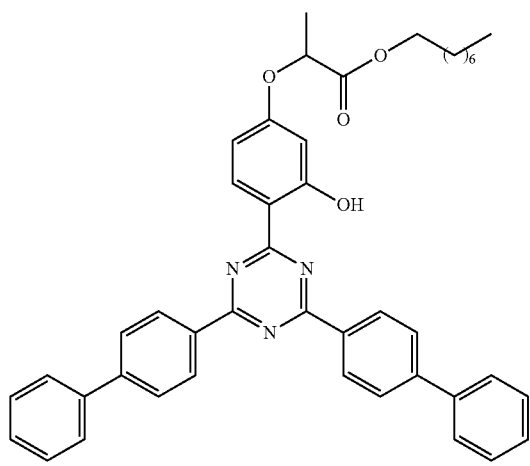

formula (A12)

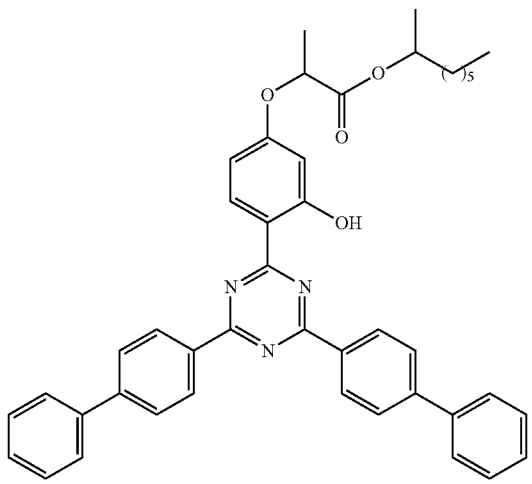

formula (A12a)

comprising reacting a compound of formula (A1) in the presence of NaOH with octyl α-bromopropionate along with other isomers of octyl bromopropinonate to obtain the compound of formula (A12 & A12a).

In another preferred embodiment, the presently claimed invention is directed to a process for preparing a compound of formula (A10)

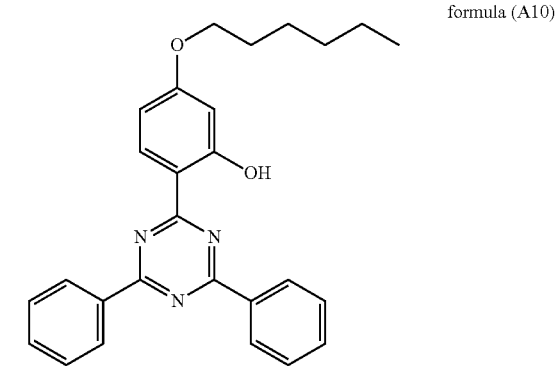 [SMILES: CCCCCCOc1ccc(-c2nc(-c3ccccc3)nc(-c3ccccc3)n2)c(O)c1]

formula (A10)

comprising reacting a compound of formula (A2) in the presence of NaOH with bromohexane to obtain the compound of formula (A10).

In another preferred embodiment, the presently claimed invention is directed to a process for preparing a compound of formula (A11)

formula (A11a)

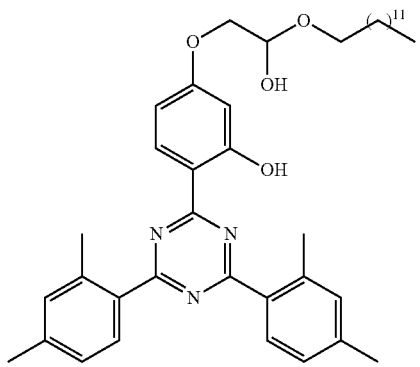

formula (A11b)

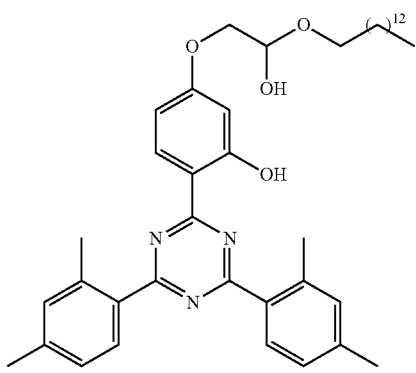

comprising reacting a compound of formula (A3) in the presence of NaOH with alkylhalide of formula (M1) to obtain the compound of formula (A11a and A11b)

formula(M1)

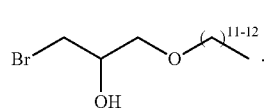

In another preferred embodiment, the presently claimed invention is directed to a process for preparing a compound of formula (A8)

formula (A8)

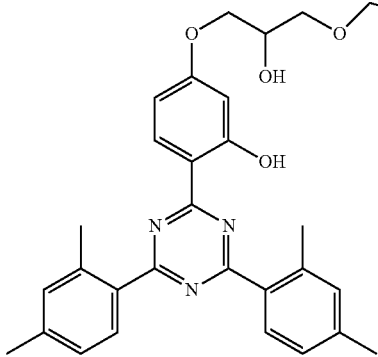

comprising reacting a compound of formula (A3) in the presence of NaOH with alkylhalide of formula (M2) to obtain the compound of formula (A8)

formula(M2)

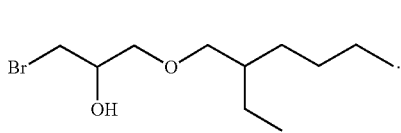

The advantages of the process of the presently claimed invention are as follows:
i) the process is commercially viable and highly cost effective; and
ii) the process provides the final product without any colour imparting impurities.

In the following, there is provided a list of embodiments to further illustrate the present disclosure without intending to limit the disclosure to the specific embodiments listed below.

Embodiments

1. A process for preparing a compound of formula (A)

formula (A)

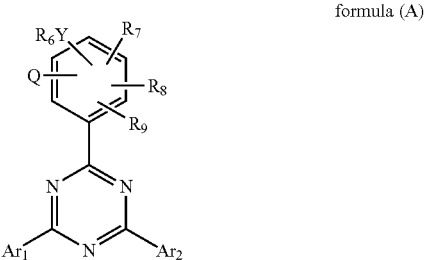

wherein $Ar_1$ and $Ar_2$ are independently a moiety of the formula (B), formula (B)

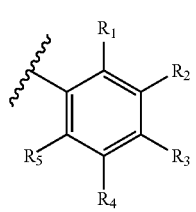

wherein
$R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O)NRR', CN, SR, S(=O)$_2$R, S(=O)$_2$OH and S(=O)$_2$OM; wherein M is an alkali metal; or
$R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s);

Q is selected from hydrogen and OH;

$R_6$ is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OC(=O)R, CN, SR, S(=O)$_2$R, S(=O)$_2$OH and S(=O)$_2$OM, wherein M is an alkali metal, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen, O, —NR″, or S, wherein R″ is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of:

i) reacting at least one compound of formula (C)

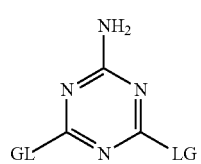

formula (C)

wherein LG is halogen, O—S(=O)$_2$CF$_3$ or O—S(=O)$_2$CH$_3$;

with at least one compound of formula (B1)

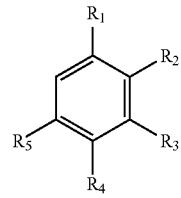

formula (1B)

wherein $R_1$, $R_2$, $R_3$, $R_4$ and $R_5$ are defined as above;

in the presence of at least one acid to obtain a compound of formula (D)

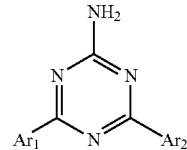

formula (D)

wherein $Ar_1$ and $Ar_2$ are defined as above;

ii) reacting the compound of formula (D) obtained according to step i) with at least one metal hydroxide to obtain a compound of formula (E)

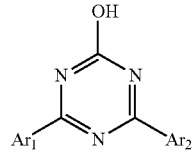

formula (E)

wherein $Ar_1$ and $Ar_2$ are defined as above;

iii) reacting the compound of formula (E) obtained according to step ii) with at least one halogenating reagent to obtain a compound of formula (F)

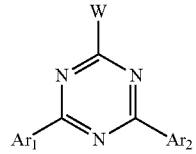

formula (F)

wherein $Ar_1$ and $Ar_2$ are defined as above, and

W is selected from the group consisting of F, Cl, and Br; and iv) reacting at least one compound of formula (F) obtained according to step iii) and at least one compound of formula (G),

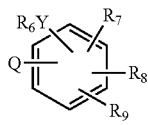

formula (G)

wherein Y, Q, $R^6$, $R^7$, $R^8$ and $R^9$ are defined as above, in the presence of an at least one acid to obtain a compound of formula (A).

2. The process according to embodiment 1, comprising a step of:

v). reacting the product obtained according to step iv) with at least one alkyl halide or at least one acyl halide in the presence of a base to obtain a compound of formula (A).

3. The process according to embodiment 1, wherein in step (i) the at least one acid is selected from the group consisting of inorganic acids, Lewis acids, and organic acids.

4. The process according to embodiment 3, wherein in step (i) the inorganic acids are selected from the group consisting of sulfuric acid, hydrochloric acid, phosphoric acid, perchloric acid, nitric acid, nitrous acid, sulphurous acid, chloric acid, chlorous acid and hypochlorous acid.

5. The process according to embodiment 4, wherein in step (i) the Lewis acids are selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—S(=O)$_2$O, $CH_3$—S(=O)$_2$O, or I;

$BH_3$, $B(CH_3)_3$, $GaH_3$, $AlH_3$, Al (acetate)(OH)$_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-bromo-2,6-di-tert-butylphenoxide), $LiClO_4$; Mg(acetate)$_2$, Zn (acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg (acetate)$_2$, Ag(acetate), Tl(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$.

6. The process according to embodiment 5, wherein in step (i) the at least one Lewis acid is selected from the group consisting of $BX_3$, $BX_3 \cdot (C_2H_5)_2O$, $BX_3 \cdot S(CH_3)_2$, $AlX_3$, $ZnX_2$, $FeX_3$ and $TiX_4$, whereby X in each case denotes F, Cl, or Br.

7. The process according to embodiment 2, wherein in step (i) the organic acids are selected from the group consisting of organic carboxylic acid, organic phosphoric acid and organic sulfonic acid.

8. The process according to embodiment 1, wherein in step (i) the molar ratio of the at least one acid to the at least one compound of formula (C) is in in the range of 1:10 to 10:1.

9. The process according to embodiment 1, wherein in step (i) the molar ratio of the at least one compound of formula (B1) to the at least one compound of formula (C) is in the range of 1:1 to 5:2.

10. The process according to embodiment 1, wherein in step (i) the at least one compound of formula (C) and the at least one compound of formula (B1) are reacted in the presence of at least one solvent selected from the group consisting of aliphatic hydrocarbons, aliphatic acyclic ether, aliphatic cyclic ether and carbon disulfide.

11. The process according to embodiment 10, wherein in step (i) the molar concentration of the at least one compound of formula (C) in the at least one solvent is in the range of 0.5 M to 8.0 M.

12. The process according to embodiment 10, wherein in step (i) the molar concentration of the at least one compound of formula (B1) in the at least one solvent is in the range of 0.5 M to 8.0 M.

13. The process according to embodiment 10, wherein in step (i) the aliphatic cyclic ether is dioxane.

14. The process according to embodiment 1, wherein in step (i) the at least one compound of formula (C) and the at least one compound of formula (B1) are reacted at a temperature in the range of 0° C. to 250° C.

15. The process according to embodiment 1, wherein in step (i) the at least one compound of formula (C) and the at least one compound of formula (B1) are reacted for a period in the range of 30 minutes to 24 hours.

16. The process according to embodiment 1, wherein in step ii) the at least one metal hydroxide is selected from the group consisting of NaOH, KOH, LiOH, Cs(OH), Be(OH)$_2$, Mg(OH)$_2$, Ca(OH)$_2$, Sr(OH)$_2$, Ba(OH)$_2$, and Al(OH)$_3$.

17. The process according to embodiment 16, wherein in step ii) the at least one metal hydroxide is selected from the group consisting of NaOH and KOH.

18. The process according to embodiment 1, wherein in step (ii) the molar ratio of the at least one metal hydroxide to the at least one compound of formula (D) is in in the range of 1:1 to 10:1.

19. The process according to embodiment 1, wherein in step iii) the at least one halogenating agent is selected from the group consisting of thionyl chloride, thionyl bromide, phosphorus pentachloride, phosphorous trichloride and phosphorus oxychloride.

20. The process according to embodiment 19, wherein in step iii) the at least one halogenating agent is selected from the group consisting of thionyl chloride, phosphorus pentachloride, and phosphorous trichloride.

21. The process according to embodiment 1, wherein in step iv) the at least one acid is a Lewis acid selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2$—$O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3$—S(=O)$_2$O, $CH_3$—S(=O)$_2$O, or I;

$BH_3$, $B(CH_3)_3$, $GaH_3$, $AlH_3$, Al (acetate)(OH)$_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-bromo-2,6-di-tert-butylphenoxide), $LiClO_4$; Mg(acetate)$_2$, Zn (acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, Sc(trifluoromethanesulfonate)$_3$, Ln(trifluoromethanesulfonate)$_3$, Ni(trifluoromethanesulfonate)$_2$, Ni(tosylate)$_2$, Co(trifluoromethanesulfonate)$_2$, Co(tosylate)$_2$, Cu(tri-fluoromethanesulfonate)$_2$ and Cu(tosylate)$_2$.

22. The process according to embodiment 21, wherein in step iv) the at least one Lewis acid is selected from the group consisting of BX$_3$, BX$_3$·(C$_2$H$_5$)$_2$O, BX$_3$·S(CH$_3$)$_2$, AlX$_3$, ZnX$_2$ and TiX$_4$, whereby X in each case denotes F, Cl, or Br.

23. The process according to embodiment 1, wherein in step iv) the molar ratio of the at least one acid to the at least one compound of formula (G) is in in the range of 1:10 to 10:1.

24. The process according to embodiment 1, wherein in step iv) the molar ratio of the at least one acid to the at least one compound of formula (F) is in in the range of 1:10 to 10:1.

25. The process according to embodiment 1, wherein in step iv) the molar ratio of the at least one compound of formula (G) to the at least one compound of formula (F) is in in the range of 2:5 to 5:2.

26. The process according to embodiment 1, wherein in step iv) the at least one compound of formula (G) and the at least one compound of formula (F) are reacted in the presence of at least one solvent selected from the group consisting of aliphatic and aromatic hydrocarbons, halogenated aliphatic, halogenated aromatic hydrocarbons, ethers and carbon disulphide.

27. The process according to embodiment 26, wherein in step iv) the aliphatic cyclic ether is dioxane.

28. The process according to embodiment 1, wherein in step iv) the reaction is carried out at a temperature in the range of 0 to 250° C.

29. The process according to embodiment 1, wherein in step iv) the at least one compound of formula (F) and the at least one compound of formula (G) are reacted for a period of 30 minutes to 24 hours.

30. The process according to embodiment 1, wherein R$_1$, R$_2$, R$_3$, R$_4$ and R$_5$ are independently selected from the group consisting of hydrogen, halogen, substituted or unsubstituted, linear or branched C$_1$-C$_{24}$ alkyl, substituted or unsubstituted C$_6$-C$_{24}$ aryl, C(=O)R and OR, wherein R is selected from the group consisting of hydrogen, substituted or unsubstituted, linear or branched C$_1$-C$_{24}$ alkyl, substituted or unsubstituted, linear or branched C$_2$-C$_{24}$ alkenyl, substituted or unsubstituted C$_5$-C$_{24}$ cycloalkyl, substituted or unsubstituted C$_5$-C$_{24}$ cycloalkenyl, substituted or unsubstituted C$_6$-C$_{24}$ aryl and substituted or unsubstituted C$_7$-C$_{24}$ arylalkyl.

31. The process according to embodiment 30, wherein R$_1$, R$_2$, R$_3$, R$_4$ and R$_5$ are independently selected from the group consisting of hydrogen, substituted or unsubstituted, linear or branched C$_1$-C$_{24}$ alkyl, substituted or unsubstituted C$_6$-C$_{24}$ aryl, OR;
wherein R is hydrogen or substituted or unsubstituted, linear or branched C$_1$-C$_{24}$ alkyl.

32. The process according to embodiment 31, wherein R$_1$, R$_2$, R$_3$, R$_4$ and R$_5$ are independently selected from the group consisting of hydrogen, methyl, substituted or unsubstituted phenyl, OR;
wherein OR is selected from the group consisting of OH, OCH$_3$, OC$_8$H$_{17}$.

33. The process according to embodiment 1, wherein
R$_6$ is selected from hydrogen, substituted or unsubstituted, linear or branched C$_1$-C$_{24}$ alkyl and substituted or unsubstituted C$_6$-C$_{24}$ aryl;
Y is selected from hydrogen and O; with the proviso that in case Y is hydrogen, then R$_6$ is not present;
T is selected from hydrogen or OH; and
R$_7$, R$_8$ and R$_9$ is selected from hydrogen, substituted or unsubstituted, linear or branched C$_1$-C$_{24}$ alkyl, substituted or unsubstituted C$_6$-C$_{24}$ aryl, C(=O)R, OR, OC(=O)R; wherein R is independently selected from the group consisting of hydrogen, substituted or unsubstituted, linear or branched C$_1$-C$_{24}$ alkyl.

34. The process according to anyone of the preceding embodiment s, where the compound of formula (A) or the UV absorber compounds are selected from the group consisting of:

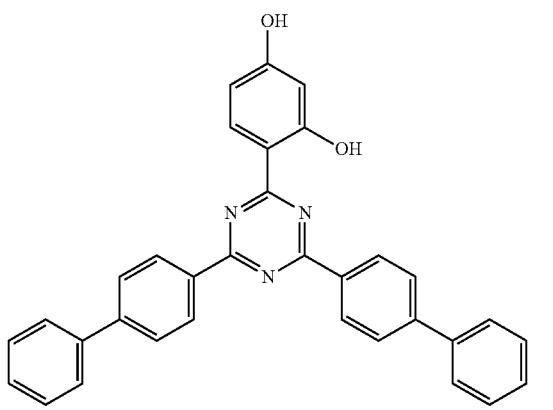

formula (A1)

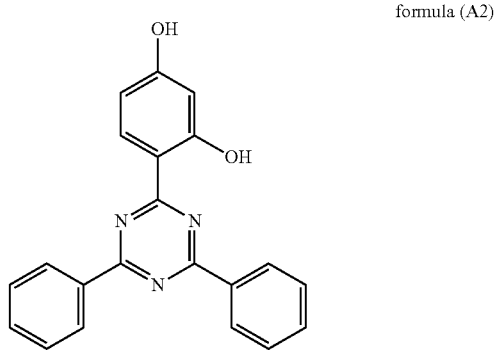

formula (A2)

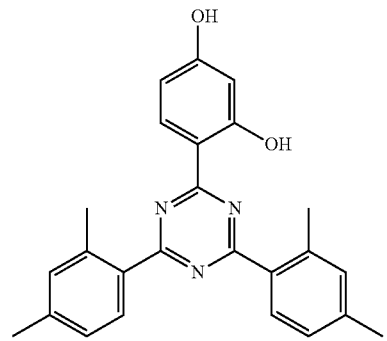

formula (A3)

formula (A4)
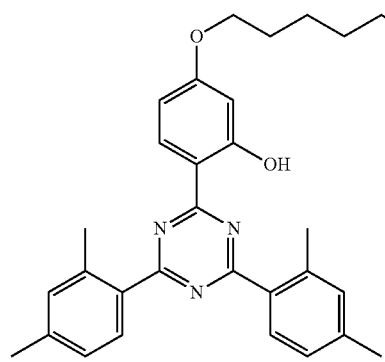
formula (A5)
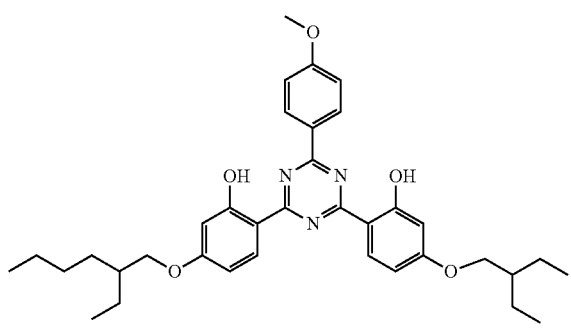
formula (A6)
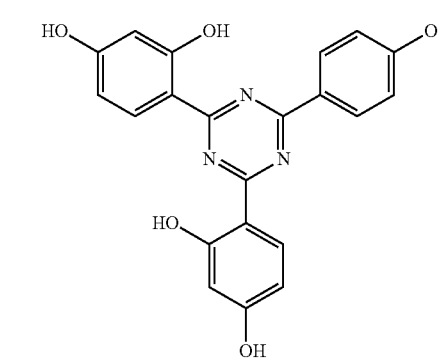
formula (A8)
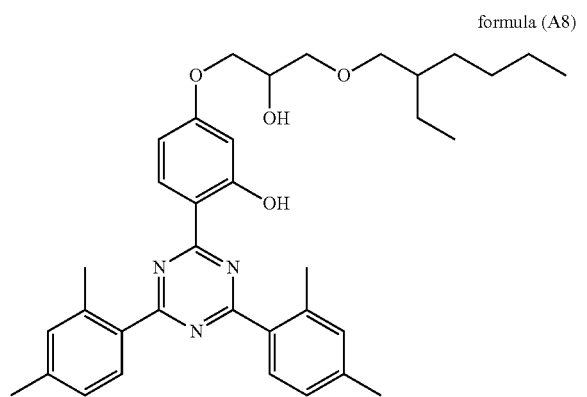
formula (A9)
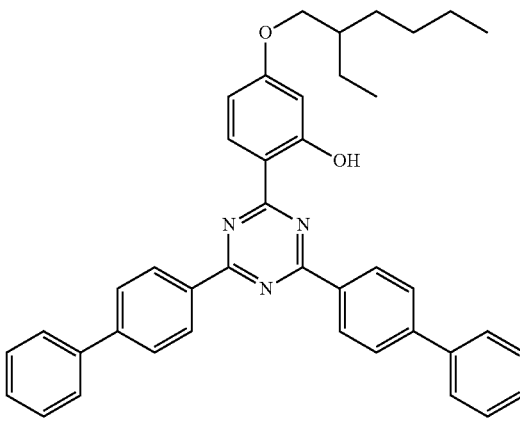
formula (A10)
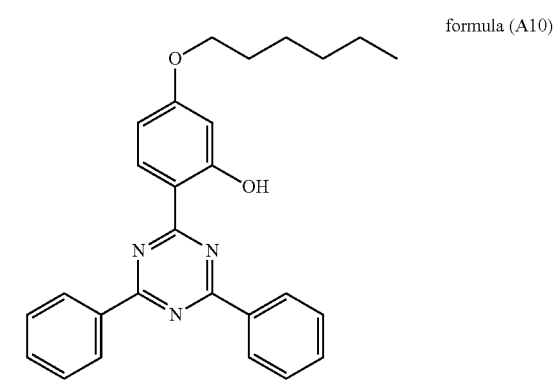
formula (A11a)
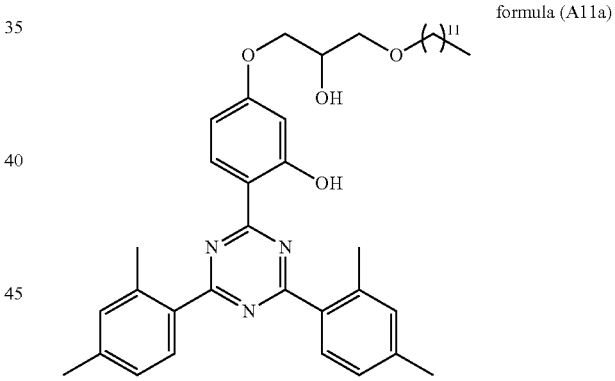
formula (A11b)
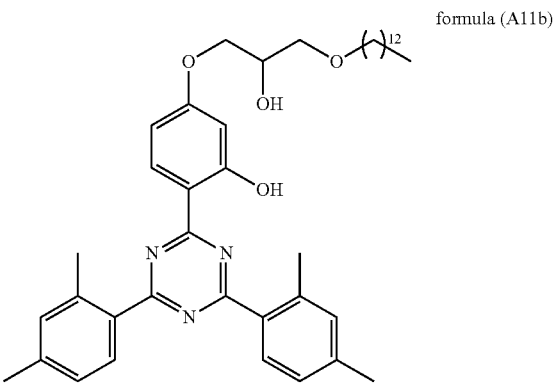

-continued formula (A12)

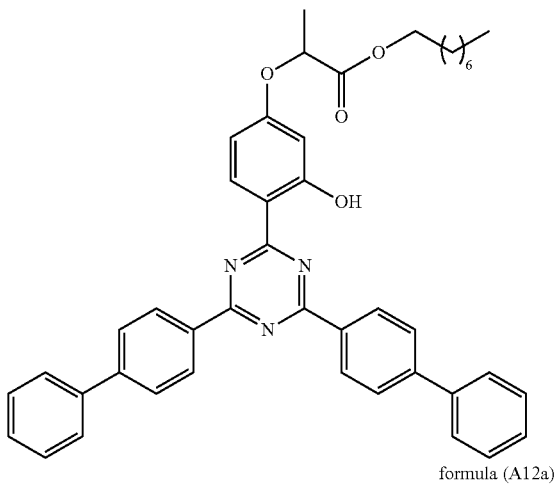

formula (A12a)

While the presently claimed invention has been described in terms of its specific embodiments, certain modifications and equivalents will be apparent to those skilled in the art and are intended to be included within the scope of the presently claimed invention Examples The presently claimed invention is illustrated in detail by non-restrictive working examples which follow. More particularly, the test methods specified hereinafter are part of the general disclosure of the application and are not restricted to the specific working examples.

Materials:

Trichlorotriazine, o-dichlorobenzene, N,N-dimethyl formamide, resorcinol, biphenyl, xylene, Octyl α-bromopropionate isomix, bromohexane, etc. are available from Sigma Aldrich.

Synthesis of 2-Amino-4,6-chloro-1,3,5-triazine (C1)

A hot suspension of trichlorotriazine (20 g, 0.108 mol) in 50 mL of acetone was added under stirring to 100 g of crushed ice in water. 22 g of a 25 wt % aqueous ammonia solution was added to the above suspension while maintaining a temperature below 0° C. The suspension was stirred until the temperature reached to 5° C. and filtrated. The crude product was recrystallized from water and dried at room temperature to obtain the compound of formula (C1). Yield: 16 g (89%), white solid.

Synthesis of 4,6-bis(4-phenylphenyl)-1,3,5-triazin-2-amine (D1)

AlCl$_3$ (24.4 g, 183 mmol) was added to a solution of compound of formula (C1) (10 g, 61 mmol) in o-dichlorobenzene (50 mL) and the resultant mixture was heated to 50°. A solution of biphenyl (19.6 g, 127 mmol) in o-dichlorobenzene (ODCB, 40 mL) at 80° C. was added to the solution obtained above. After completion of the addition of biphenyl, the temperature of the reaction mixture was raised to 110° C. followed by stirring for 3 hours. The hot reaction mass was quenched by pouring into ice-cold water to obtain a suspension. The crude product precipitated and it was isolated by filtration. The crude precipitated product was stirred in heptane (50 mL) for 1 hr, filtered and dried to obtain the compound of formula (D1). Yield: 20.8 g (87%)

Synthesis of 4,6-bis(4-phenylphenyl)-1,3,5-triazin-2-ol (E1)

A mixture of 4,6-bis(4-phenylphenyl)-1,3,5-triazin-2-amine (D1) (3 g, 12 mmol) in 2-butoxy ethanol (15 g) was heated to 145-150° C. Solid NaOH (1.92 g, 48 mmol) was added to the above mixture portion wise. After completion of the addition of NaOH, the reaction mixture was maintained at 145-150° C. for 3 hours. After completion of the reaction, the mixture was cooled to 80° C. and quenched by water. Conc. HCl was added dropwise, until the pH of the solution was between 1 to 2. The organic layer was separated, and the product was isolated, washed with MeOH and dried under vacuum to obtain 4,6-bis(4-phenylphenyl)-1,3,5-triazin-2-ol (E1). Yield: 2.4 g (80%, white Solid); $^1$H NMR: (300 MHz, CDCl$_3$)-δ 8.446-8.421 (d, 4H), 7.721-7.580 (m, 6H), 13.150 (s, 1H); LCMS (m/z): 250.05 [m+1]

Synthesis of 2-chloro-4,6-bis(4-phenylphenyl)-1,3,5-triazine (F1)

A mixture of 4,6-bis(4-phenylphenyl)-1,3,5-triazin-2-ol (E1) (2 g, 8 mmol) in o-dichlorobenzene (10 g) was heated to 85° C. and DMF (0.2 g) was added in one lot. To the above solution thionyl chloride (2.84 g, 24 mmol) was added dropwise, while maintaining the temperature at 80-85° C. After completion of the addition of thionyl chloride, the temperature of the reaction mixture was maintained for 2 hours. After completion of the reaction, the excess thionyl chloride was distilled off, heptane (30 g) was added and the reaction mixture was cooled to room temperature. The precipitated solid was filtered, washed with cold methanol (10 g) and dried under vacuum to obtain 2-chloro-4,6-bis(4-phenylphenyl)-1,3,5-triazine (F1). Yield: 1.8 g (84%); $^1$H NMR: (300 MHz, CDCl$_3$)-δ 8.565-8.540 (d, 4H), 7.761-7.614 (m, 6H); LCMS (m/z): 267.75 [m+1]

Synthesis of 4-[4,6-bis(4-phenylphenyl)-1,3,5-triazin-2-yl]benzene-1,3-diol (A1)

AlCl$_3$ (34.8 g, 262 mmol) was added in one portion to a solution of 2-chloro-4,6-bis(4-phenylphenyl)-1,3,5-triazine (F1) (100 g, 238 mmol) in o-dichlorobenzene (300 mL) and the resulting mixture was heated to 50° C. to obtain a suspension. Resorcinol (G1, 41.8 g, 380 mmol) was added to this suspension portion-wise at 80° C. After completion of the addition, the temperature of the reaction mixture was raised to 110° C. followed by stirring for 3 hours. The hot reaction mass was quenched by adding to a solution of 10% HCl at 90° C. The precipitated crude product was filtered. The crude product was mixed with heptane (50 mL) and stirred for 1 hr, filtered and dried to obtain the 4-[4,6-bis(4-phenylphenyl)-1,3,5-triazin-2-yl]benzene-1,3-diol (A1). Yield: 96.5 g (82%).

Synthesis of 4,6-diphenyl-1,3,5-triazin-2-amine (D2)

$AlCl_3$ (24.4 g, 183 mmol) was added to a solution of the compound of formula (C1) (10 g, 61 mmol) in o-dichlorobenzene (50 mL) and heated to 50° C. A solution of benzene (28.3 g, 363 mmol) in ODCB (40 mL) at 80° C. was added to the solution obtained above. After completion of addition of biphenyl, the temperature of the reaction mixture was raised to 110° C. followed by stirring for 3 hours. The hot reaction mass was quenched by pouring into ice-cold water. The crude product precipitated out and was filtered off. The crude precipitated product was stirred in heptane (50 mL) for 1 hr, filtered and dried to obtain compound of formula (D2). Yield: 20.8 g (87%).

Synthesis of 4,6-diphenyl-1,3,5-triazin-2-ol (E2)

The reaction was conducted under conditions similar to the preparation of compound (E1). Yield: 2.4 g (80%, White Solid); $^1$H NMR: (300 MHz, $CDCl_3$)-δ 8.446-8.421 (d, 4H), 7.721-7.580 (m, 6H), 13.150 (s, 1H); LCMS (m/z): 250.05 [m+1]

Synthesis of 2-chloro-4,6-diphenyl-1,3,5-triazine (F2)

The reaction was conducted under conditions similar to the preparation of compound (F1). Yield: 1.8 g (84%, White solid); $^1$H NMR: (300 MHz, $CDCl_3$)-δ 8.565-8.540 (d, 4H), 7.761-7.614 (m, 6H); LCMS (m/z)-267.75 [m+1]

Synthesis of 4-(4,6-diphenyl-1,3,5-triazin-2-yl)benzene-1,3-diol (A2)

The reaction was conducted under conditions similar to the preparation of compound (A1) to obtain a compound of formula (A2). Yield: 54.6 g (86%).

Synthesis of 4,6-bis(2,4-dimethylphenyl)-1,3,5-triazin-2-amine (D3)

$AlCl_3$ (51.4 g, 0.363 mol) was added to a solution of a compound of formula (C1) (20 g, 0.121 mol) in o-dichlorobenzene (200 mL) and heated to 50°. A solution of 1,3-xylene (0.484 mol) at 80° C. was added to the solution obtained above. After completion of addition of biphenyl, the temperature was raised to 110° C. and for the reaction mixture was stirred for 3 hrs. The hot reaction mass was quenched by pouring into ice-cold water. The product was extracted using chloroform. The crude product was obtained after evaporation of chloroform to obtain a precipitate. The crude precipitate was stirred in heptane (50 mL) for 1 hr, filtered and dried to obtain compound of formula (D3). Yield: 32.8 g (88%, Buff coloured solid); $^1$H NMR: (300 MHz, $CDCl_3$)-δ 7.812-7.840 (d, 2H), 7.576 (s, 2H), 7.101-7.122 (m, 4H), 2.501-2.507 (s, 6H), 2.311 (s, 6H); LCMS (m/z): 304.1 [m+1]

Synthesis of 4,6-bis(2,4-dimethylphenyl)-1,3,5-triazin-2-ol (E3)

The reaction was conducted under conditions similar to the preparation of compound (E1). Yield: 3.9 g (77.8%); $^1$H NMR: (300 MHz, $CDCl_3$)-δ 7.7-7.8 (d, 2H), 7.1-7.3 (m, 4H), 13.4-13.6 (s, 1H), 2.31 (s, 6H), 2.52 (s, 6H); LCMS (m/z): 306.1 [m+1].

Synthesis of 2-chloro-4,6-bis(2,4-dimethylphenyl)-1,3,5-triazine (F3)

The reaction was conducted under conditions similar to the preparation of compound (F1). Yield: 2.6 g (82%); $^1$H NMR: (300 MHz, $CDCl_3$)-δ 8.082-8.056 (d, 2H), 7.174-7.061 (m, 4H), 2.639 (s, 6H), 2.315 (s, 6H), 2.639 (s, 6H); LCMS (m/z)-324.2 [m+1].

Synthesis of 4-[4,6-bis(2,4-dimethylphenyl)-1,3,5-triazin-2-yl]benzene-1,3-diol (A3)

The reaction was conducted under conditions similar to the preparation of compound (A1) to obtain a compound of formula (A3). Yield: 90%

Synthesis of 2-(4,6-bis(2,4-dimethylphenyl)-1,3,5-triazin-2-yl)-5-(octyloxy)phenol (A4)

To a stirred solution of a compound formula (A3) (0.2 mol) in DMF (250 g) was added sodium hydroxide (0.1 mol). The temperature was raised to 70° C., octyl bromide (0.2 mol) was added dropwise. The reaction was continued at this temperature 4-5 h. After the reaction was completed, the reaction mixture was cooled, submitted to suction filtration and recrystallized to obtain a compound of formula (A4).

Synthesis of 4-[4-amino-6-(2,4-dihydroxyphenyl)-1,3,5-triazin-2-yl]benzene-1,3-diol (D6)

A compound of formula (C1) (2 g, 12.1 mmol) was taken in o-dichlorobenzene (20 mL). $AlCl_3$ (3.4 g, 30 mmol) was added in one portion and the reaction mixture was heated to 50° C. for 15 min. Resorcinol (8 g, 25 mmol) was added in 3 portions and simultaneously the temperature was increased to 70° C. The reaction mixture was heated to 100° C. for 2 hrs. After 2 hrs, the reaction mixture was cooled to room temperature and water was added. The product was precipitated, filtered, washed with water and dried under vacuum. Yield: 3.6 g (94.7%); $^1$H NMR: (300 MHz, $D_2O$)-δ 8.14-8.01 (d, 2H), 6.44-6.41 (m, 2H), 6.3 (s, 2H); LCMS (m/z)-312.8 [m+1].

Synthesis of 4-[4-(2,4-dihydroxyphenyl)-6-hydroxy-1,3,5-triazin-2-yl]benzene-1,3-diol (E6)

The reaction was conducted under conditions similar to the preparation of compound (E1). Yield: 1.4 g (56%); 1H NMR: (300 MHz, DMSO)-δ 10.66 (br s), 8.12-8.10 (d, 2H), 6.52-6.6.39 (m, 4H); LCMS (m/z)-314 [m+1].

Synthesis of 4-[4-chloro-6-(2,4-dihydroxyphenyl)-1,3,5-triazin-2-yl]benzene-1,3-diol (F6)

The reaction was conducted under conditions similar to the preparation of compound (F1). Yield: 80 mg (yellow solid); 1H NMR: (300 MHz, DMSO)-δ 12.25 (br s, 2H), 10.59 (br s, 2H), 8.13-8.10 (m, 2H), 6.49-6.6.47 (m, 2H), 6.40-6.6.38 (m, 2H); LCMS (m/z)-331.75 [m−1].

Synthesis of 4-[4-(2,4-dihydroxyphenyl)-6-(4-methoxyphenyl)-1,3,5-triazin-2-yl]benzene-1,3-diol (A6)

The reaction was conducted under conditions similar to the preparation of compound (A1) to obtain a compound of formula (A6). Yield: 60%

Synthesis of Compound of Formula (A5)

To a stirred solution of the compound of formula (A6) (0.2 mol) in DMF (250 g) was added sodium hydroxide (0.1 mol). The temperature was raised to 70° C., 3-bromo octane (0.2 mol) was added dropwise. The reaction was continued at this temperature for 4-5 h, after the reaction was completed, the reaction mixture was cooled, submitted to suction filtration and recrystallized to obtain a compound of formula (A5).

Synthesis of Compound of Formula (A11a & A11b)

To a stirred solution of compound formula (A3) (0.2 mol) in DMF (250 g) was added sodium hydroxide (0.1 mol). The temperature was raised to 70° C., alkyl bromide of formula (M1) (0.2 mol) was added dropwise. The reaction was continued at this temperature for 4-5 h. After the reaction was completed, the reaction mixture was cooled, submitted to suction filtration and recrystallized to obtain a compound of formula (A11a and A11b).

Synthesis of 2-(4,6-bis(2,4-dimethylphenyl)-1,3,5-triazin-2-yl)-5-(3-((2-ethylhexyl)oxy)-2-hydroxypropoxy)phenol (A8)

To a stirred solution of compound formula (A3) (0.2 mol) in DMF (250 g) was added sodium hydroxide (0.1 mol). The temperature was raised to 70° C., alkyl bromide of formula (M2) (0.2 mol) was added dropwise. The reaction was continued at this temperature for 4-5 h. After the reaction was completed, the reaction mixture was cooled, submitted to suction filtration and recrystallized to obtain a compound of formula (A8).

Synthesis of Compound of Formula (A9)

To a stirred solution of compound formula (A1) (0.2 mol) in DMF (250 g) was added sodium hydroxide (0.1 mol). The temperature was raised to 70° C., 3-bromo octane (0.2 mol) was added dropwise. The reaction was continued at this temperature for 4-5 h. After the reaction was completed, the reaction mixture was cooled, submitted to suction filtration and recrystallized to obtain a compound of formula (A9).

Synthesis of Compound of Formula (A10)

Bromohexane (33 g, 0.2 mol) was added dropwise to a mixture of compound of formula (A2) (70 g, 0.2 mol) and sodium hydroxide (4 g, 0.1 mol) in DMF (250 g) at 70° C. The reaction mixture was stirred at this temperature for 4-5 hours. The reaction mixture was cooled and filtered. The crude product was crystallized to give compound of formula (A10). Yield 78.5 g (90%)

Synthesis of Compound of Formula (A12 and A12a)

Octyl α-bromopropionate and isomers of octyl bromopropoionate (18.5 g, 0.07 mol) were added dropwise to a mixture of 4-[4,6-bis(4-phenylphenyl)-1,3,5-triazin-2-yl]benzene-1,3-diol (A1) (35 g, 0.07 mol) and sodium hydroxide (2 g, 0.05 mol) in DMF (120 g) at 70° C. The reaction mixture was stirred at this temperature for 4-5 hours. The reaction mixture was cooled and filtered. The crude product was crystallized to give compound of formula (A12 and A12a). Yield 40.3 g (85%).

The invention claimed is:
1. A process for preparing a compound of formula (A)

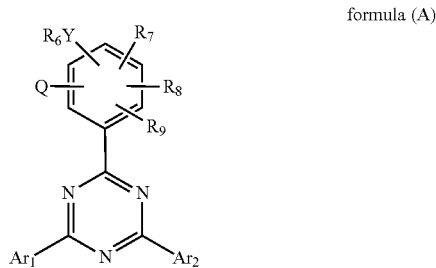

formula (A)

wherein $Ar_1$ and $Ar_2$ are independently a moiety of the formula (B),

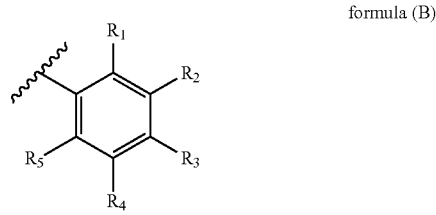

formula (B)

wherein
$R_1, R_2, R_3, R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, C(=O)R, OR, NRR', C(=O) NRR', CN, SR, S(=O)$_2$R, S(=O)$_2$OH and S(=O)$_2$OM; wherein M is an alkali metal; or
$R_1$ and $R_2$ together with the carbon atoms to which they are bonded or
$R_2$ and $R_3$ together with the carbon atoms to which they are bonded or
$R_3$ and $R_4$ together with the carbon atoms to which they are bonded or
$R_4$ and $R_5$ together with the carbon atoms to which they are bonded form an unsaturated or aromatic 5- to 20-membered carbocyclic ring that optionally contains 1, 2 or 3 heteroatom(s) selected from O, N or S as ring member(s);
Q is selected from hydrogen and OH;
$R_6$ is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl, and C(=O)R;

$R_7$, $R_8$ and $R_9$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl, substituted or unsubstituted $C_5$-$C_{24}$ cycloalkenyl, C(=O)R, OR, NRR', C(=O)NRR', OC(=O)R, CN, SR, S(=O)$_2$R, S(=O)$_2$OH and S(=O)$_2$OM, wherein M is an alkali metal, or $R_7$ and $R_8$ together with the carbon atoms to which they are bonded form an unsaturated or aromatic 5- to 20-membered carbocyclic ring that optionally contains 1, 2 or 3 heteroatom(s) selected from O, N or S as ring member(s);

Y is selected from the group consisting of hydrogen, halogen, O, —NR", or S, wherein R" is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, substituted or unsubstituted $C_5$-$C_{24}$ cycloalkyl and substituted or unsubstituted $C_5$-$C_{24}$ cycloalkenyl; with the proviso that in case Y is hydrogen or halogen, then $R_6$ is not present; and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

comprising at least the steps of:
i) reacting at least one compound of formula (C)

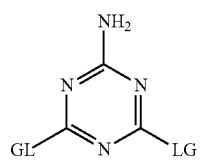

formula (C)

wherein LG is halogen, O—S(=O)$_2$CF$_3$ or O—S(=O)$_2$CH$_3$;
with at least one compound of formula (B1)

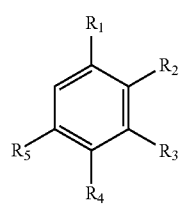

formula (B1)

wherein $R_1$, $R_2$, $R_3$, R and $R_5$ are defined as above;

in the presence of at least one acid to obtain a compound of formula (D)

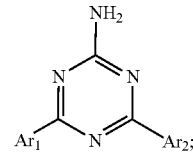

formula (D)

wherein Ar$_1$ and Ar$_2$ are defined as above;
ii) reacting the compound of formula (D) obtained according to step i) with at least one metal hydroxide to obtain a compound of formula (E)

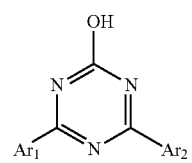

formula (E)

wherein Ar$_1$ and Ar$_2$ are defined as above;
iii) reacting the compound of formula (E) obtained according to step ii) with at least one halogenating reagent to obtain a compound of formula (F)

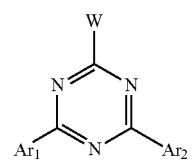

formula (F)

wherein Ar$_1$ and Ar$_2$ are defined as above, and
W is selected from the group consisting of F, Cl, and Br; and
iv) reacting at least one compound of formula (F) obtained according to step iii) and at least one compound of formula (G),

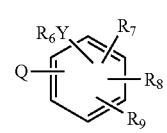

formula (G)

wherein Y, Q, $R^6$, $R^7$, $R^8$ and $R^9$ are defined as above,
in the presence of an at least one acid to obtain a compound of formula (A).

2. The process according to claim 1, comprising a step of:
v) reacting the product obtained according to step iv) with at least one alkyl halide or at least one acyl halide in presence of a base to obtain a compound of formula (A).

3. The process according to claim 1, wherein in step (i) the at least one acid is selected from the group consisting of inorganic acids, Lewis acids, and organic acids.

4. The process according to claim 3, wherein in step (i) the Lewis acids are selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2 \cdot O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3\!-\!S(\!=\!O)_2O$, $CH_3\!-\!S(\!=\!O)_2O$, or I;

$BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-bromo-2,6-di-tert-butylphenoxide), $LiClO_4$, $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), $Zr(acetylacetonate)_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, Ag(acetate), $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri\text{-}fluoromethanesulfonate)_2$ and $Cu(tosylate)_2$.

5. The process according to claim 4, wherein in step (i) the at least one Lewis acid is selected from the group consisting of $BX_3$, $BX_3 \cdot (C_2H_5)_2O$, $BX_3 \cdot S(CH_3)_2$, $AlX_3$, $ZnX_2$, $FeX_3$ and $TiX_4$, whereby X in each case denotes F, Cl, or Br.

6. The process according to claim 1, wherein in step (i) the molar ratio of the at least one acid to the at least one compound of formula (C) is in the range of 1:10 to 10:1.

7. The process according to claim 1, wherein in step (i) the molar ratio of the at least one compound of formula (B1) to the at least one compound of formula (C) is in the range of 1:1 to 5:2.

8. The process according to claim 1, wherein in step ii) the at least one metal hydroxide is selected from the group consisting of NaOH, KOH, LiOH, Cs(OH), $Be(OH)_2$, $Mg(OH)_2$, $Ca(OH)_2$, $Sr(OH)_2$, $Ba(OH)_2$, and $Al(OH)_3$.

9. The process according to claim 1, wherein in step iii) the at least one halogenating agent is selected from the group consisting of thionyl chloride, thionyl bromide, phosphorus pentachloride, phosphorous trichloride and phosphorus oxychloride.

10. The process according to claim 1, wherein in step iv) the at least one acid is a Lewis acid selected from the group consisting of $AsX_3$, $GaX_3$, $BX_3$, $BX_3 \cdot (C_2H_5)_2O$, $BX_3 \cdot S(CH_3)_2$, $AlX_3$, $(C_2H_5)_2AlX$, $SbX_3$, $SbX_5$, $SnX_2$, $MgX_2$, $MgX_2 \cdot O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, $CuX$, $CuX_2$ whereby X in each case denotes F, Cl, Br, $CF_3\!-\!S(\!=\!O)_2O$, $CH_3\!-\!S(\!=\!O)_2O$, or I;

$BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-bromo-2,6-di-tert-butylphenoxide), $LiClO_4$, $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), $Zr(acetylacetonate)_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, Ag(acetate), $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri\text{-}fluoromethanesulfonate)$; and $Cu(tosylate)_2$.

11. The process according to claim 1, wherein $R_1$, $R_2$, $R_3$, Ra and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, $C(\!=\!O)$ R and OR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

12. The process according to claim 11, wherein $R_1$, $R_2$, $R_3$, $R_4$ and $R_5$ are independently selected from the group consisting of hydrogen, methyl, substituted or unsubstituted phenyl, and OR;

wherein OR is selected from the group consisting of OH, $OCH_3$, and $OC_8H_{17}$.

13. The process according to claim 1, wherein $R^6$ is selected from hydrogen, substituted or unsubstituted, linear or branched $C_2$-$C_{24}$ alkyl and substituted or unsubstituted $C_6$-$C_{24}$ aryl;

Y is selected from hydrogen and O; with the proviso that in case Y is hydrogen, then $R_6$ is not present;

T is selected from hydrogen or OH; and $R_7$, $R_8$ and $R_9$ is selected from hydrogen, substituted or unsubstituted, linear or branched $C_1$-$C_{24}$ alkyl, substituted or unsubstituted $C_6$-$C_{24}$ aryl, $C(\!=\!O)R$, OR, $OC(\!=\!O)R$; wherein R is independently selected from the group consisting of hydrogen, substituted or unsubstituted, linear or branched $C_1$-$C_{24}$ alkyl.

14. The process according to claim 1, wherein the compound of formula (A) is selected from the group consisting of:

formula (A1)
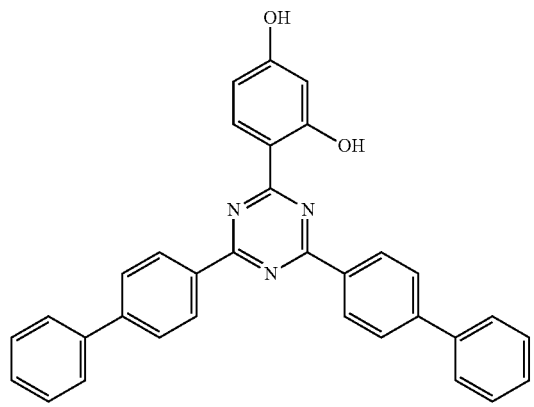
formula (A2)
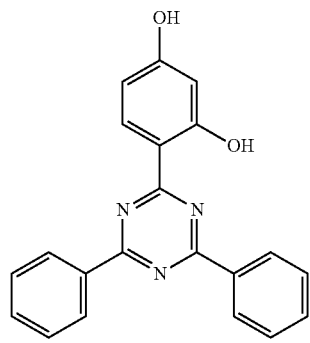
formula (A3)
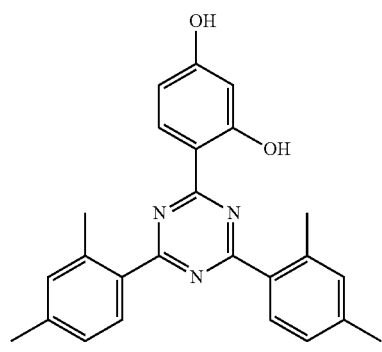
formula (A4)
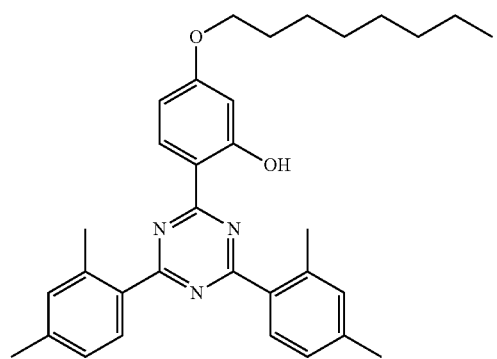
formula (A5)
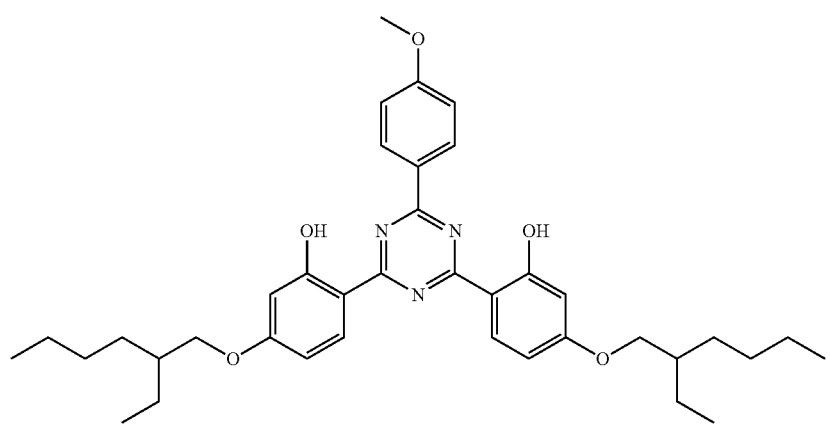
formula (A6)
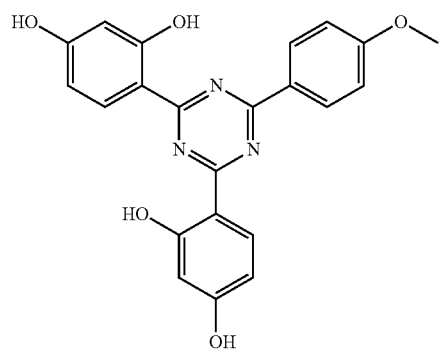
formula (A8)
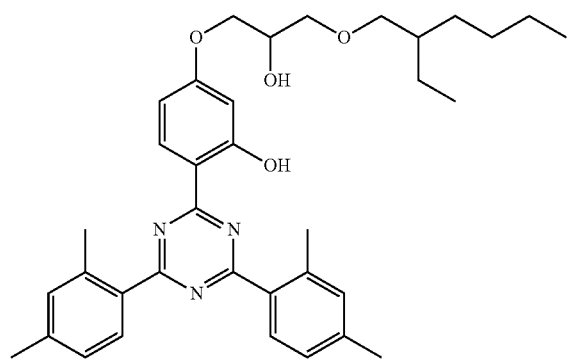

-continued
formula (A9)
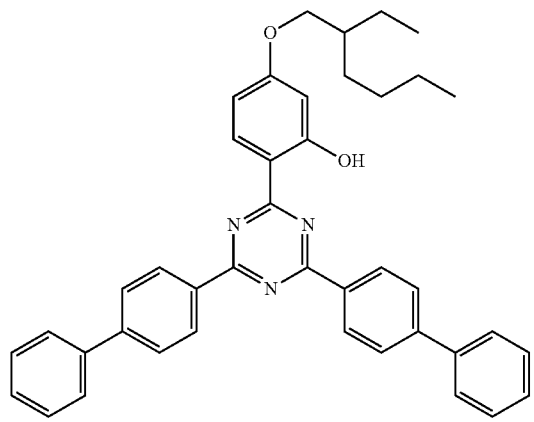
formula (A10)
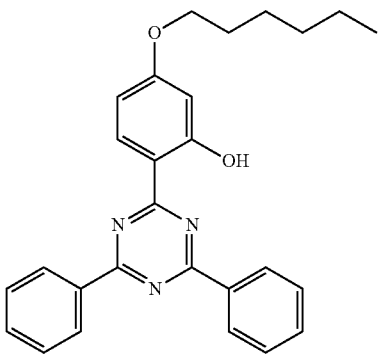
formula (A11a)
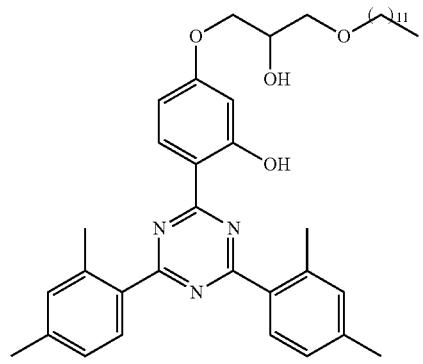
formula (A11b)
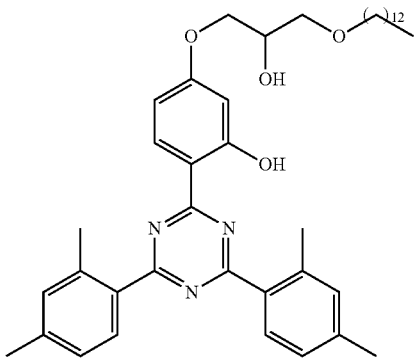
formula (A12)
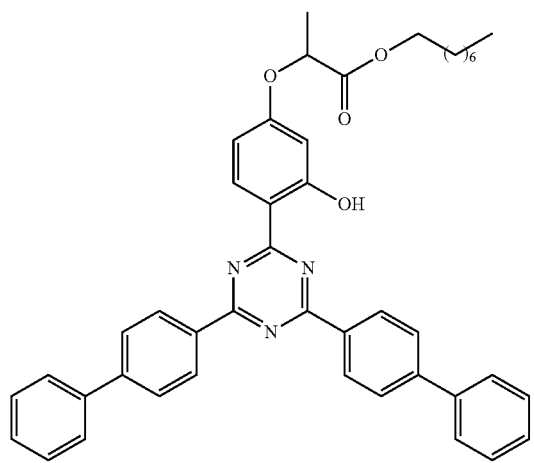
formula (A12a)
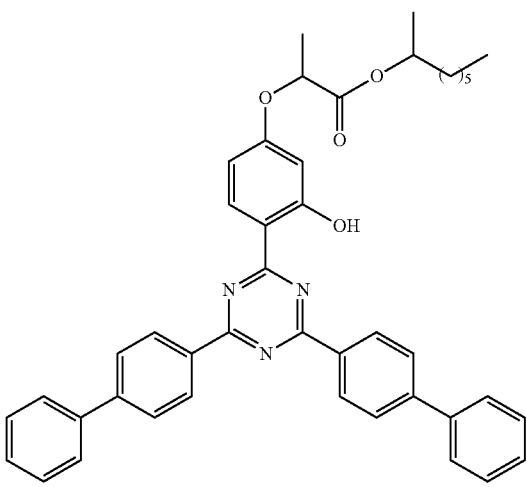
* * * * *